US006436654B1

United States Patent
Berkenstam et al.

(12)
(10) Patent No.: US 6,436,654 B1
(45) Date of Patent: Aug. 20, 2002

(54) METHODS FOR IDENTIFYING COMPOUNDS THAT MODULATE HIF-1α

(75) Inventors: Anders Berkenstam; Lorenz Poellinger, both of Stockholm (SE)

(73) Assignee: Pharmacia & Upjohn AB, Stockholm (SE)

(*) Notice: Subject to any disclaimer, the term of this patent is extended or adjusted under 35 U.S.C. 154(b) by 0 days.

(21) Appl. No.: 09/438,833

(22) Filed: Nov. 12, 1999

Related U.S. Application Data

(60) Provisional application No. 60/109,179, filed on Nov. 20, 1998.

(30) Foreign Application Priority Data

Nov. 13, 1998 (SE) ............................................. 9803891-2

(51) Int. Cl.[7] .......................... G01N 33/53; C07K 14/00
(52) U.S. Cl. ........................... 435/7.8; 435/7.2; 530/350
(58) Field of Search .................... 435/7.2, 7.8; 530/350

(56) References Cited

FOREIGN PATENT DOCUMENTS

WO        WO 9639426      * 12/1996

OTHER PUBLICATIONS

Jiang et al. Transactivation and Inhibitory Domains of Hypoxia–inducible Factor 1alpha. Journal of Biological Chemistry. 1997, vol. 272, No. 31, pp. 19253–19260.*
Huang, L.E.H., Activation of Hypoxia–inducible Transcription Factor Depends Primarily upon Redox–sensitive Stabilization of Its alpha Subunit. J. Biol. Chem. 1996. vol. 271(50) pp. 32253–32269.*
Kallio, P.J., SIgnal transduction in hypoxic cells: inducible nuclear translocation and recruitment of the CBP/p300 coactivator by the hypoxia–incucible factor–1 alpha. EMBO Journal. 1998. vol. 17(22) pp. 6573–6586.*
Pugh, C.W., Activation of Hypoxia–inducible Factor–1; Definition of Regulatory Domains within the alpha Subunit. J. Biol. Chem. vol. 272(17) pp. 11205–11214.*
Wang, Guang L., et al. "Hypoxia–inducible factor 1 is a basic–helix–loop–helix–PAS heterodimer regulated by cellular $O_2$ tension", *Proc. Natl. Acad. Sci. USA*, (Jun. 1995) vol. 92, pp. 5510–5514.*

Pugh, Christopher W., et al. "Activation of Hypoxia–inducible Factor–1; Definition of Regulatory Domains within the α Subunit", *The Journal of Biological Chemistry*, (Apr. 25, 1997) vol. 272, No. 17, pp. 11205–11214.*
Jiang, Bing–Hua, et al. "Transactivation and Inhibitory Domains of Hypoxia–inducible Factor 1α", *The Journal of Biological Chemistry*, (Aug. 1, 1997) vol. 272, No. 31, pp. 19253–19260.*
Kallio, Pekka J., et al. "SIgnal transduction in hypoxic cells; inducible nuclear translocation and recruitment of the CBP/p300 coactivator by the hypoxia–inducible factor–1α", *The EMBO Journal*, (1998) vol. 17, No. 22, pp. 6573–6586.*
Ema, Masatsugu, et al., "Molecular mechanisms of transcription activation by HLF and HIF1α in response to hypoxia: their stabilization and redox signal–induced interaction with CBP/p300", *The EMBO Journal*, (1999) vol. 18, No. 7, pp. 1905–1914.*

* cited by examiner

*Primary Examiner*—Prema Mertz
*Assistant Examiner*—Joseph F. Murphy
(74) *Attorney, Agent, or Firm*—Fish & Richardson P.C.

(57) ABSTRACT

The present invention relates to a method for identifying compounds capable of modulating the function of a functional domain of human HIF-1α, said method comprising (i) contacting a candidate compound with a variant of human HIF-1α, said variant essentially lacking at least one functional domain of human HIF-1α, or having a mutation making at least one functional domain of human HIF-1α essentially inactive, said functional domain or domains being selected from the group consisting of
  (a) the PAS-B domain located in human HIF-1α between amino acids 178 and 390,
  (b) the C-terminal nuclear localization sequence (NLS) located in human HIF-1α essentially at amino acids 718 to 721, and
  (c) the transactivator/coactivator domain (N-TAD) located in human HIF-1α essentially between amino acids 531 to 584, and
  (d) the transactivator/coactivator domain (C-TAD) located in human HIF-1α essentially between amino acids 813 and 826, and
(ii) determining the effect of the candidate compound on the said variant.

50 Claims, 14 Drawing Sheets

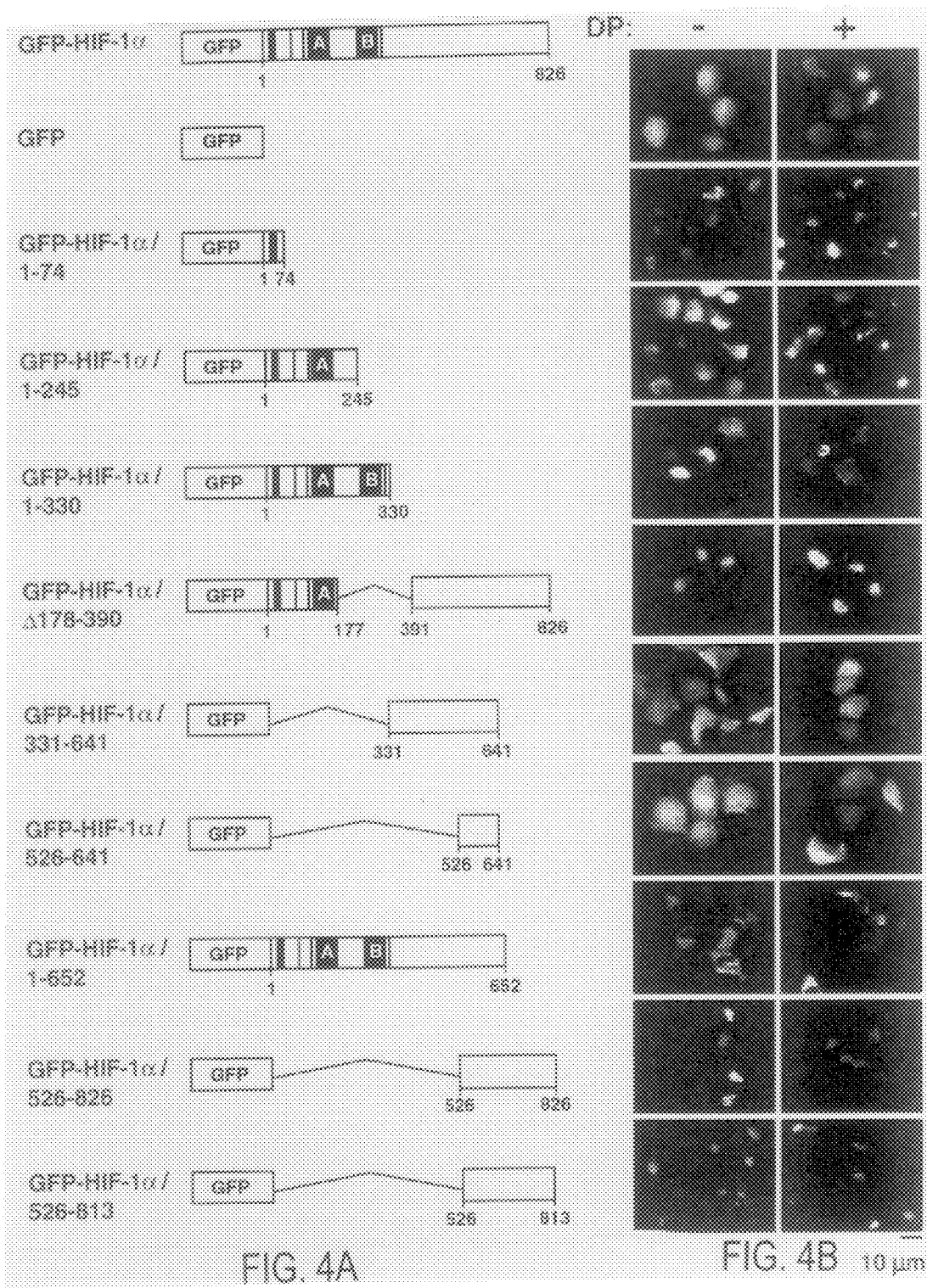
FIG. 4A    FIG. 4B 10 μm

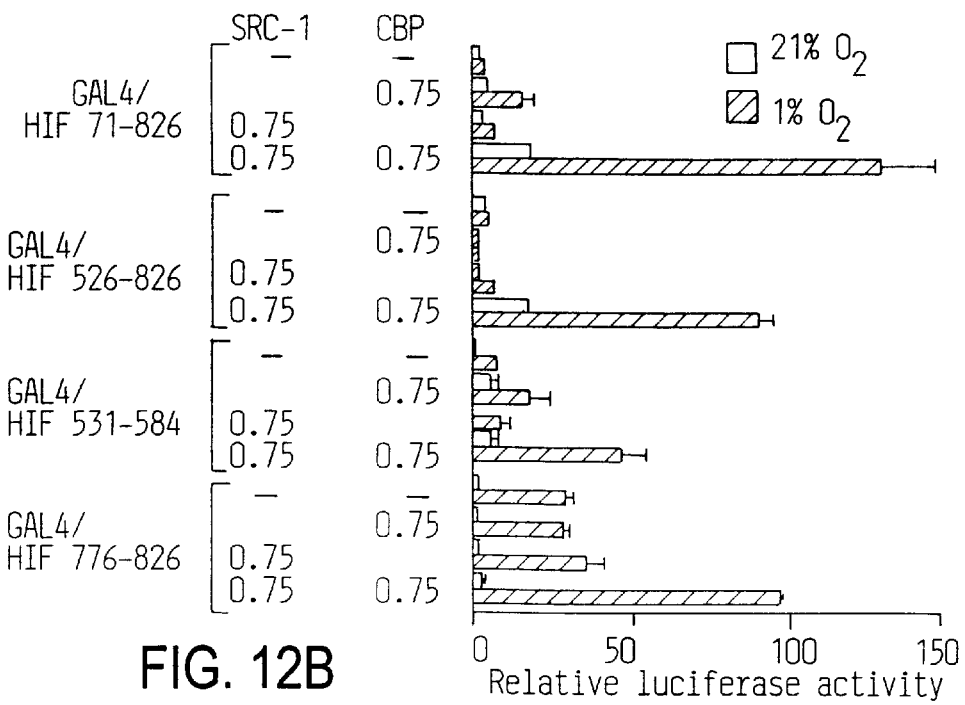
FIG. 12B
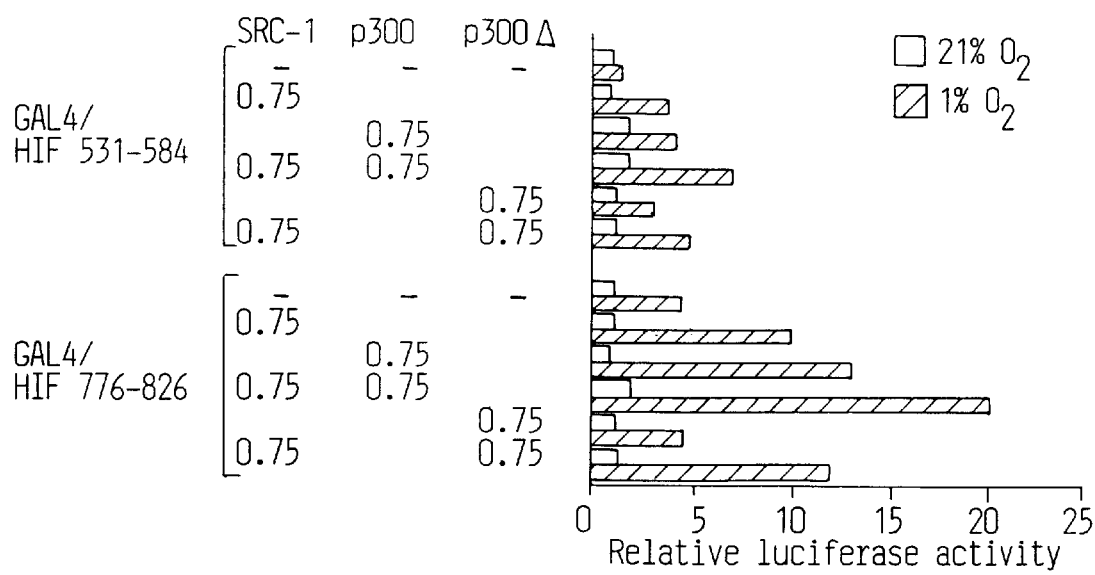
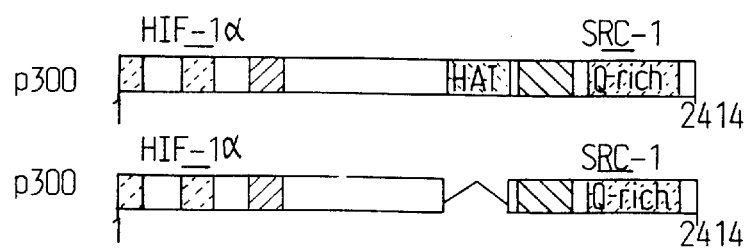
FIG. 12C

SEQUENCE LISTING

<160> NUMBER OF SEQ ID NOS: 15

<210> SEQ ID NO 1
<211> LENGTH: 826
<212> TYPE: PRT
<213> ORGANISM: Homo sapiens
<300> PUBLICATION INFORMATION:
<303> JOURNAL: Proc. Natl. Acad. Sci. U.S.A.
<304> VOLUME: 92
<306> PAGES: 5510-5514
<308> DATABASE ACCESSION NUMBER: GenBank U22431
<309> DATABASE ENTRY DATE: 1995-06-28

<400> SEQUENCE: 1

```
Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
```

```
                  325                 330                 335
Cys Val Asn Tyr Val Val Ser Gly Ile Ile Gln His Asp Leu Ile Phe
                340                 345                 350
Ser Leu Gln Gln Thr Glu Cys Val Leu Lys Pro Val Glu Ser Ser Asp
                355                 360                 365
Met Lys Met Thr Gln Leu Phe Thr Lys Val Glu Ser Glu Asp Thr Ser
                370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                    405                 410                 415
Asp Thr Glu Thr Asp Asp Gln Gln Leu Glu Glu Val Pro Leu Tyr Asn
                420                 425                 430
Asp Val Met Leu Pro Ser Pro Asn Glu Lys Leu Gln Asn Ile Asn Leu
                435                 440                 445
Ala Met Ser Pro Leu Pro Thr Ala Glu Thr Pro Lys Pro Leu Arg Ser
450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
                500                 505                 510
Pro Asn Ser Pro Ser Glu Tyr Cys Phe Tyr Val Asp Ser Asp Met Val
                515                 520                 525
Asn Glu Phe Lys Leu Glu Leu Val Glu Lys Leu Phe Ala Glu Asp Thr
                530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
                580                 585                 590
Ala Ser Pro Gln Ser Thr Val Thr Val Phe Gln Gln Thr Gln Ile Gln
                595                 600                 605
Glu Pro Thr Ala Asn Ala Thr Thr Thr Thr Ala Thr Thr Asp Glu Leu
                610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                    645                 650                 655
Ser Pro Tyr Arg Asp Thr Gln Ser Arg Thr Ala Ser Pro Asn Arg Ala
                660                 665                 670
Gly Lys Gly Val Ile Glu Gln Thr Glu Lys Ser His Pro Arg Ser Pro
                675                 680                 685
Asn Val Leu Ser Val Ala Leu Ser Gln Arg Thr Thr Val Pro Glu Glu
                690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                    725                 730                 735
Leu Leu Gln Gln Pro Asp Asp His Ala Ala Thr Thr Ser Leu Ser Trp
                740                 745                 750
```

-continued

```
Lys Arg Val Lys Gly Cys Lys Ser Ser Glu Gln Asn Gly Met Glu Gln
        755                 760                 765

Lys Thr Ile Ile Leu Ile Pro Ser Asp Leu Ala Cys Arg Leu Leu Gly
        770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
        820                 825

<210> SEQ ID NO 2
<211> LENGTH: 74
<212> TYPE: PRT
<213> ORGANISM: Artificial Sequence
<220> FEATURE:
<223> OTHER INFORMATION: Description of Artificial Sequence: Subdomain
      1-74 of human HIF-1 alpha

<400> SEQUENCE: 2

Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp
65                  70

<210> SEQ ID NO 3
<211> LENGTH: 245
<212> TYPE: PRT
<213> ORGANISM: Artificial Sequence
<220> FEATURE:
<223> OTHER INFORMATION: Description of Artificial Sequence: Subdomain
      1-245 of human HIF-1 alpha

<400> SEQUENCE: 3

Met Glu Gly Ala Gly Gly Ala Asn Asp Lys Lys Lys Ile Ser Ser Glu
 1               5                  10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140
```

```
Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
        180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg
                245

<210> SEQ ID NO 4
<211> LENGTH: 330
<212> TYPE: PRT
<213> ORGANISM: Artificial Sequence
<220> FEATURE:
<223> OTHER INFORMATION: Description of Artificial Sequence: Subdomain
      1-330 of human HIF-1 alpha

<400> SEQUENCE: 4

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
        180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
```

```
                    245                 250                 255
Glu Arg Ile Thr Glu Leu Met Gly Tyr Glu Pro Glu Leu Leu Gly
                260                 265                 270

Arg Ser Ile Tyr Glu Tyr His Ala Leu Asp Ser Asp His Leu Thr
            275                 280                 285

Lys Thr His His Asp Met Phe Thr Lys Gly Gln Val Thr Thr Gly Gln
        290                 295                 300

Tyr Arg Met Leu Ala Lys Arg Gly Tyr Val Trp Val Glu Thr Gln
305                 310                 315                 320

Ala Thr Val Ile Tyr Asn Thr Lys Asn Ser
                325                 330

<210> SEQ ID NO 5
<211> LENGTH: 652
<212> TYPE: PRT
<213> ORGANISM: Artificial Sequence
<220> FEATURE:
<223> OTHER INFORMATION: Description of Artificial Sequence: Subdomain
      1-652 of human HIF-1 alpha

<400> SEQUENCE: 5

Met Glu Gly Ala Gly Gly Ala Asn Asp Lys Lys Lys Ile Ser Ser Glu
  1               5                  10                  15

Arg Arg Lys Glu Lys Ser Arg Asp Ala Ala Arg Ser Arg Arg Ser Lys
                 20                  25                  30

Glu Ser Glu Val Phe Tyr Glu Leu Ala His Gln Leu Pro Leu Pro His
             35                  40                  45

Asn Val Ser Ser His Leu Asp Lys Ala Ser Val Met Arg Leu Thr Ile
         50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
        130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Leu Leu Gly
            260                 265                 270
```

```
Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
        290                 295                 300

Tyr Arg Met Leu Ala Lys Arg Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
        595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr
                645                 650

<210> SEQ ID NO 6
<211> LENGTH: 613
<212> TYPE: PRT
<213> ORGANISM: Artificial Sequence

<400> SEQUENCE: 6
```

-continued

```
Met Glu Gly Ala Gly Ala Asn Asp Lys Lys Ile Ser Ser Glu
 1               5                  10                 15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Lys Lys Glu Pro Asp Ala Leu Thr Leu Leu Ala Pro Ala Ala Gly
            180                 185                 190

Asp Thr Ile Ile Ser Leu Asp Phe Gly Ser Asn Asp Thr Glu Thr Asp
        195                 200                 205

Asp Gln Gln Leu Glu Glu Val Pro Leu Tyr Asn Asp Val Met Leu Pro
    210                 215                 220

Ser Pro Asn Glu Lys Leu Gln Asn Ile Asn Leu Ala Met Ser Pro Leu
225                 230                 235                 240

Pro Thr Ala Glu Thr Pro Lys Pro Leu Arg Ser Ser Ala Asp Pro Ala
                245                 250                 255

Leu Asn Gln Glu Val Ala Leu Lys Leu Glu Pro Asn Pro Glu Ser Leu
            260                 265                 270

Glu Leu Ser Phe Thr Met Pro Gln Ile Gln Asp Gln Thr Pro Ser Pro
        275                 280                 285

Ser Asp Gly Ser Thr Arg Gln Ser Ser Pro Glu Pro Asn Ser Pro Ser
    290                 295                 300

Glu Tyr Cys Phe Tyr Val Asp Ser Asp Met Val Asn Glu Phe Lys Leu
305                 310                 315                 320

Glu Leu Val Glu Lys Leu Phe Ala Glu Asp Thr Glu Ala Lys Asn Pro
                325                 330                 335

Phe Ser Thr Gln Asp Thr Asp Leu Asp Leu Glu Met Leu Ala Pro Tyr
            340                 345                 350

Ile Pro Met Asp Asp Asp Phe Gln Leu Arg Ser Phe Asp Gln Leu Ser
        355                 360                 365

Pro Leu Glu Ser Ser Ser Ala Ser Pro Glu Ser Ala Ser Pro Gln Ser
    370                 375                 380

Thr Val Thr Val Phe Gln Gln Thr Gln Ile Gln Glu Pro Thr Ala Asn
385                 390                 395                 400

Ala Thr Thr Thr Thr Ala Thr Thr Asp Glu Leu Lys Thr Val Thr Lys
                405                 410                 415
```

```
Asp Arg Met Glu Asp Ile Lys Ile Leu Ile Ala Ser Pro Ser Pro Thr
            420                 425                 430

His Ile His Lys Glu Thr Thr Ser Ala Thr Ser Ser Pro Tyr Arg Asp
            435                 440                 445

Thr Gln Ser Arg Thr Ala Ser Pro Asn Arg Ala Gly Lys Gly Val Ile
            450                 455                 460

Glu Gln Thr Glu Lys Ser His Pro Arg Ser Pro Asn Val Leu Ser Val
465                 470                 475                 480

Ala Leu Ser Gln Arg Thr Thr Val Pro Glu Glu Leu Asn Pro Lys
                485                 490                 495

Ile Leu Ala Leu Gln Asn Ala Gln Arg Lys Arg Lys Met Glu His Asp
                500                 505                 510

Gly Ser Leu Phe Gln Ala Val Gly Ile Gly Thr Leu Leu Gln Gln Pro
                515                 520                 525

Asp Asp His Ala Ala Thr Thr Ser Leu Ser Trp Lys Arg Val Lys Gly
            530                 535                 540

Cys Lys Ser Ser Glu Gln Asn Gly Met Glu Gln Lys Thr Ile Ile Leu
545                 550                 555                 560

Ile Pro Ser Asp Leu Ala Cys Arg Leu Leu Gly Gln Ser Met Asp Glu
                565                 570                 575

Ser Gly Leu Pro Gln Leu Thr Ser Tyr Asp Cys Glu Val Asn Ala Pro
                580                 585                 590

Ile Gln Gly Ser Arg Asn Leu Leu Gln Gly Glu Glu Leu Leu Arg Ala
            595                 600                 605

Leu Asp Gln Val Asn
            610

<210> SEQ ID NO 7
<211> LENGTH: 311
<212> TYPE: PRT
<213> ORGANISM: Artificial Sequence
<220> FEATURE:
<223> OTHER INFORMATION: Description of Artificial Sequence: Subdomain
      331-641 of human HIF-1 alpha

<400> SEQUENCE: 7

Gln Pro Gln Cys Ile Val Cys Val Asn Tyr Val Val Ser Gly Ile Ile
1               5                   10                  15

Gln His Asp Leu Ile Phe Ser Leu Gln Gln Thr Glu Cys Val Leu Lys
            20                  25                  30

Pro Val Glu Ser Ser Asp Met Lys Met Thr Gln Leu Phe Thr Lys Val
        35                  40                  45

Glu Ser Glu Asp Thr Ser Ser Leu Phe Asp Lys Leu Lys Lys Glu Pro
50                  55                  60

Asp Ala Leu Thr Leu Leu Ala Pro Ala Ala Gly Asp Thr Ile Ile Ser
65                  70                  75                  80

Leu Asp Phe Gly Ser Asn Asp Thr Glu Thr Asp Asp Gln Gln Leu Glu
                85                  90                  95

Glu Val Pro Leu Tyr Asn Asp Val Met Leu Pro Ser Pro Asn Glu Lys
            100                 105                 110

Leu Gln Asn Ile Asn Leu Ala Met Ser Pro Leu Pro Thr Ala Glu Thr
        115                 120                 125

Pro Lys Pro Leu Arg Ser Ser Ala Asp Pro Ala Leu Asn Gln Glu Val
    130                 135                 140

Ala Leu Lys Leu Glu Pro Asn Pro Glu Ser Leu Glu Leu Ser Phe Thr
145                 150                 155                 160
```

```
Met Pro Gln Ile Gln Asp Gln Thr Pro Ser Pro Ser Asp Gly Ser Thr
                165                 170                 175
Arg Gln Ser Ser Pro Glu Pro Asn Ser Pro Ser Glu Tyr Cys Phe Tyr
            180                 185                 190
Val Asp Ser Asp Met Val Asn Glu Phe Lys Leu Glu Leu Val Glu Lys
        195                 200                 205
Leu Phe Ala Glu Asp Thr Glu Ala Lys Asn Pro Phe Ser Thr Gln Asp
    210                 215                 220
Thr Asp Leu Asp Leu Glu Met Leu Ala Pro Tyr Ile Pro Met Asp Asp
225                 230                 235                 240
Asp Phe Gln Leu Arg Ser Phe Asp Gln Leu Ser Pro Leu Glu Ser Ser
                245                 250                 255
Ser Ala Ser Pro Glu Ser Ala Ser Pro Gln Ser Thr Val Thr Val Phe
            260                 265                 270
Gln Gln Thr Gln Ile Gln Glu Pro Thr Ala Asn Ala Thr Thr Thr Thr
        275                 280                 285
Ala Thr Thr Asp Glu Leu Lys Thr Val Thr Lys Asp Arg Met Glu Asp
    290                 295                 300
Ile Lys Ile Leu Ile Ala Ser
305                 310

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Subdomain
      526-641 of human HIF-1 alpha

<400> SEQUENCE: 8

Asp Met Val Asn Glu Phe Lys Leu Glu Leu Val Glu Lys Leu Phe Ala
  1               5                  10                  15
Glu Asp Thr Glu Ala Lys Asn Pro Phe Ser Thr Gln Asp Thr Asp Leu
             20                  25                  30
Asp Leu Glu Met Leu Ala Pro Tyr Ile Pro Met Asp Asp Asp Phe Gln
         35                  40                  45
Leu Arg Ser Phe Asp Gln Leu Ser Pro Leu Glu Ser Ser Ser Ala Ser
     50                  55                  60
Pro Glu Ser Ala Ser Pro Gln Ser Thr Val Thr Val Phe Gln Gln Thr
 65                  70                  75                  80
Gln Ile Gln Glu Pro Thr Ala Asn Ala Thr Thr Thr Thr Ala Thr Thr
                 85                  90                  95
Asp Glu Leu Lys Thr Val Thr Lys Asp Arg Met Glu Asp Ile Lys Ile
            100                 105                 110
Leu Ile Ala Ser
        115

<210> SEQ ID NO 9
<211> LENGTH: 288
<212> TYPE: PRT
<213> ORGANISM: Artificial Sequence
<220> FEATURE:
<223> OTHER INFORMATION: Description of Artificial Sequence: Subdomain
      526-813 of human HIF-1 alpha

<400> SEQUENCE: 9

Asp Met Val Asn Glu Phe Lys Leu Glu Leu Val Glu Lys Leu Phe Ala
  1               5                  10                  15
```

-continued

```
Glu Asp Thr Glu Ala Lys Asn Pro Phe Ser Thr Gln Asp Thr Asp Leu
             20                  25                  30

Asp Leu Glu Met Leu Ala Pro Tyr Ile Pro Met Asp Asp Asp Phe Gln
         35                  40                  45

Leu Arg Ser Phe Asp Gln Leu Ser Pro Leu Glu Ser Ser Ser Ala Ser
     50                  55                  60

Pro Glu Ser Ala Ser Pro Gln Ser Thr Val Thr Val Phe Gln Gln Thr
 65                  70                  75                  80

Gln Ile Gln Glu Pro Thr Ala Asn Ala Thr Thr Thr Thr Ala Thr Thr
                 85                  90                  95

Asp Glu Leu Lys Thr Val Thr Lys Asp Arg Met Glu Asp Ile Lys Ile
            100                 105                 110

Leu Ile Ala Ser Pro Ser Pro Thr His Ile His Lys Glu Thr Thr Ser
        115                 120                 125

Ala Thr Ser Ser Pro Tyr Arg Asp Thr Gln Ser Arg Thr Ala Ser Pro
    130                 135                 140

Asn Arg Ala Gly Lys Gly Val Ile Glu Gln Thr Glu Lys Ser His Pro
145                 150                 155                 160

Arg Ser Pro Asn Val Leu Ser Val Ala Leu Ser Gln Arg Thr Thr Val
                165                 170                 175

Pro Glu Glu Glu Leu Asn Pro Lys Ile Leu Ala Leu Gln Asn Ala Gln
            180                 185                 190

Arg Lys Arg Lys Met Glu His Asp Gly Ser Leu Phe Gln Ala Val Gly
        195                 200                 205

Ile Gly Thr Leu Leu Gln Gln Pro Asp Asp His Ala Ala Thr Thr Ser
    210                 215                 220

Leu Ser Trp Lys Arg Val Lys Gly Cys Lys Ser Ser Glu Gln Asn Gly
225                 230                 235                 240

Met Glu Gln Lys Thr Ile Ile Leu Ile Pro Ser Asp Leu Ala Cys Arg
                245                 250                 255

Leu Leu Gly Gln Ser Met Asp Glu Ser Gly Leu Pro Gln Leu Thr Ser
            260                 265                 270

Tyr Asp Cys Glu Val Asn Ala Pro Ile Gln Gly Ser Arg Asn Leu Leu
        275                 280                 285
```

<210> SEQ ID NO 10
<211> LENGTH: 301
<212> TYPE: PRT
<213> ORGANISM: Artificial Sequence
<220> FEATURE:
<223> OTHER INFORMATION: Description of Artificial Sequence: Subdomain
      526-826 of human HIF-1 alpha

<400> SEQUENCE: 10

```
Asp Met Val Asn Glu Phe Lys Leu Glu Leu Val Glu Lys Leu Phe Ala
  1               5                  10                  15

Glu Asp Thr Glu Ala Lys Asn Pro Phe Ser Thr Gln Asp Thr Asp Leu
             20                  25                  30

Asp Leu Glu Met Leu Ala Pro Tyr Ile Pro Met Asp Asp Asp Phe Gln
         35                  40                  45

Leu Arg Ser Phe Asp Gln Leu Ser Pro Leu Glu Ser Ser Ser Ala Ser
     50                  55                  60

Pro Glu Ser Ala Ser Pro Gln Ser Thr Val Thr Val Phe Gln Gln Thr
 65                  70                  75                  80

Gln Ile Gln Glu Pro Thr Ala Asn Ala Thr Thr Thr Thr Ala Thr Thr
```

```
                    85                  90                  95
Asp Glu Leu Lys Thr Val Thr Lys Asp Arg Met Glu Asp Ile Lys Ile
            100                 105                 110

Leu Ile Ala Ser Pro Ser Pro Thr His Ile His Lys Glu Thr Thr Ser
            115                 120                 125

Ala Thr Ser Ser Pro Tyr Arg Asp Thr Gln Ser Arg Thr Ala Ser Pro
        130                 135                 140

Asn Arg Ala Gly Lys Gly Val Ile Glu Gln Thr Glu Lys Ser His Pro
145                 150                 155                 160

Arg Ser Pro Asn Val Leu Ser Val Ala Leu Ser Gln Arg Thr Thr Val
                165                 170                 175

Pro Glu Glu Glu Leu Asn Pro Lys Ile Leu Ala Leu Gln Asn Ala Gln
            180                 185                 190

Arg Lys Arg Lys Met Glu His Asp Gly Ser Leu Phe Gln Ala Val Gly
        195                 200                 205

Ile Gly Thr Leu Leu Gln Gln Pro Asp Asp His Ala Ala Thr Thr Ser
    210                 215                 220

Leu Ser Trp Lys Arg Val Lys Gly Cys Lys Ser Ser Glu Gln Asn Gly
225                 230                 235                 240

Met Glu Gln Lys Thr Ile Ile Leu Ile Pro Ser Asp Leu Ala Cys Arg
                245                 250                 255

Leu Leu Gly Gln Ser Met Asp Glu Ser Gly Leu Pro Gln Leu Thr Ser
            260                 265                 270

Tyr Asp Cys Glu Val Asn Ala Pro Ile Gln Gly Ser Arg Asn Leu Leu
        275                 280                 285

Gln Gly Glu Glu Leu Leu Arg Ala Leu Asp Gln Val Asn
    290                 295                 300

<210> SEQ ID NO 11
<211> LENGTH: 756
<212> TYPE: PRT
<213> ORGANISM: Artificial Sequence
<220> FEATURE:
<223> OTHER INFORMATION: Description of Artificial Sequence: Subdomain
      71-826 of human HIF-1 alpha

<400> SEQUENCE: 11

Lys Leu Leu Asp Ala Gly Asp Leu Asp Ile Glu Asp Asp Met Lys Ala
 1               5                  10                  15

Gln Met Asn Cys Phe Tyr Leu Lys Ala Leu Asp Gly Phe Val Met Val
            20                  25                  30

Leu Thr Asp Asp Gly Asp Met Ile Tyr Ile Ser Asp Asn Val Asn Lys
        35                  40                  45

Tyr Met Gly Leu Thr Gln Phe Glu Leu Thr Gly His Ser Val Phe Asp
    50                  55                  60

Phe Thr His Pro Cys Asp His Glu Glu Met Arg Glu Met Leu Thr His
65                  70                  75                  80

Arg Asn Gly Leu Val Lys Lys Gly Lys Glu Gln Asn Thr Gln Arg Ser
                85                  90                  95

Phe Phe Leu Arg Met Lys Cys Thr Leu Thr Ser Arg Gly Arg Thr Met
            100                 105                 110

Asn Ile Lys Ser Ala Thr Trp Lys Val Leu His Cys Thr Gly His Ile
        115                 120                 125

His Val Tyr Asp Thr Asn Ser Asn Gln Pro Gln Cys Gly Tyr Lys Lys
    130                 135                 140
```

```
Pro Pro Met Thr Cys Leu Val Leu Ile Cys Glu Pro Ile Pro His Pro
145                 150                 155                 160

Ser Asn Ile Glu Ile Pro Leu Asp Ser Lys Thr Phe Leu Ser Arg His
            165                 170                 175

Ser Leu Asp Met Lys Phe Ser Tyr Cys Asp Glu Arg Ile Thr Glu Leu
                180                 185                 190

Met Gly Tyr Glu Pro Glu Glu Leu Leu Gly Arg Ser Ile Tyr Glu Tyr
            195                 200                 205

Tyr His Ala Leu Asp Ser Asp His Leu Thr Lys Thr His His Asp Met
        210                 215                 220

Phe Thr Lys Gly Gln Val Thr Thr Gly Gln Tyr Arg Met Leu Ala Lys
225                 230                 235                 240

Arg Gly Gly Tyr Val Trp Val Glu Thr Gln Ala Thr Val Ile Tyr Asn
                245                 250                 255

Thr Lys Asn Ser Gln Pro Gln Cys Ile Val Cys Val Asn Tyr Val Val
            260                 265                 270

Ser Gly Ile Ile Gln His Asp Leu Ile Phe Ser Leu Gln Gln Thr Glu
        275                 280                 285

Cys Val Leu Lys Pro Val Glu Ser Ser Asp Met Lys Met Thr Gln Leu
290                 295                 300

Phe Thr Lys Val Glu Ser Glu Asp Thr Ser Ser Leu Phe Asp Lys Leu
305                 310                 315                 320

Lys Lys Glu Pro Asp Ala Leu Thr Leu Leu Ala Pro Ala Ala Gly Asp
                325                 330                 335

Thr Ile Ile Ser Leu Asp Phe Gly Ser Asn Asp Thr Glu Thr Asp Asp
                340                 345                 350

Gln Gln Leu Glu Glu Val Pro Leu Tyr Asn Asp Val Met Leu Pro Ser
            355                 360                 365

Pro Asn Glu Lys Leu Gln Asn Ile Asn Leu Ala Met Ser Pro Leu Pro
370                 375                 380

Thr Ala Glu Thr Pro Lys Pro Leu Arg Ser Ser Ala Asp Pro Ala Leu
385                 390                 395                 400

Asn Gln Glu Val Ala Leu Lys Leu Glu Pro Asn Pro Glu Ser Leu Glu
                405                 410                 415

Leu Ser Phe Thr Met Pro Gln Ile Gln Asp Gln Thr Pro Ser Pro Ser
            420                 425                 430

Asp Gly Ser Thr Arg Gln Ser Ser Pro Glu Pro Asn Ser Pro Ser Glu
            435                 440                 445

Tyr Cys Phe Tyr Val Asp Ser Asp Met Val Asn Glu Phe Lys Leu Glu
            450                 455                 460

Leu Val Glu Lys Leu Phe Ala Glu Asp Thr Glu Ala Lys Asn Pro Phe
465                 470                 475                 480

Ser Thr Gln Asp Thr Asp Leu Asp Leu Glu Met Leu Ala Pro Tyr Ile
                485                 490                 495

Pro Met Asp Asp Asp Phe Gln Leu Arg Ser Phe Asp Gln Leu Ser Pro
                500                 505                 510

Leu Glu Ser Ser Ser Ala Ser Pro Glu Ser Ala Ser Pro Gln Ser Thr
            515                 520                 525

Val Thr Val Phe Gln Gln Thr Gln Ile Gln Glu Pro Thr Ala Asn Ala
            530                 535                 540

Thr Thr Thr Thr Ala Thr Thr Asp Glu Leu Lys Thr Val Thr Lys Asp
545                 550                 555                 560

Arg Met Glu Asp Ile Lys Ile Leu Ile Ala Ser Pro Ser Pro Thr His
```

```
                    565                 570                 575
Ile His Lys Glu Thr Ser Ala Thr Ser Ser Pro Tyr Arg Asp Thr
            580                 585                 590

Gln Ser Arg Thr Ala Ser Pro Asn Arg Ala Gly Lys Gly Val Ile Glu
        595                 600                 605

Gln Thr Glu Lys Ser His Pro Arg Ser Pro Asn Val Leu Ser Val Ala
    610                 615                 620

Leu Ser Gln Arg Thr Thr Val Pro Glu Glu Leu Asn Pro Lys Ile
625                 630                 635                 640

Leu Ala Leu Gln Asn Ala Gln Arg Lys Arg Lys Met Glu His Asp Gly
                645                 650                 655

Ser Leu Phe Gln Ala Val Gly Ile Gly Thr Leu Leu Gln Gln Pro Asp
            660                 665                 670

Asp His Ala Ala Thr Thr Ser Leu Ser Trp Lys Arg Val Lys Gly Cys
        675                 680                 685

Lys Ser Ser Glu Gln Asn Gly Met Glu Gln Lys Thr Ile Ile Leu Ile
    690                 695                 700

Pro Ser Asp Leu Ala Cys Arg Leu Leu Gly Gln Ser Met Asp Glu Ser
705                 710                 715                 720

Gly Leu Pro Gln Leu Thr Ser Tyr Asp Cys Glu Val Asn Ala Pro Ile
                725                 730                 735

Gln Gly Ser Arg Asn Leu Leu Gln Gly Glu Glu Leu Leu Arg Ala Leu
            740                 745                 750

Asp Gln Val Asn
        755

<210> SEQ ID NO 12
<211> LENGTH: 813
<212> TYPE: PRT
<213> ORGANISM: Artificial Sequence
<220> FEATURE:
<223> OTHER INFORMATION: Description of Artificial Sequence: Subdomain
      1-813 of human HIF-1 alpha

<400> SEQUENCE: 12

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160
```

-continued

```
Gln Asn Thr Gln Arg Ser Phe Phe Leu Arg Met Lys Cys Thr Leu Thr
            165                 170                 175
Ser Arg Gly Arg Thr Met Asn Ile Lys Ser Ala Thr Trp Lys Val Leu
        180                 185                 190
His Cys Thr Gly His Ile His Val Tyr Asp Thr Asn Ser Asn Gln Pro
    195                 200                 205
Gln Cys Gly Tyr Lys Lys Pro Pro Met Thr Cys Leu Val Leu Ile Cys
210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
            245                 250                 255
Glu Arg Ile Thr Glu Leu Met Gly Tyr Glu Pro Glu Glu Leu Leu Gly
        260                 265                 270
Arg Ser Ile Tyr Glu Tyr Tyr His Ala Leu Asp Ser Asp His Leu Thr
    275                 280                 285
Lys Thr His His Asp Met Phe Thr Lys Gly Gln Val Thr Thr Gly Gln
290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
            325                 330                 335
Cys Val Asn Tyr Val Val Ser Gly Ile Ile Gln His Asp Leu Ile Phe
        340                 345                 350
Ser Leu Gln Gln Thr Glu Cys Val Leu Lys Pro Val Glu Ser Ser Asp
    355                 360                 365
Met Lys Met Thr Gln Leu Phe Thr Lys Val Glu Ser Glu Asp Thr Ser
370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
            405                 410                 415
Asp Thr Glu Thr Asp Asp Gln Gln Leu Glu Glu Val Pro Leu Tyr Asn
        420                 425                 430
Asp Val Met Leu Pro Ser Pro Asn Glu Lys Leu Gln Asn Ile Asn Leu
    435                 440                 445
Ala Met Ser Pro Leu Pro Thr Ala Glu Thr Pro Lys Pro Leu Arg Ser
450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
            485                 490                 495
Gln Thr Pro Ser Pro Ser Asp Gly Ser Thr Arg Gln Ser Ser Pro Glu
        500                 505                 510
Pro Asn Ser Pro Ser Glu Tyr Cys Phe Tyr Val Asp Ser Asp Met Val
    515                 520                 525
Asn Glu Phe Lys Leu Glu Leu Val Glu Lys Leu Phe Ala Glu Asp Thr
530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Phe Gln Leu Arg Ser
            565                 570                 575
Phe Asp Gln Leu Ser Pro Leu Glu Ser Ser Ser Ala Ser Pro Glu Ser
```

```
                  580               585               590
Ala Ser Pro Gln Ser Thr Val Thr Val Phe Gln Gln Thr Gln Ile Gln
            595               600               605

Glu Pro Thr Ala Asn Ala Thr Thr Thr Ala Thr Thr Asp Glu Leu
    610               615               620

Lys Thr Val Thr Lys Asp Arg Met Glu Asp Ile Lys Ile Leu Ile Ala
625               630               635               640

Ser Pro Ser Pro Thr His Ile His Lys Glu Thr Thr Ser Ala Thr Ser
                645               650               655

Ser Pro Tyr Arg Asp Thr Gln Ser Arg Thr Ala Ser Pro Asn Arg Ala
            660               665               670

Gly Lys Gly Val Ile Glu Gln Thr Glu Lys Ser His Pro Arg Ser Pro
            675               680               685

Asn Val Leu Ser Val Ala Leu Ser Gln Arg Thr Thr Val Pro Glu Glu
    690               695               700

Glu Leu Asn Pro Lys Ile Leu Ala Leu Gln Asn Ala Gln Arg Lys Arg
705               710               715               720

Lys Met Glu His Asp Gly Ser Leu Phe Gln Ala Val Gly Ile Gly Thr
                725               730               735

Leu Leu Gln Gln Pro Asp Asp His Ala Ala Thr Thr Ser Leu Ser Trp
            740               745               750

Lys Arg Val Lys Gly Cys Lys Ser Ser Glu Gln Asn Gly Met Glu Gln
            755               760               765

Lys Thr Ile Ile Leu Ile Pro Ser Asp Leu Ala Cys Arg Leu Leu Gly
770               775               780

Gln Ser Met Asp Glu Ser Gly Leu Pro Gln Leu Thr Ser Tyr Asp Cys
785               790               795               800

Glu Val Asn Ala Pro Ile Gln Gly Ser Arg Asn Leu Leu
                805               810

<210> SEQ ID NO 13
<211> LENGTH: 54
<212> TYPE: PRT
<213> ORGANISM: Artificial Sequence
<220> FEATURE:
<223> OTHER INFORMATION: Description of Artificial Sequence: Subdomain
      531-584 of human HIF-1 alpha

<400> SEQUENCE: 13

Phe Lys Leu Glu Leu Val Glu Lys Leu Phe Ala Glu Asp Thr Glu Ala
  1               5                  10                  15

Lys Asn Pro Phe Ser Thr Gln Asp Thr Asp Leu Asp Leu Glu Met Leu
                20                  25                  30

Ala Pro Tyr Ile Pro Met Asp Asp Asp Phe Gln Leu Arg Ser Phe Asp
            35                  40                  45

Gln Leu Ser Pro Leu Glu
    50

<210> SEQ ID NO 14
<211> LENGTH: 51
<212> TYPE: PRT
<213> ORGANISM: Artificial Sequence
<220> FEATURE:
<223> OTHER INFORMATION: Description of Artificial Sequence: Subdomain
      776-826 of human HIF-1 alpha

<400> SEQUENCE: 14

Ser Asp Leu Ala Cys Arg Leu Leu Gly Gln Ser Met Asp Glu Ser Gly
```

```
                1               5              10              15
Leu Pro Gln Leu Thr Ser Tyr Asp Cys Glu Val Asn Ala Pro Ile Gln
                       20              25              30

Gly Ser Arg Asn Leu Leu Gln Gly Glu Glu Leu Leu Arg Ala Leu Asp
                35              40              45

Gln Val Asn
    50

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Subdomain
      776-813 of human HIF-1 alpha

<400> SEQUENCE: 15

Ser Asp Leu Ala Cys Arg Leu Leu Gly Gln Ser Met Asp Glu Ser Gly
  1               5              10              15

Leu Pro Gln Leu Thr Ser Tyr Asp Cys Glu Val Asn Ala Pro Ile Gln
                 20              25              30

Gly Ser Arg Asn Leu Leu
                 35
```

METHODS FOR IDENTIFYING COMPOUNDS THAT MODULATE HIF-1α

This application claims priority under 35 U.S.C. § 119 to provisional application U.S. No. 60/109,179, filed Nov. 20, 1998 and Swedish Patent Application 9803891, filed Nov. 13, 1998.

TECHNICAL FIELD

The present invention relates to novel variants of human hypoxia-inducible factor (HIF)-1α, as well as to the use of the said variants in screening assays for the elucidation of functional motifs in HIF-1α and for the identification of compounds that modulate the function of HIF-1α, said compounds being potentially useful in the regulation of target genes normally associated with HIF-1α such as genes involved in angiogenesis, erythropoiesis, and glycolysis.

BACKGROUND ART

Oxygen plays a critical biological role as the terminal electron acceptor in the mitochondria of vertebrate cells. During evolution, these cells have developed ways to sense alterations in oxygen levels and, during this process, acquired the ability to conditionally modulate the expression of genes involved in adaptive physiological responses to hypoxia including angiogenesis, erythropoiesis, and glycolysis. These genes include vascular endothelial growth factor, eryhtropoietin, several glycolytic enzymes and inducible nitric oxide synthase, and have all been shown to contain hypoxia responsive elements (HREs) (for reviews, see Guillemin and Krasnow (1997) Cell 89, 9–12; Wenger and Gassmann (1997) Biol. Chem. 378, 609–616). Under hypoxic conditions these response elements are recognized by a heterodimeric complex consisting of the hypoxia inducible factor (HIF)-1α and Arnt (Wang et al. (1995) Proc. Natl. Acad. Sci. USA 92, 5510–5514; Gradin et al. (1996) Mol. Cell. Biol. 16, 5221–5231). Both these transcription factors belong to the rapidly growing family of basic-helix-loop-helix (bHLH)-PAS (Per, Arnt, Sim) proteins. bHLH/PAS transcription factors play diverse biological roles.

The recent generation of HIF-1α- and Arnt-deficient embryonal stem cells and mice have indicated critical roles of both these factors in cardiovascular development and regulation of HRE-driven target genes (Maltepe et al. (1997) Nature 386, 403–407). The mechanism of hypoxia-dependent formation and activation of the HIF-1α-Arnt complex is presently poorly understood. The present inventors and others have recently demonstrated that HIF-1α protein levels are specifically and massively upregulated under hypoxic conditions in most if not in all cells. Since HIF-1α mRNA levels are unaltered in response to hypoxia, this mode of regulation appears to occur via a posttranscriptional step involving stabilization of HIF-1α protein levels (Huang et al. (1996) J. Biol. Chem. 271, 32253–32259; Kallio et al. (1997) Proc. Natl. Acad. Sci. USA 94, 5667–5672; Salceda and Caro (1997) J. Biol. Chem. 272, 22642–22647) preceding recruitment of Arnt and generation of a nuclear DNA binding complex.

Import of transcription factors into the nucleus is frequently a conditionally regulated process that occurs in response to various external and internal stimuli as well as to a developmental cues (Vandromme et al. (1996) Trends Biochem. Sci. 21, 59–64). Thus, this process can constitute a critical mechanism of regulation of transcription factor activity. Active, energy-dependent transport of proteins to the nucleus requires the presence of one or several nuclear localization signals (NLSs) within the transported protein (or its interaction partner). NLS motifs are short amino acid moieties that can be divided into two main groups: (i) the SV40 large T antigen type of NLS, characterized by a single cluster of four or more consecutive basic residues; and (ii) a bipartite NLS, consisting of two basic residues, a spacer of any ten amino acids, and a basic cluster where three of the next five residues are basic (Vandromme et al., supra, and references therein).

Purified HIF-1α, its amino acid sequence and polynucleotide sequence are disclosed by Wang et al. (1995) Proc. Natl. Acad. Sci. USA 92, 5510–5514 and in WO 96/39426. It has been suggested (Jiang et al. (1997) J. Biol. Chem. 272, 19253–19260) that amino acids 531–826 of HIF-1α contain two transactivation domains, TAD-N (amino acids 531–575) and TAD-C (amino acids 786–826). Further, Pugh et al. ((1997) J. Biol. Chem. 272, 11205–11214) defined two minimal domains within HIF-1α (amino acids 549–582 and 775–826) each of which could act to confer transcriptional activation.

There is a need for novel variants of human HIF-1α, which variants can be used in screening assays for the elucidation of functional motifs in HIF-1α and for the identification of compounds that modulate the function of HIF-1α, said compounds being potentially useful in the regulation of target genes normally associated with HIF-1α such as genes involved in angiogenesis, erythropoiesis, and glycolysis.

DESCRIPTION OF THE DRAWINGS

FIG. 4 Subcellular distribution of GFP-HIF-1α fusion proteins. (A) Schematic presentation of fusion proteins. All expression constructs were assembled into pCMX-SAH/Y145F vector expressing a humanized GFP under the control of the CMV promoter. (B) Subcellular distribution of GFP-HIF-1α chimeric proteins. Fusion constructs corresponding to those presented panel A were transfected into COS7 cells and after 24 h expression either 100 μM 2,2'-dipyridyl (DP) or vehicle (H$_2$O) were added to the culture medium and incubated for 6 h before observation. Photographs were taken using a Zeiss fluorescent microscope.

DISCLOSURE OF THE INVENTION

Figure 1:
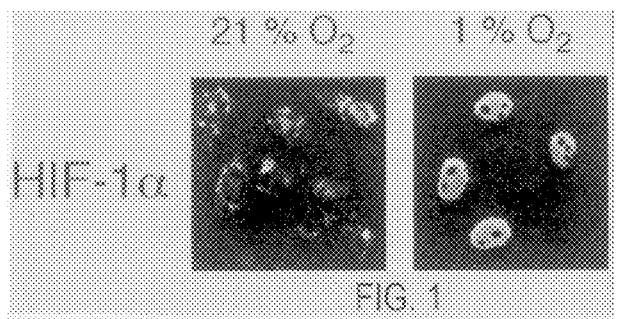
FIG. 1 HIF-1α shows hypoxia-inducible nuclear translocation. COS7 cells were transiently transfected with pCMV-HIF-1α and after 24 h expression incubated for 6 additional h under either normoxic (21% $O_2$) or hypoxic (1% $O_2$) conditions before fixation for immunocytochemistry. Localization of expressed HIF-1α was determined by indirect immunofluorescence using anti-HIF-1α antiserum as described in Materials and Methods.

It has surprisingly been shown that the mechanism of activation of HIF-1α is a multi-step process, which includes hypoxia-dependent nuclear import and activation (derepression) of the transactivation domain, resulting in recruitment of the CBP/p300 coactivator. Inducible nuclear accumulation has been shown to be dependent on a nuclear localization signal (NLS) within the C-terminal end of HIF-1α that also harbors the hypoxia-inducible transactivation domain. Nuclear import of HIF-1α was inhibited by either deletion or a single amino acid substitution within the NLS sequence motif and, within the context of the full-length protein, these mutations also resulted in inhibition of the transactivation activity of HIF-1α and recruitment of CBP. It has further been shown that nuclear localization per se is not sufficient for transcriptional activation, since fusion of HIF-1α to the heterologous GAL4 DNA binding domain generated a protein which showed constitutive nuclear localization but required hypoxic stimuli for function as a CBP-dependent transcription factor.

Moreover, the transcriptional coactivators SRC-1 and TIF2 also support HIF-1α-dependent transcriptional activation. CBP and the SRC-1/TIF2 class of coactivators target both N- and C-terminal transactivation domains of HIF-1α, and are potentiated in their function by the redox regulatory enzyme Ref-1. In fact, Ref-1 physically interacts with HIF-1α under hypoxic conditions. Thus, hypoxia-inducible nuclear import and transactivation by Ref-1-dependent is recruitment of the transcriptional coactivators CBP, SRC-1/TIF2 can be functionally separated from one another and play critical roles in signal transduction by HIF-1α.

Consequently, in a first aspect this invention relates to a method for identifying compounds capable of modulating the function of a functional domain of human HIF-1α, said method comprising (i) contacting a candidate compound with a variant of human HIF-1α, said variant essentially lacking at least one functional domain of human HIF-1α, or having a mutation making at least one functional domain of human HIF-1α essentially inactive, said functional domain or domains being selected from the group consisting of (a) the PAS-B domain located in human HIF-1α between amino acids 178 and 390, (b) the C-terminal nuclear localization sequence (NLS) located in human HIF-1α essentially at amino acids 718 to 721, and (c) the transactivator domain (N-TAD) located in human HIF-1α essentially between amino acids 531 to 584, and (d) the transactivator domain (C-TAD) located in human HIF-1α essentially between amino acids 813 and 826, and (ii) determining the effect of the candidate compound on the said variant.

In one preferred form, the said method comprises (i) contacting a candidate compound with a cell expressing a said variant of human HIF-1α, said variant being conjugated to a molecular probe, and (ii) detecting the localization of the said molecular probe within the cell. The said molecular probe is preferably a fluorescent probe, such as the *Aequeora victoria* Green Fluorescent Protein, or a variant thereof. A change in the relative fluorescence of the nucleus to the cytoplasm is then indicative for a compound capable of modulating the function of the said functional domain.

In another preferred form of the invention, the said variant of human HIF-1α is regulating the activity of a reporter gene; a change in the activity of the reporter gene being indicative of a compound capable of modulating the function of the said functional domain. The HIF-1α variant can e.g. be fused to the DNA binding domain of GAL4, and the cells expressing the HIF-1α variant will contain a GAL4 response element operatively linked to a reporter gene. Alternatively, the variant of human HIF-1α can be fused to the *Aequeora victoria* Green Fluorescent Protein, and the cells expressing the HIF-1α variant could suitably contain an erythropoietin hypoxia response element operatively linked to a reporter gene, e.g. a firefly luciferase gene.

The method according to the invention can suitably be carried out in the presence of a transcriptional coactivator, in particular one or more of the transcriptional coactivators designated SRC-1, TIF2 or CBP. When a transcriptional coactivator is present, the method according to the invention can suitably be carried out in the further presence of the redox regulatory protein designated Ref-1.

When the said functional domain of human HIF-1α is the PAS-B domain, the said variant of human HIF-1α can e.g. be HIF-1α/1–74 (SEQ ID NO: 2); HIF-1α/1–245 (SEQ ID NO: 3); HIF-1α/Δ178–390 (SEQ ID NO: 6); HIF-1α/331–641 (SEQ ID NO: 7); HIF-1α/526–641 (SEQ ID NO: 8); HIF-1α/526–813 (SEQ ID NO: 9); or HIF-1α/526–826 (SEQ ID NO: 10).

When the said functional domain of human HIF-1α is the C-terminal nuclear localization sequence (NLS) domain, the said variant of human HIF-1α can e.g. be HIF-1α/1–74 (SEQ ID NO: 2); HIF-1α/1–245 (SEQ ID NO: 3); HIF-1α/1–330 (SEQ ID NO: 4); HIF-1α/1–652 (SEQ ID NO: 5); HIF-1α/331–441 (SEQ ID NO: 7); or HIF-1α/526–641 (SEQ ID NO: 8).

When the said functional domain of human HIF-1α is the transactivator domain (N-TAD), located in human HIF-1α essentially between amino acids 531 to 584, the said variant of human HIF-1α can e.g. be HIF-1α/1–74 (SEQ ID NO: 2); HIF-1α/1–245 (SEQ ID NO: 3); HIF-1α/1–330 (SEQ ID NO: 4); HIF-1α/776–826 (SEQ ID NO: 14); or HIF-1α/776–813 (SEQ ID NO: 15).

When the said functional domain of human HIF-1α is the transactivator domain (C-TAD), located in human HIF-1α essentially between amino acids 813 and 826, the said variant of human HIF-1α can e.g. be HIF-1α/1–74 (SEQ ID NO: 2); HIF-1α/1–245 (SEQ ID NO: 3); HIF-1α/1–330 (SEQ ID NO: 4); HIF-1α/1–652 (SEQ ID NO: 5); HIF-1α/331–641 (SEQ ID NO: 7); HIF-1α/526–641 (SEQ ID NO: 8); HIF-1α/526–813 (SEQ ID NO: 9); HIF-1α/1–813 (SEQ ID NO: 12); HIF-1α/531–584 (SEQ ID NO: 13); HIF-1α/776–813 (SEQ ID NO: 15).

In a further aspect, the invention provides an isolated variant of human HIF-1α, said variant being selected from the group consisting of HIF-1α/1–74 (SEQ ID NO: 2); HIF-1α/1–245 (SEQ ID NO: 3); HIF-1α/1–330 (SEQ ID NO: 4); HIF-1α/1–652 (SEQ ID NO: 5); HIF-1α/Δ178–390 (SEQ ID NO: 6); HIF-1α/331–641 (SEQ ID NO: 7); HIF- 1α/526–641 (SEQ ID NO: 8); HIF-1α/526–813 (SEQ ID NO: 9); HIF-1α/526–826 (SEQ ID NO: 10); HIF-1α/71–826 (SEQ ID NO: 11); HIF-1α/1–813 (SEQ ID NO: 12), HIF-1α/531–584 (SEQ ID NO: 13); HIF-1α/776–826 (SEQ ID NO: 14); and HIF-1α/776–813 (SEQ ID NO: 15).

EXAMPLES

1. HIF-1α Shows Hypoxia-inducible Nuclear Import

To study the intracellular localization of HIF-1α we transiently transfected simian COS7 cells with a CMV promoter-driven HIF-1α expression vector. Following 24 h of expression cells were incubated for a further 6 h under either normoxic (21% $O_2$) or hypoxic (1% $O_2$) conditions. Immunostaining with polyclonal anti-HIF-1α antibodies (Kallio et al., 1997) showed HIF-1α immunoreactivity predominantly localized in the cytoplasm of the normoxic cells with some reactivity also detected in the nuclear compartment. Interestingly, exposure of the cells to hypoxia resulted in a very striking nuclear accumulation of HIF-1α with hardly any detectable immunoreactivity remaining in the cytoplasm (FIG. 1).

Figure 2B:
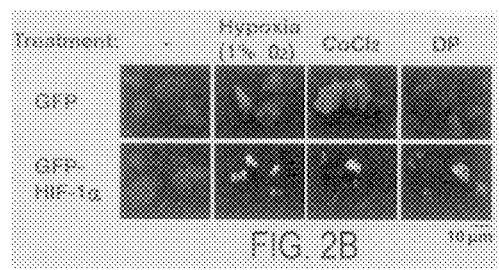
FIG. 2 Hypoxic regulation of nuclear translocation by GFP-HIF-1α. (A) Schematic representation showing the GFP and GFP-HIF-1α protein constructs. For HIF-1α, location of the basic helix-loop-helix and PAS (Per/Arnt/Sim) domains is also indicated. (B) Hypoxia and hypoxia-mimicking chemicals induce rapid nuclear translocation of GFP-HIF-1α fusion proteins. COS7 cells were transiently transfected with either GFP or of GFP-HIF-1α expression vectors and after 24 h expression induced for 6 h either with 1% $O_2$, 100 μM $CoCl_2$ or with 100 μM 2,2'-dipyridyl (DP) before microscopy. (C) Endogenous HIF-1α, but not GFP-HIF-1α, protein levels are upregulated by hypoxic induction. COS7 cells were transfected with nonfusion GFP expression vector (lanes 1 and 2) or with GFP-HIF-1α (lanes 3 and 4). Following transfection cells were exposed to 21% or 1% (hypoxia) oxygen for 30 h as indicated by − and +signs. Whole cell extracts were prepared as described in Materials and Methods, and 50 μg aliquots were analyzed by SDS-polyacrylamide gel electrophoresis and immunoblotting using anti-HIF-1α antiserum. GFP-HIF-1α protein is indicated by an arrowhead, whereas the asterisk denotes endogenous HIF-1α immunoreactivity. The positions of the molecular weight markers (in kDa) are indicated on the left. (D) Time-dependent nuclear translocation of GFP-HIF-1α. COS7 cells were transfected as in panel A with GFP-HIF-1α expression vectors and induced with 100 μM 2,2'-dipyridyl. Photographs were taken at the indicated timepoints after induction. (E) Graph presentation of the nuclear entry of GFP-HIF-1α. Cells transfected with GFP-HIF-1α were induced with 100 μM 2,2'-dipyridyl and the a total of 250 cells were analyzed for distribution of the fluorescence at fixed timepoints. N (%) is the percentage of cells showing exclusively nuclear fluorescence.

To further investigate the mechanism of activation of HIF-1α and its subcellular localization in living cells we constructed a vector carrying an in-frame GFP-fusion of full-length HIF-1α (schematically shown in FIG. 2A) expressed under the control of the CMV promoter. Following transient transfection of COS7 cells with either the parental GFP construct or the chimeric GFP-HIF-1α construct, fluorescence was observed in about 20–30% of the cells, reflecting the level of transfection efficiency. The fluorescence of GFP alone was uniformly localized throughout the cell, and hypoxic treatment had no effect either on the intensity or the subcellular distribution of fluorescence activity (FIG. 2B). Transient expression of the GFP-HIF-1α construct in normoxic cells resulted in signal mimicking the picture observed with GFP alone, thus showing fluorescence activity throughout the cell (FIG. 2B).

For quantitative purposes, 200–300 fluorescent cells were routinely analyzed for compartmentalization of HIF-1α and subdivided into four categories (Ylikomi et al. (1992) EMBO J. 11, 3681–3694): N, cells containing exclusively nuclear fluorescence; N>C, cells in which the nuclear fluorescence dominates over cytoplasmic fluorescence; N=C, cells having equal distribution of fluorescence in the cytoplasmic and nuclear compartments; and N<C, cells in which the intensity of fluorescence in the cytoplasm exceeds that in the nucleus. A percentage of cells belonging to each category is indicated in Table I. Under normoxic conditions 65% of cells transiently expressing the GFP-HIF-1α construct belonged to category N=C; whereas a limited number the cells (8%) showed preferential nuclear compartmentalization of HIF-1α (category N). In contrast, exposure of the cells to hypoxia (1% $O_2$) resulted in almost complete nuclear accumulation of GFP-HIF-1α (FIG. 2B), where 90% of the transfected cells exhibited exclusively nuclear fluorescence (category N; Table I). Moreover, treatment of the cells with chemicals known to mimic hypoxic induction of target gene expression (Wenger and Gassmann (1997) Biol. Chem. 378, 609–616) and induction of HIF-1α DNA binding activity (Wang et al. (1995) Proc. Natl. Acad. Sci. USA 92, 5510–5514; Gradin et al. (1996) Mol. Cell Biol. 16, 5221–5231) e.g. $CoCl_2$ or the iron chelator 2,2'-dipyridyl (DP), also induced nuclear import of GFP-HIF-1α. In fact, we did not observe any quantitative or qualitative differences in the potencies of any of these treatments to induce nuclear translocation of HIF-1α (FIG. 2B).

Figure 2C:
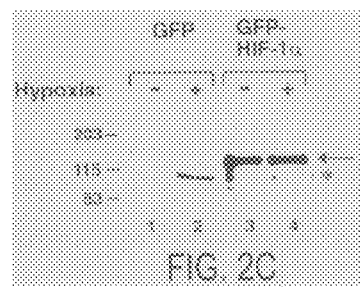

We and others have recently demonstrated that a critical mechanism in activation of HIF-1α in response to hypoxia is upregulation of HIF-1α protein levels. This response depends upon the stabilization of HIF-1α protein rather than being the result of increased HIF-1α mRNA expression levels or enhanced translation of HIF-1α mRNA (Huang et al. (1996) J. Biol. Chem. 271, 32253–32259; Kallio et al. (1997) Proc. Natl. Acad. Sci. USA 94, 5667–5672; Salceda and Caro (1997) J. Biol. Chem. 272, 22642–22647). Since we did not detect any significant alterations in the relative intensity in fluorescence by GFP-HIF-1α upon hypoxic stimulation (FIG. 2B), we examined by immunoblot analysis the expression levels of GFP-HIF-1α protein in transiently transfected normoxic cells or cells exposed to hypoxia (1% oxygen) following transfection. As shown in FIG. 2C, no increase was detected in the expression levels of GFP-HIF-1α protein in hypoxic cells as compared to normoxic ones (compare lanes 3 and 4). As a reference, however, endogenous HIF-1α levels were upregulated in extracts from cells exposed to hypoxia (FIG. 2C, lanes 2 and 4, endogenous HIF-1α indicated by a star). In fact, as documented earlier (Kallio et al., supra), due to rapid turn-over endogenous HIF-1α is virtually undetectable in extracts from normoxic cells (FIG. 2C, lanes 1 and 3). These experiments therefore demonstrate that GFP efficiently stabilized HIF-1α in normoxic cells, and that the use of GFP fusion proteins enabled us to bypass the early level in regulation of HIF-1α function, and allowed us to study intracellular compartmentalization of HIF-1α without the added complexity of regulation of protein turn-over.

Figure 2D:
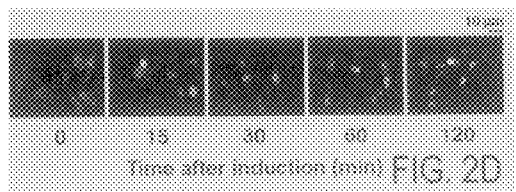
Figure 2A:
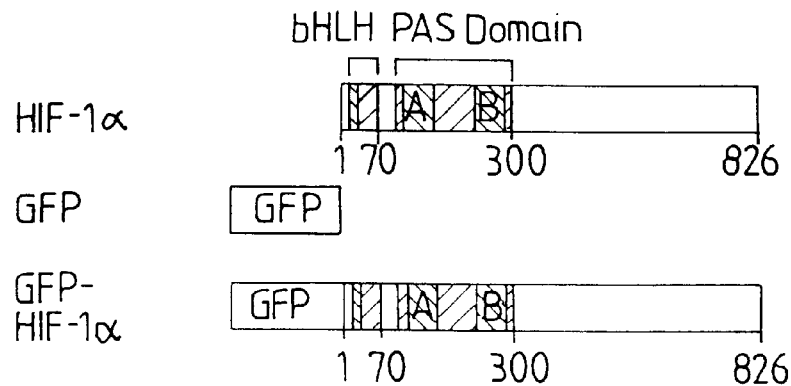
Figure 2E:
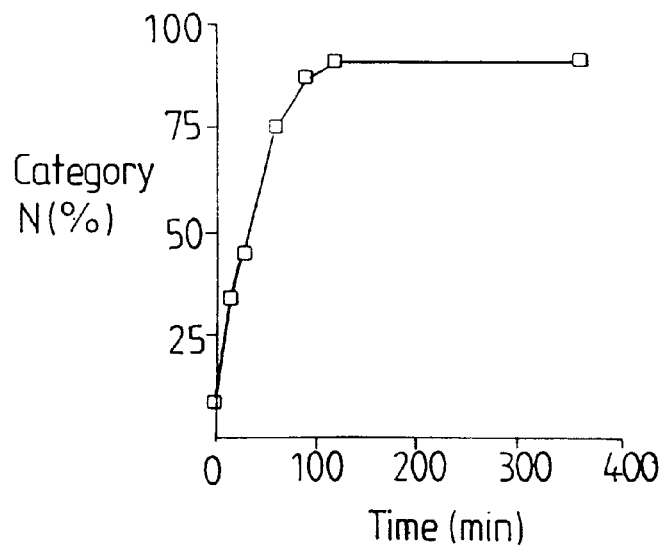

Upon exposure of COS7 cells to hypoxia or hypoxia-mimicking chemicals such as 2,2'-dipyridyl the kinetics of nuclear accumulation of GFP-HIF-1α showed half-maximal time of nuclear transfer of about 30 min (FIGS. 2D and E) and a complete nuclear import of the protein following 1 h of exposure at +37° C. These kinetics are quite slow in comparison to other transcription factors which show signal-inducible nuclear import. For instance, a significantly more rapid time course of inducible nuclear transport has been reported for the glucocorticoid receptor (Ogawa et al. (1995) Proc. Natl. Acad. Sci. USA 92, 11899–11903; Carey et al. (1996) J. Cell Biol. 133, 985–996; Htun et al. (1996) Proc. Natl. Acad. Sci. USA 93, 4845–4850), a ligand-dependent transcription factor showing hormone-dependent nuclear translocation.

Figure 3B:
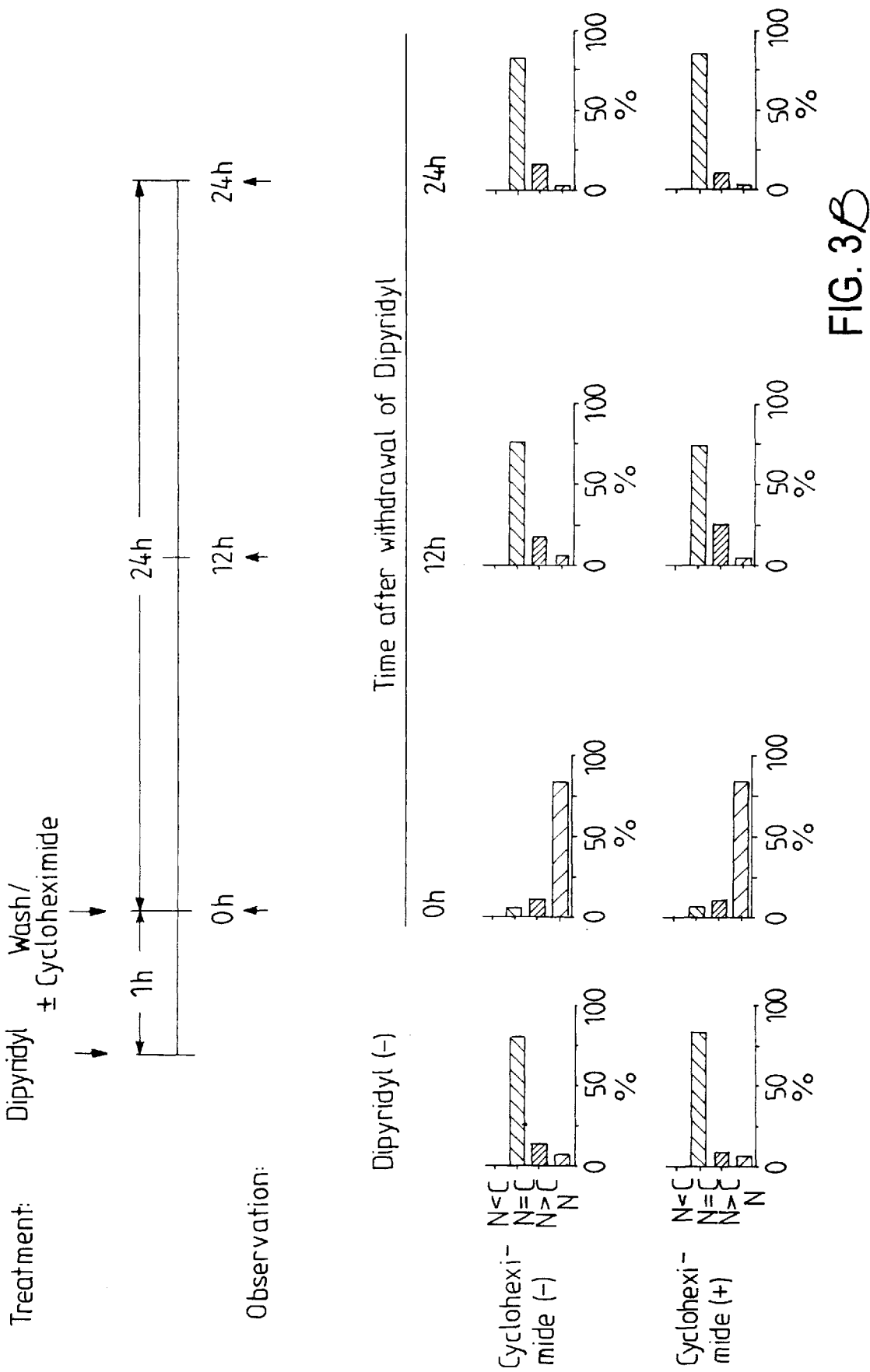
FIG. 3 Nuclear export of HIF-1α upon withdrawal of hypoxic signal. (A) Outline of the experimental strategy. COS7 cells were transfected with the GFP-HIF-1α expression vector (6 μg/60-mm dish) for 6 h and grown under atmospheric oxygen for 12, whereafter they were either induced with 100 μM 2,2'-dipyridyl or left uninduced for 1 h. Subsequently 2,2'-dipyridyl was withdrawn by change of medium and washing of the cells, and the cells were thereafter incubated in the absence (−) or presence (+) of 25 μM cycloheximide for 24 h. During this time period cells were observed microscopically at different timepoints as indicated by arrows. For each timepoint, a total of 200 cells was counted and analyzed. (B) HIF-1α is redistributed from the nucleus upon withdrawal of 2,2'-dipyridyl. The subcellular distribution of GFP-HIF-1α is shown at different timepoints following withdrawal. The percentage of cells belonging to each category in indicated (for classification, see Table I). For reference the intracellular distribution of GFP-HIF-1α prior to induction with 2,2'-dipyridyl is also shown.

To further characterize hypoxic signal-dependent regulation of compartmentalization of HIF-1α in living cells we next asked whether return of the cells to normoxia following exposure to hypoxia or withdrawal of hypoxia-mimicking chemicals would affect the intracellular localization of GFP-HIF-1α. To this end we first induced nuclear import of GFP-HIF-1α (84% of cells belonging to category N) by treatment of transfected cells with 2,2'-dipyridyl for 1 h. Subsequently 2,2'-dipyridyl was withdrawn by washing of the cells in medium, and the cells were further incubated at normal levels of atmospheric oxygen tension (schematically represented in FIG. 3A). After 12 h of incubation under normoxic conditions, 75% of the transfected cells showed an equal distribution of GFP-HIF-1α in both the nuclear and cytoplasmic compartments (category C=N), and the exclusively nuclear pool of GFP-HIF-1α (category N) had been reduced from 84% to 5% (FIG. 3B). An almost identical distribution of GFP-HIF-1α was observed after 24 h of withdrawal of 2,2'-dipyridyl (FIG. 3B). Thus, hypoxia-induced nuclear retention of GFP-HIF-1α could be reversed following withdrawal of the hypoxic signal. To address the question whether this reversion could depend on inefficient nuclear import of de novo synthesized GFP-HIF-1α, we also performed this withdrawal experiment in the presence of the protein synthesis inhibitor cycloheximide. Under these conditions, reversal of 2,2'-dipyridyl-induced nuclear retention of GFP-HIF-1α was very similar to that observed in the absence of cycloheximide, i.e. reduction of the nuclear pool (category N) of GFP-HIF-1α from 84% to 3%, concomitant with an increase of the pool of GFP-HIF-1α belonging to category C=N from 6% to 82% (FIG. 3B), indicative of an export of the originally nuclear pool of protein.

2. Role of the PAS Domain in Regulation of Nuclear Import of HIF-1α

Figure 5A:
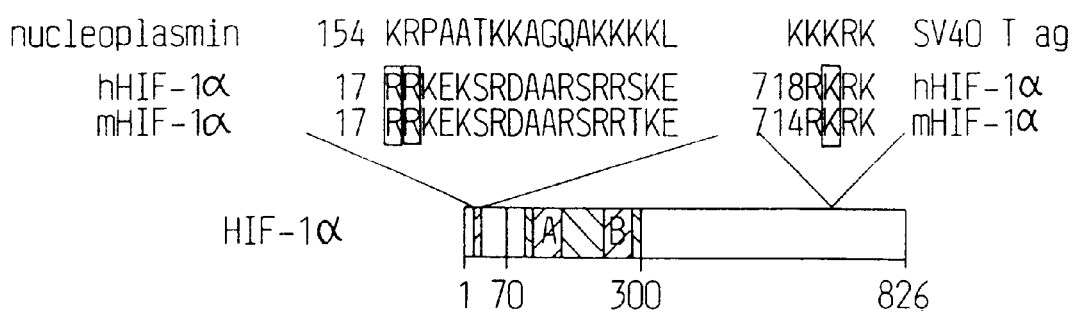
FIG. 5 Identification of a hypoxia-inducible NLS motif within the C-terminus of HIF-1α. (A) Analysis of human (h) and mouse (m) HIF-1α sequences reveals two conserved nuclear localization signal (NLS) motifs. The N-terminal NLS motif is showing homology to the bipartite-like NLS sequence as exemplified by *X. laevis* nucleoplasmin, whereas the C-terminal NLS motif is related to SV40 large T antigen-like NLS sequence. (B) Effect of point mutagenesis within the NLS motifs on nuclear accumulation of GFP-HIF-1α fusion proteins. COS7 cells were transfected with various GFP-HIF-1α fusion protein expression plasmids carrying either wild-type or mutated HIF-1α NLS sequences. The mutations were either single (Arg to Ala) or double (Arg to Gly) amino acid exchanges at residues 17 and 18, or a single amino acid exchange (Lys to Thr) at codon 719, respectively. After transfection, cells were treated with 100 μM 2,2'-dipyridyl or with vehicle only for 6 h before fluorescence microscopy.

In order to identify the structural motif(s) involved in nuclear import of HIF-1α, we generated a number of expression vectors containing GFP fused to different subdomains of HIF-1α (schematically represented in FIG. 4A). Following transient expression of these constructs in COS7 cells, the cells were either exposed to 2,2'-dipyridyl or left untreated for 6 h, and subsequently analyzed for compartmentalization of the fusion proteins. As shown in FIG. 4B, fusion of the most N-terminal region of HIF-1α spanning the bHLH motif (aa 1–74; SEQ ID NO: 2) to GFP resulted in a predominantly nuclear accumulation of the protein under normoxic conditions. Moreover, nuclear accumulation of this protein was not altered by exposure to 2,2'-dipyridyl (FIG. 4B and Table I). It has previously been demonstrated that the basic DNA binding region within the bHLH domain is sufficient for nuclear localization of the bHLH-PAS transcription factors Arnt and the dioxin (aryl hydrocarbon) receptor (Eguchi et al. (1997) J. Biol. Chem. 272, 17640–17647; Ikuta et al. (1998) J. Biol. Chem. 273, 2895–2904). Thus, in analogy to these proteins, the isolated bHLH domain of HIF-1α mediated constitutive nuclear import. In excellent agreement with these observations, HIF-1α contains between aa 17–33 a bipartite NLS motif similar to that of *Xenopus laevis* nucleoplasmin (Dingwall et al. (1987) EMBO J. 6, 69–74) (FIG. 5A).

Interestingly, extension of the N-terminal portion of HIF-1α to fragments spanning, in addition to the bHLH domain, the PAS-A motif (HIF-1α/1–245; FIG. 4A; SEQ ID NO: 3) or the entire PAS domain (HIF-1α/1–330; SEQ ID NO: 4) generated GFP-fusion proteins where the constitutive NLS motif within the bHLH domain appeared to be masked. Unlike HIF-1α/1–74, these two proteins showed significant cytoplasmic fluorescence activity (FIG. 4B) which was detectable both under normoxic and hypoxic conditions and generated a score of 26 and 95% of the transfected cells within the category N=C, respectively (Table I). These results suggest that the PAS domain harbors a structure repressing nuclear import mediated by the NLS motif within the bHLH domain of HIF-1α, resulting in cytoplasmic retention of the protein. In strong support of this of this model, GFP fusion protein containing a HIF-1α mutant lacking a significant portion of the PAS domain, most notably the PAS B motif (HIF-1α/Δ178–390; FIG. 4A; SEQ ID NO: 6), fluorescence was predominantly nuclear already under normoxic conditions (FIG. 4B), yielding a nuclear score (categories N and N>C) of 80% (Table I). Exposure to hypoxia had no further effect on the subcellular localization of GFP-HIF-1α/Δ178–390 (FIG. 4B; Table I). Thus, removal of the inhibitory motif or cytoplasmic retention signal within the PAS domain of HIF-1α resulted in uncoupling of the protein from hypoxia regulation.

3. Identification of an NLS Motif within the C-terminus of HIF-1α

To further investigate which structural motifs mediated hypoxia-inducible nuclear compartmentalization of HIF-1α and to map the functional architecture of HIF-1α we next examined the intracellular localization of GFP fusion proteins containing HIF-1α structures located C-terminally of the PAS domain, i.e. the fusion proteins GFP-HIF-1α/331–641 and GFP-HIF-1α/526–641 (FIG. 4A) (The sequences of HIF-1α/331–641 and HIF-1α/526–641 are shown as SEQ ID NOS: 7 and 8, respectively). These two proteins demonstrated fluorescence both in the cytoplasm and nucleus (100% of the cells belonging to category N=C; Table I) that was unaltered by hypoxia and thus indistinguishable from the properties of the parental GFP protein (FIG. 4B). Consistent with our observations above that the PAS domain represses nuclear import mediated by the constitutive NLS motif within the N-terminal bHLH domain, a fusion protein containing the bHLH/PAS domain and the C-terminal portion of HIF-1α extending to aa 652 (GFP-HIF-1α/1–652; The sequence of HIF-1α/1–652 is shown as SEQ ID NO: 5) showed exclusively cytoplasmic/perinuclear localization (FIG. 4B) with 100% of the transfected cells falling into category N<C (Table I). Importantly, unlike GFP fused to full-length HIF-1α, GFP-HIF-1α/1–652 was non-responsive to hypoxia or dipyridyl treatment and thus unable to undergo nuclear translocation under these conditions, indicating that the very C-terminus of HIF-1α harbors sequences that may function as important determinants for inducible nuclear accumulation. Strikingly, fusion to GFP of the C-terminal portion of HIF-1α spanning amino acids 526–826 (SEQ ID NO: 10) generated a protein demonstrating exclusively nuclear fluorescence (FIG. 4B). Thus, as shown schematically in FIG. 5A HIF-1α contains a second NLS motif within this region of the protein. In fact, sequence analysis indicated the presence within this portion of HIF-1α at amino acids 718 a bona fide SV40 Large T antigen type of NLS motif characterized by a single cluster of four consecutive basic residues, RKRK. This motif is also conserved in the mouse HIF-1α protein (FIG. 5A). Nuclear fluorescence by GFP-HIF-1α/526–826 containing this motif was detected both under normoxic and hypoxic conditions, demonstrating that the domain of HIF-1α harboring this second, SV40 Large T antigen type of NLS motif mediated constitutive nuclear import (FIG. 4B; Table I).

4. A Single Amino Acid Mutation in the C-terminal NLS Motif Abolishes Hypoxia-inducible Nuclear Import of Full Length HIF-1α

Figure 5B:
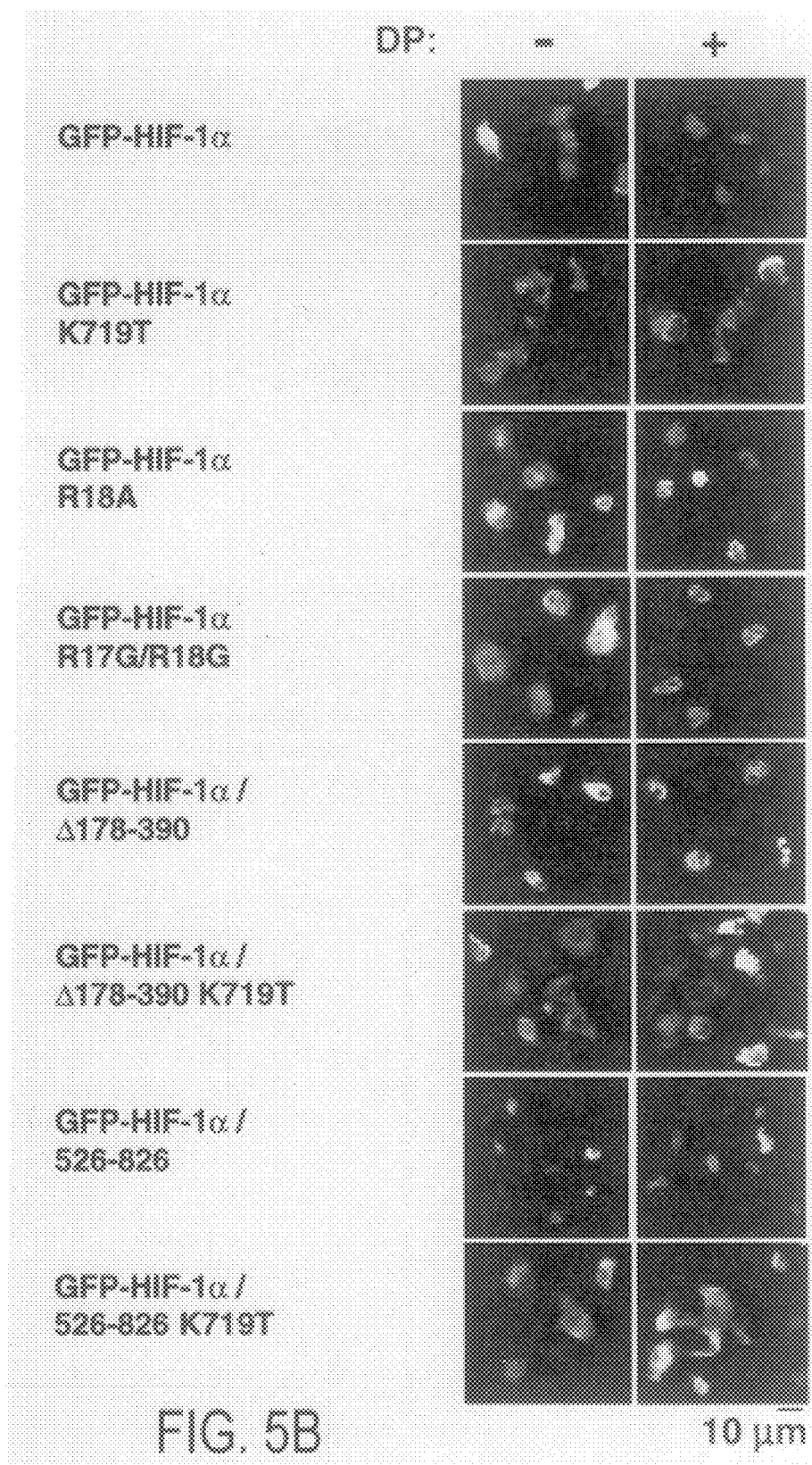

Given the presence of a second NLS motif within the C terminus of HIF-1α and the inability of the N-terminal portions of HIF-1α to show hypoxia-inducible nuclear accumulation we investigated the role of the N- and C-terminal NLS motifs in inducible nuclear import by mutation analysis. To this end we introduced within the context of full length HIF-1α either single or or double exchanges of the N-terminal Arg residues of the N-terminal bipartite NLS motifs of HIF-1α, or mutated Lys 719 to Thr within the C-terminal NLS motif (FIG. 5A). As shown in FIG. 5B, point mutations of the N-terminal NLS motif did not affect hypoxia-inducible nuclear translocation of HIF-1α. Importantly, however, the single amino acid exchange within the C-terminal NLS motif resulted in a dramatic reduction of the ability of the HIF-1α to accumulate in the nucleus in response to hypoxia (FIG. 5B) yielding a score of predominantly cytoplasmatically localized protein (category N<C) of 96% during normoxia versus 81% under hypoxic conditions (Table II). In conclusion, these experiments demonstrate that the C-terminal NLS motif of HIF-1α mediates hypoxia-inducible nuclear import of the protein.

Introduction of the identical amino acid exchange within the C-terminal NLS motif severely impaired the constitutive nuclear accumulation of the isolated C-terminus of HIF-1α fused to GFP (compare GFP-HIF-1α/526–826 in Table I to GFP-HIF-1α/526–826 K719T in Table II). Thus, whereas the isolated C-terminal NLS motif mediates constitutive activity, it shows hypoxia-inducible activity within the context of full length HIF-1α. Since GFP-HIF-1α/Δ178–390 lacking a major part of the PAS domain, most notably the PAS-B motif (FIG. 4A), shows constitutive nuclear localization (FIGS. 4B and 5B), it appears that the C-terminal NLS motif functions in close partnership with the PAS domain in mediating the inducible nuclear import response. To test this notion, we also introduced the single amino acid exchange of Lys 719 to Thr into the PAS B deletion mutant GFP-HIF-1α/Δ178–390. Interestingly, this double mutant failed to show any significant nuclear import under either normoxic or hypoxic conditions (FIG. 5B), generating scores of protein predominantly localized in the cytoplasmic compartment (category N<C) of 82 and 85%, respectively (Table II). In summary, these results demonstrate that the N-terminal basic region does not function as an NLS motif in the context of the full-length protein and that the C-terminal NLS motif plays a critical in mediating inducible nuclear import of HIF-1α.

Figure 6D:
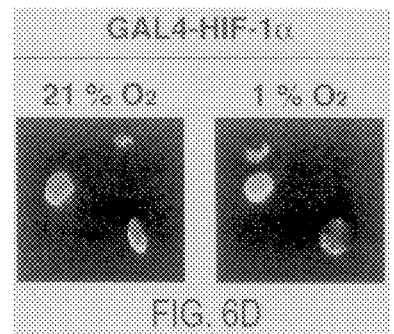
FIG. 6 Overlapping C-terminal structures mediate inducible nuclear translocation and transcriptional activation by HIF-1α. (A) Transcriptional activation of a hypoxia responsive gene by GFP-HIF-1α chimeras. COS7 cells were cotransfected either with GFP or GFP-HIF-1α fusion constructs together with a hypoxia responsive reporter gene (HRE-luc). Six h after transfection cells were exposed either to 21% or 1% O$_2$ for 30 h before harvest. Normalized reporter gene activities are expressed relative to that of nonfusion GFP in normoxia. The results of two independent experiments performed in triplicates +/−SEM are shown. (B) Transcriptional activation by GFP-HIF-1α is Arnt-dependent. COS7 cells were cotransfected either with GFP or GFP-HIF-1α expression vectors and a hypoxia responsive reporter gene (HRE-luc in the presence of either wild-type Arnt or a dominant negative Arnt mutant, ArntΔb, lacking the DNA binding b domain. Cells were exposed for 21% or 1% O$_2$ for 30 h before harvest and reporter gene assays. Normalized reporter gene activities are expressed relative to that of nonfusion GFP in normoxia. The results of two independent experiments performed in triplicates +/−SEM are shown. (C) Functional analysis of GAL4-HIF-1α fusion proteins. The same subregions of HIF-1α as characterized in panel A were fused to the GAL4 DNA binding domain (GAL4 DBD) and transfected into COS7 cells together with a reporter plasmid expressing the luciferase gene driven by the thymidine kinase minimal promoter under the control of five copies of GAL4 binding sites. Cells were exposed for 21% or 1% O$_2$ for 30 h before harvest and reporter gene assays. Normalized reporter gene activities are expressed relative to that of the nonfusion GAL4 DBD in normoxia. The results of three independent experiments performed in triplicates +/−SEM are shown. (D) Constitutive nuclear localization of GAL4-HIF-1α. COS7 cells were transiently transfected with pCMX-GAL4-HIF-1α and after 24 h expression exposed to normoxic (21% O$_2$) or hypoxic (1% O$_2$) conditions for 6h before immunocytochemistry. Indirect immunofluorescence of expressed GAL4-HIF-1α fusion protein was conducted with anti-GAL4-DBD antiserum, biotinylated anti-rabbit Ig antibody, and Texas Red conjugated with streptoavidin.
Figure 6B:
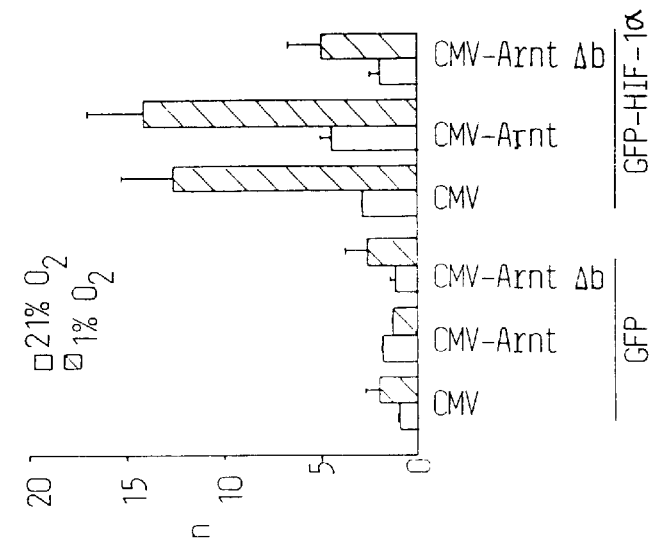
Figure 6A:
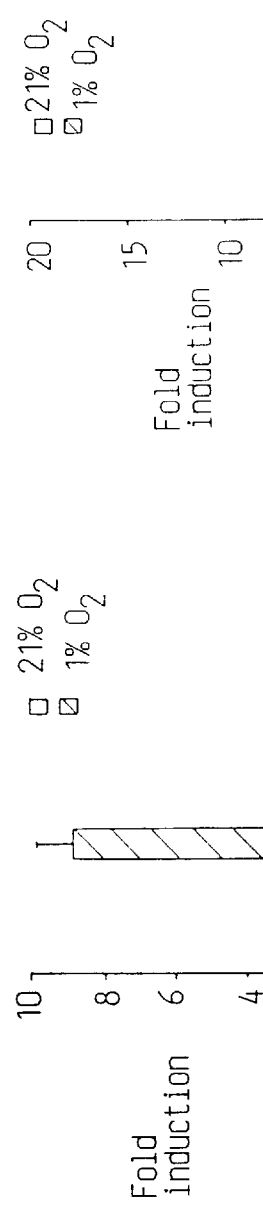

5. Evidence for a Multi-step Activation Pathway of HIF-1α in Response to Hypoxia We next examined the ability of GFP-HIF-1α fusion proteins in functional cotransfection assays where GFP-HIF-1α expression vectors were introduced into COS7 cells together with a hypoxia-responsive gene reporter construct carrying three tandem copies of the erythropoietin hypoxia responsive element (HRE) in front of the Herpes simplex thymidine kinase promoter and the luciferase gene. Reporter gene activity was not significantly altered by hypoxic treatment (1% $O_2$; FIG. 6A) or incubation with 2,2'-dipyridyl (data not shown) either in the absence of coexpressed proteins or in the presence of transiently expressed parental GFP, most probably due to low levels of endogenous HIF-1α activity in COS7 cells. However, coexpression of GFP-HIF-1α resulted in stimulation (about 2-fold) of reporter gene activity already at normoxia, possibly due to stabilization of HIF-1α levels by the GFP moiety and, as described above, a small but detectable pool of HIF-1α localized in the nucleus under these conditions. This reporter gene activity was further stimulated about 4-fold by hypoxia (FIG. 6A). In control experiments, transient expression of wild-type HIF-1α also yielded a similar pattern of reporter gene activation, albeit with a slightly lower potency generating about a 2-fold activation response upon exposure to hypoxia. Thus, fusion of GFP to the immediate proximity of the N-terminal basic (DNA binding) region did not interfere with transcriptional activation. In fact, stabilization of the fusion protein (FIG. 2C) by the GFP moiety may rather have enhanced the potency of the activation response produced by HIF-1α. As expected, in this functional assay GFP-HIF-1α fusion proteins lacking the DNA binding bHLH region (GFP-HIF-1α/331–641, GFP-HIF-1α/526–641 and GFP-HIF-1α/526–826) did not induce any reporter gene activity.

Although ectopic expression of wild-type Arnt did not significantly enhance hypoxia-induced transcriptional activation by GFP-HIF-1α, transient expression of a dominant negative Arnt mutant, ArntΔb, lacking the DNA binding basic (b) domain (Lindebro et al. (1995) EMBO J. 14, 3528–3539), resulted in potent inhibition of the hypoxia-dependent activation response (FIG. 6B). Thus, these results demonstrate that hypoxia-induced transcriptional activation of HRE-driven reporter gene expression by GFP-HIF-1α was critically dependent on interaction with the bHLH-PAS partner factor Arnt. In line with these results the mutant GFP-HIF-1α/Δ178–390 lacking the PAS-B domain, an important dimerization interface with Arnt (Lindebro et al., supra), failed to significantly induce HRE-dependent reporter gene expression in response to hypoxia (FIG. 6A).

Figure 6C:
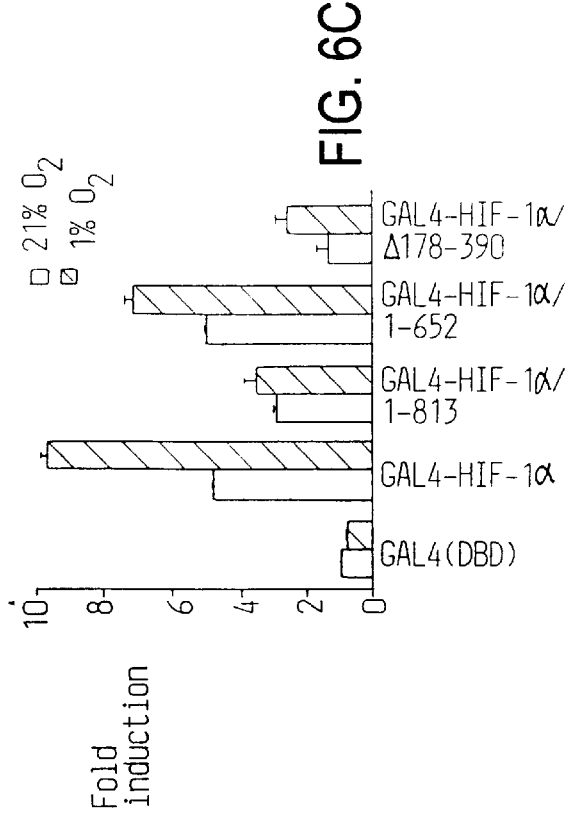

To analyze functional activities of HIF-1α independently of the endogenous DNA binding and dimerization domains and the Arnt partner, we next fused HIF-1α to the heterologous DNA binding domain of GAL4. Functional activity of the fusion protein was monitored in COS7 cells by a cotransfection assay using a reporter gene construct carrying five GAL4 DNA binding elements in front of thymidine kinase promoter and the luciferase gene. Six hours after transfection media was changed, and cells were either left uninduced or exposed to 1% oxygen for 30 h prior to harvest. In the presence of either empty expression vector or a vector expressing the minimal GAL4 DNA binding domain, reporter gene activity was unaltered by reduced oxygen levels. Transient expression of GAL4-HIF-1α at normoxia resulted in moderate (about 4- to 5-fold) reporter gene activation (FIG. 6C). However, when cells were incubated at 1% oxygen (FIG. 6C; or with 100 μM 2,2'-dipyridyl; data not shown), the functional activity of GAL4-HIF-1α was further enhanced about 2-fold, resulting in about 8- to 10-fold stimulation of reporter gene activity over the background levels (FIG. 6C). The GAL4 DNA binding domain is known to harbor an NLS motif capable of taking fusion proteins to the nucleus (Ma and Ptashne (1987) Cell 51, 113–119). We therefore used antibodies directed against the DNA binding domain of GAL4 to examine in both normoxic and hypoxic cells the intracellular localization of the GAL4-HIF-1α fusion protein by immunofluorescence. As shown in FIG. 6D, the GAL 4 DNA binding domain mediated constitutive nuclear localization of the GAL4-HIF-1α fusion protein (FIG. 6D). Given the fact that GAL4-HIF-1α showed hypoxia-inducible functional activity these data establish that inducible nuclear import of HIF-1α does not suffice for transcriptional activation, indicating a multi-step activation pathway HIF-1α upon exposure to hypoxia.

6. Overlapping C-terminal Structures Mediate Inducible Nuclear Translocation and Transcriptional Activation by HIF-1α

Based on deletion analysis HIF-1α has been reported to harbor two transactivation domains (Jiang et al. (1997) J. Biol. Chem. 272, 19253–19260; Pugh et al. (1997) J. Biol. Chem. 272, 11205–11214). Whereas conflicting data exist with regard to hypoxia inducibility of the expression levels of these two domains, the minimal transactivation domains have been mapped to amino acid residues 531–582 and 775–826. Consistent with these observations GFP-HIF-1α fragments lacking transactivation domains but showing constitutive nuclear localization (e.g. GFP-HIF-1α/1–74) did not induce reporter gene activity. In a similar fashion the fusion proteins GFP-HIF-1α/1–245 and GFP-HIF-1α/1–330 were devoid of any functional activity (data not shown). Moreover, transient expression of GFP-HIF-1α/1–652 failed to stimulate HRE-dependent reporter gene activity over background values (FIG. 6A), although this protein contains one of the transactivation domains of HIF-1α, resulting in transcriptional activation when fused to the GAL 4 DNA binding domain (FIG. 6C), and was expressed at levels similar to those of transiently expressed GFP-HIF-1α (data not shown). This result is in excellent agreement with the inability of GFP-HIF-1α/1–652 to enter the cell nucleus (FIG. 4B). In conclusion, these data demonstrate that the inducible nuclear localization and transactivation functions, although contained within the C-terminus of HIF-1α, represent distinct functional entities, which can be separated from one another. This conclusion is further strengthened by the finding that deletion of the 13 most C-terminal amino acid residues from HIF-1α resulted in significant reduction of transcriptional activity, both in the case of GFP-HIF-1α/1–813 and GAL4-HIF-1α/1–813 (FIGS. 6A and 6C), although both of these proteins were capable of entering the nucleus (FIG. 4B and data not shown).

Figure 7A:
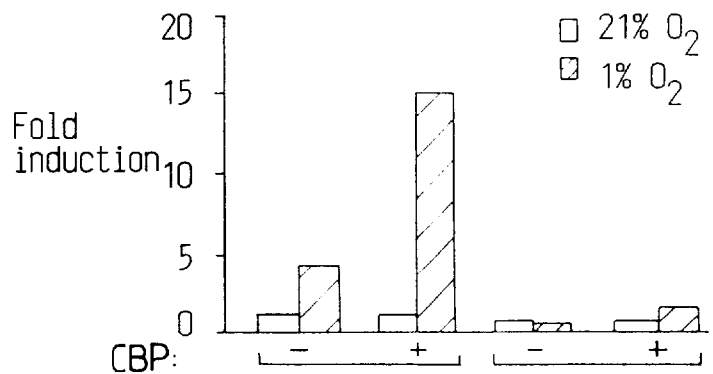
FIG. 7 Hypoxia-dependent recruitment of the CBP coactivator by HIF-1α. (A) Stimulation of hypoxia responsive gene expression by CBP. COS7 cells were cotransfected with either GFP-HIF-1α or GFP-HIF-1α K719T together with HRE-luciferase reporter and Rous sarcoma virus (RSV)-driven CBP expression vector (or empty expression plasmid). Six h after transfection cells were exposed either to 21% or 1% O$_2$ for 30 h before harvesting the cells. Luciferase values were normalized for transfection efficiency by cotransfection of alkaline phosphatase expressing pRSV-AF. The data are expressed relative to that of GFP-HIF-1α in normoxia. (B) NLS mutation eliminating inducible nuclear import does not affect hypoxia dependent recruitment of CBP. GAL4-HIF-1α or GAL4-HIF-1α transactivation domain fusion proteins were transfected into COS7 cells together with a GAL4 responsive reporter plasmid with or without CBP expression plasmid. Cells were exposed for 21% or 1% O$_2$ for 30 h before harvest and reporter gene assays. (C) The C-terminal transactivation domain of HIF-1α is targeted by CBP. GAL4 fusion protein containing the minimal C-terminal transactivation domain (amino acids 776–826) or a deletion mutant thereof were transfected into COS7 cells together with a GAL4 responsive reporter plasmid in the absence or presence of the CBP expression vector. Cells were exposed for 21% or 1% O$_2$ for 30 h before harvest and reporter gene assays. After normalization for transfection efficiency using alkaline phosphatase activity, reporter gene activities are expressed relative to that of GAL4 in normoxia.

7. Transcriptional Activation by HIF-1α-hypoxia-dependent Recruitment of the CBP Coactivator is Functionally Uncoupled from the Inducible NLS Motif The CREB binding protein CBP is a transcriptional coactivator protein known to interact with a number of constitutively active or inducible DNA binding transcription factors including, among others, CREB, c-Fos, c-Jun, various members of the steroid receptor superfamily, and p53 (Shikama et al. (1997) Trends Cell Biol. 7, 230–236). CBP has also been demonstrated to physically associate with HIF-1α and to play a role in hypoxia-dependent transactivation of erythropoietin promoter in Hep3B cells (Arany et al. (1996) Proc. Natl. Acad. Sci. USA 93, 12969–12973). We therefore initially examined the effect of overexpression of CBP on hypoxia-dependent activation by GFP-HIF-1α of the minimal HRE-driven reporter gene. As expected, transient expression of GFP-HIF-1α under hypoxic conditions resulted in about 4- to 5-fold stimulation of the HRE-dependent reporter gene as compared to the activation response observed under normoxic conditions (FIGS. 6A and 7A). Coexpression of GFP-HIF-1α with CBP further enhanced the hypoxia-dependent activation response by about 3-fold, resulting in about 15-fold stimulation of reporter gene activity over the levels observed at normoxia, further establishing that CBP supports transcription by the HIF-1α/Arnt complex (FIG. 7A). In excellent agreement with the data demonstrating that the single-amino acid mutant GFP-HIF-1α K719T protein was unable to undergo inducible nuclear accumulation (FIG. 5B and Table II), GFP-HIF-1α K719T failed to produce the hypoxia-dependent activation response. Moreover, coexpression of GFP-HIF-1α K719T with CBP did not produce any significant stimulation of reporter gene activity under hypoxic conditions, indicating the inability of the nuclear translocation-deficient HIF-1α protein to functionally interact with CBP. As a further control, we examined whether exposure to hypoxia affected the function of other transcription factors that are targets for regulation by CBP. In these experiments, we observed in reporter gene assays no effect of hypoxia on ligand-dependent enhancement by CBP of the functional activity of the retinoic acid receptor α (data not shown), a well-characterized target of CBP (for a review, see Torchia et al. (1998) Curr. Opin. Cell Biol. 10, 373–383).

Figure 7B:
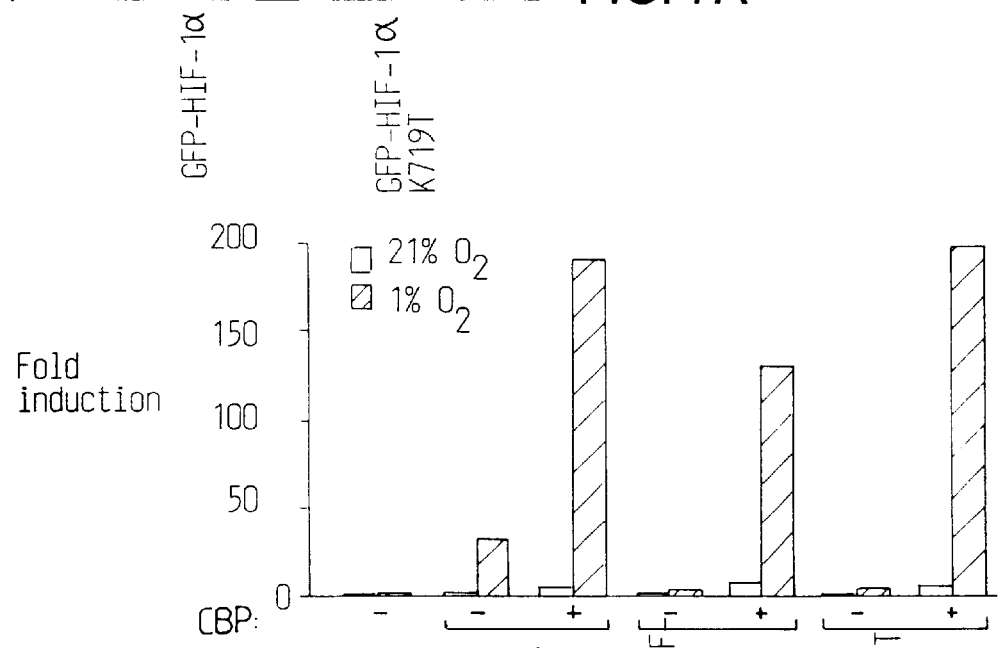
Figure 7C:
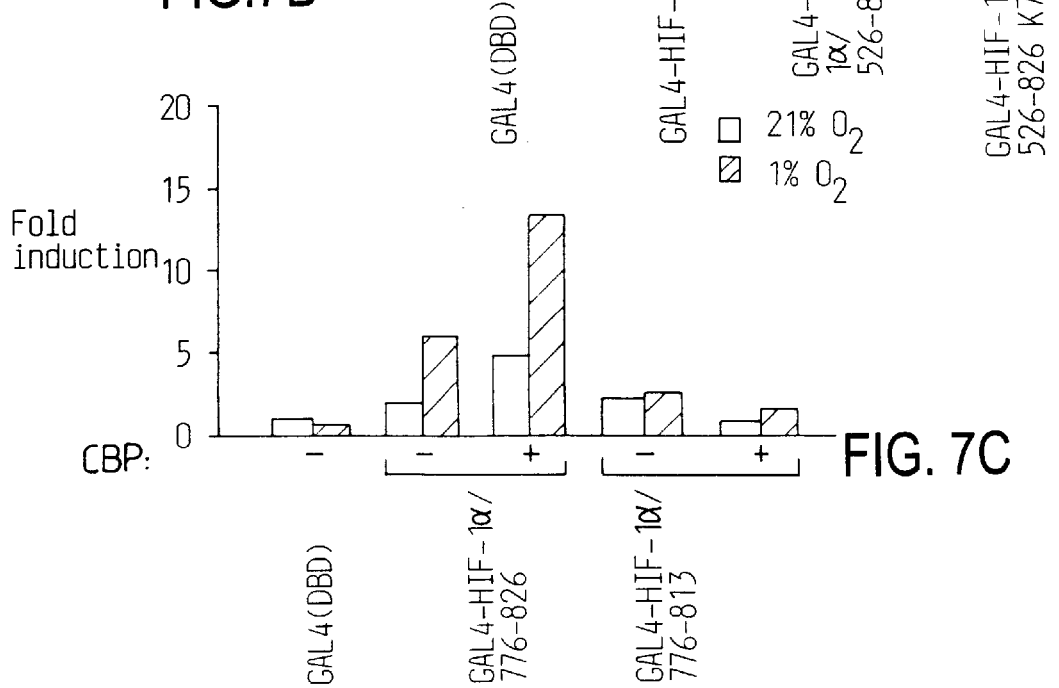

As outlined above, fusion of a HIF-1α to the GAL4 DNA binding domain generated a chimeric protein that produced modest (about 2-fold) hypoxia-dependent activation of reporter gene activity (FIGS. 6C and 7B). In the presence of CBP, however, a further 19-fold stimulation of reporter gene activity was observed under hypoxic conditions, whereas, under normoxic conditions, CBP only slightly (2- to 3-fold) enhanced the activity of GAL4-HIF-1α (FIG. 7B). We next wanted to examine the transactivation capacity of a GAL4 DNA binding domain fusion protein containing the C-terminal subregion 526–826 which harbors both transactivation domains of HIF-1α and showed exclusively nuclear localization when fused to GFP (FIGS. 4B and 5B). This chimeric protein produced modest (about 2-fold) hypoxia-dependent activation of reporter gene activity but was potently enhanced in its inducible activation function following overexpression of CBP (FIG. 7B). Thus, these data demonstrate that the C-terminus of HIF-1α recruits CBP in a hypoxia-dependent manner. Interestingly, CBP was also able to dramatically enhance the activity of the GAL4-HIF-1α/526–826 K719T fusion protein carrying a point mutation in the hypoxia-inducible NLS motif of HIF-1α. In fact, the effect of CBP to support inducible transcription by either GAL4 HIF-1α/526–826 or GAL4-HIF-1α/526–826 K719T was very similar (FIG. 7B), thus demonstrating that inactivation of the hypoxia-inducible NLS motif does not alter the ability of this domain to respond to hypoxia by coactivator recruitment and subsequent transactivation. We also examined the ability of CBP to support the function of the isolated C-terminal transactivation domain (amino acids 776–826) fused to the GAL4 DNA binding domain. Interestingly, whereas this domain mediated activation in the presence of CBP in hypoxic cells, it failed to respond to CBP following deletion of its 13 most C-terminal amino acids (FIG. 7C; compare GAL4-HIF-1α/776–826 to GAL4-HIF-1α/776–813), strongly suggesting that these residues constitute a target for hypoxia-dependent regulation by CBP.

Figure 8:
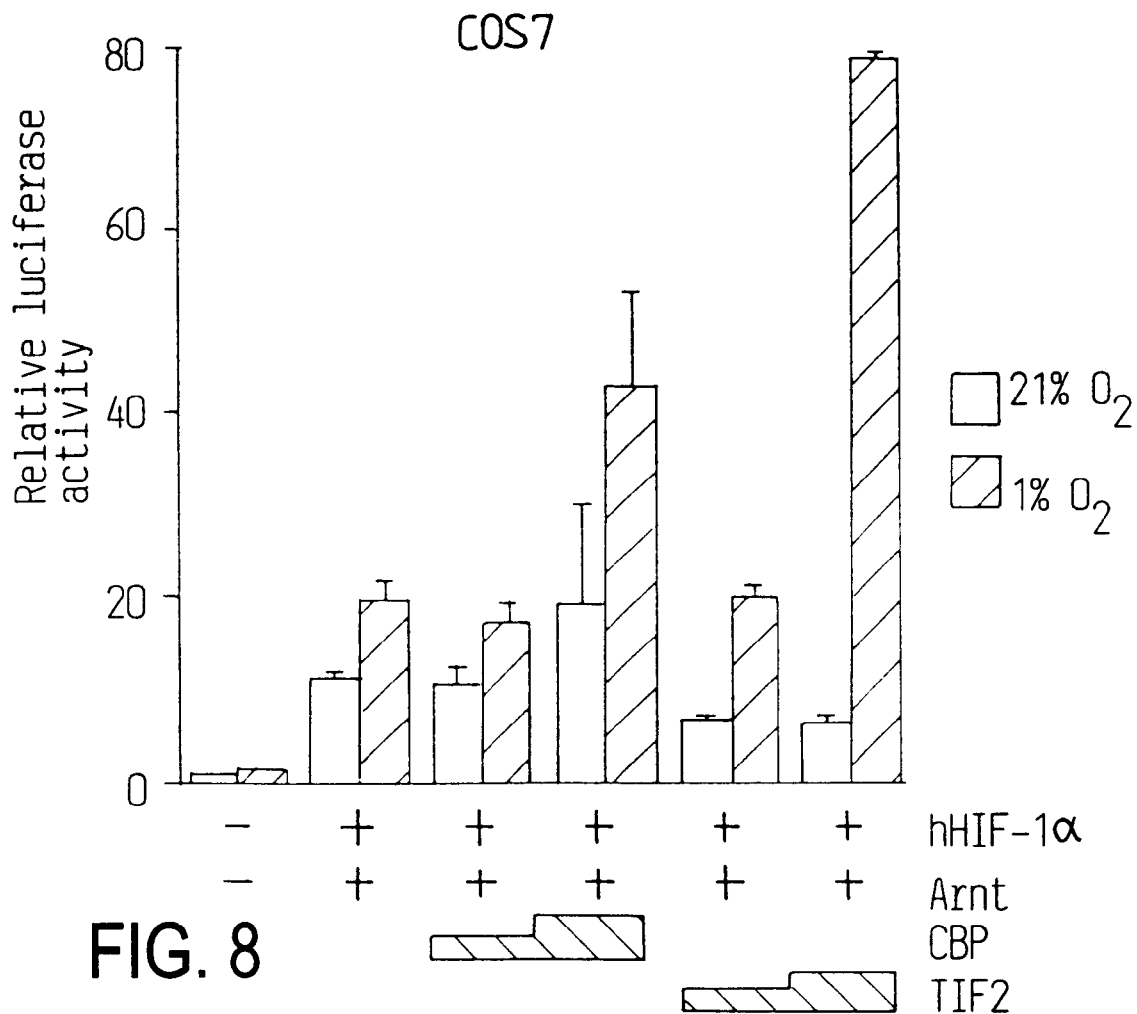
FIG. 8 The transcriptional coactivator TIF2 enhances the HIF-1α-mediated transactivation function and interacts with HIF-1α in vivo. COS7 cells were transiently cotransfected as described in Materials and Methods with 0.5 μg pT81/HRE-Luc reporter construct, hHIF1-α expression vector (pCMV4/HIF-1α, 0.2 μg), Arnt expression vector (pCMV4/Arnt, 0.2 μg) and 0.75–1.5 μg of either TIF2 (pSG5/TIF2) or CBP (Rc/RSV-CBP-HA), as indicated. The total amount of DNA was kept constant by the addition of parental pCMV4 when appropriate. Following transfection cells were incubated either under normoxic (21% $O_2$) or hypoxic conditions (1% $O_2$). Luciferase activities were normalized for transfection efficiency by cotransfection of alkaline phosphatase expressing pRSV-AP. Data are presented as luciferase activity relative to cells transfected with pCMV4 and reporter gene only and incubated at normoxia. Values represent the mean ±S.E. of two independent experiments.

8. TIF2 Enhances HIF-1α Activity and Interacts with the Receptor in a Hypoxia-dependent Manner in Mammalian Cells To gain a better understanding of the mechanism of transcriptional activation by HIF-1α, we tested the effect of transient expression of the transcriptional coactivator TIF2 on the functional activity of HIF-1α. TIF2 belongs to the p160 family of coactivators which have been shown to be required for nuclear receptor-mediated transcriptional activation (Takeshita et al. (1997) J. Biol. Chem. 272, 27629–27634). Transient transfection experiments were initially performed using COS7 cells. As shown in FIG. 8, the reporter gene activity was not significantly altered by hypoxic treatment (1% $O_2$) in the absence of coexpressed proteins, most probably due to the low levels of endogenous HIF-1 activity in COS7 cells (unpublished observations). Upon transient coexpression of HIF-1α and Arnt, pT81/HRE-luc reporter gene activity was stimulated around 10-fold under normoxic conditions, possibly due to a small but detectable pool of HIF-1α localized in the nucleus under these conditions. This reporter gene activity showed a modest increase (~1.5-fold) by hypoxia (FIG. 8). However, as expected, ectopic expression of CBP further enhanced hypoxia-dependent activation by HIF-1α in a dose-dependent manner when compared with hypoxia stimulated activity in the absence of exogenous coactivators (2- to 3-fold). Although expression of CBP slightly stimulated HIF-1α activity already at normoxia, its overall activity was almost entirely dependent on the exposure to hypoxia as has been described previously. The effect was most likely limited to 3-fold due to the large quantities of endogenous CBP already present in the cell prior to transfection. Coexpression of HIF-1α together with TIF2 resulted in potent activation (around 12-fold) of the reporter gene over the levels observed at normoxia, thereby establishing that both TIF2 and CBP support transcription by the HIF-1α/Arnt complex (FIG. 8). In conclusion, TIF-2 which was originally identified as a coactivator supporting hormone-dependent transcriptional activation by members of the steroid hormone receptor family also functions as a conditionally regulated coactivator in hypoxia-dependent transcriptional activation by the HIF-1α/Arnt complex.

In response to hypoxia, HIF-1α is imported to the nucleus and shows a strictly nuclear localization. To characterize the mechanism of TIF2-dependent enhancement of transcriptional activation by HIF-1α in living cells we next asked whether overexpression of TIF2 would affect the intracellular localization of HIF-1α. To this end we transiently transfected COS7 cells with an expression vector encoding an in-frame fusion of green fluorescent protein (GFP) with full-length HIF-1α. As shown above, fluorescence of this GFP-HIF-1α construct was uniformly distributed throughout the cell under normoxic conditions, and treatment of the transfected cells with the hypoxia-mimicking agent 2,2'-dipyridyl for 2 h led to a complete nuclear accumulation of the GFP-HIF-1α protein. Transient expression of the TIF2 coactivator protein in the presence of GFP-HIF-1α had no effect either on the intensity or the subcellular distribution of fluorescence activity at normoxia. However, upon exposure of cells coexpressing GFP-HIF-1α and TIF2 to 2,2'-dipyridyl, GFP-HIF-1α-dependent fluorescence activity was detected in dot-like structures throughout the nucleus. It has previously been described that TIF2 is a nuclear protein mainly associated with such dot-like discrete bodies within nucleus (Voegel et al. (1998) EMBO J. 17, 507–519). These observations strongly suggest that TIF-2 induced relocalization of GFP-HIF-1α within the nucleus, indicating that GFP-HIF-1α and TIF2 interacted with one another in vivo, and that the dot-like fluorescence pattern might represent transcriptionally active chromatin.

As described above, return of cells to normoxia following exposure to hypoxia or withdrawal of hypoxia-mimicking chemicals results in an export of the nuclear pool of HIF-1α. In order to address whether the interaction between GFP-HIF-1α and TIF2 in vivo would be dependent on the hypoxic stimulus we therefore initially exposed the transfected cells to 2,2'-dipyridyl and then further incubated them at normal levels of atmospheric oxygen tension after withdrawal of 2,2'-dipyridyl by washing of the cells in medium. As expected, after 24 h of incubation under normoxic conditions, a distribution of GFP-HIF-1α in both the nuclear and cytoplasmic compartments was observed that was indistinguishable from the distribution of fluorescence activity prior to exposure to the hypoxic signal. Transient expression of TIF2 did not induce any quantitative or qualitative differences in the export of GFP-HIF-1α, demonstrating that the hypoxia-induced nuclear relocalization of HIF-1α by TIF2 could be reversed following withdrawal of the hypoxic signal.

9. Regulation of the Hypoxia-inducible Transactivation Function of HIF-1α by SRC-1

Figure 9A:
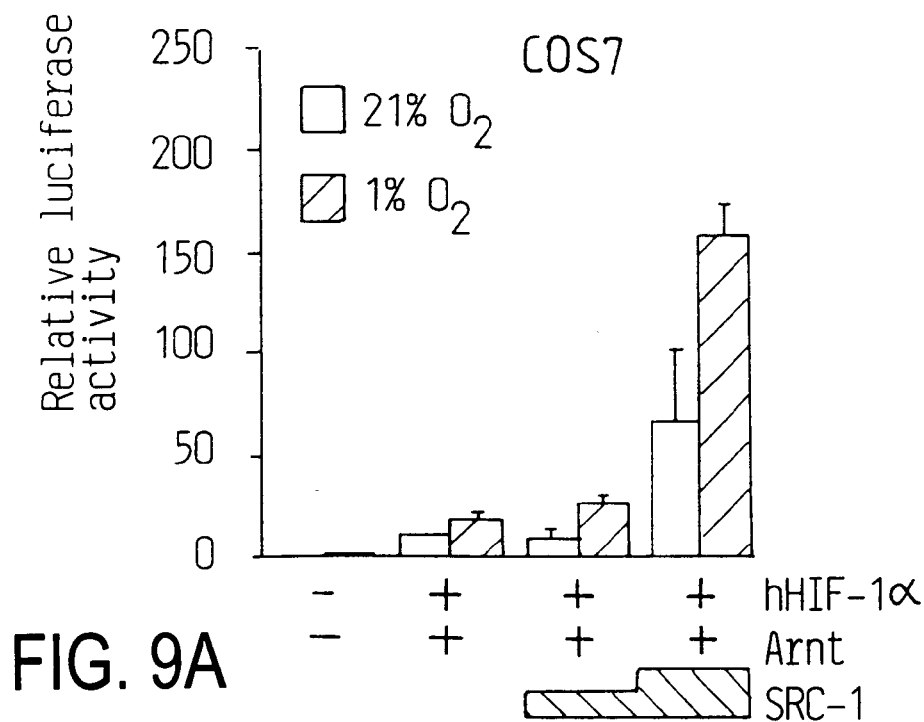
FIG. 9 The transcriptional coactivator SRC-1 stimulates HIF-1α activity in a hypoxia-dependent manner and interacts in vitro with HIF-1α. (A) COS7 and (B) human embryonic kidney 293 cells were cotransfected with pT81/HRE-Luc (0.5 μg), 0.2 μg of pCMV4/HIF-1α (hHIF1-α), 0.2 μg of pCMV4/Arnt (Arnt), and 0.75–1.5 μg of SRC-1 (pSG5/SRC-1), as indicated. Six h after transfection cells were exposed to either 21 or 1% $O_2$ for 36 h before harvest. Luciferase values are presented as relative luciferase activity as described in the legend to FIG. 1. The results of three independent experiments performed in duplicate ±S.E. are shown. (C) SRC-1 PAS domain is not required for functional interaction with HIF-1α. (Top) Schematic representation of full-length SRC-1 and SRC-1ΔPAS. (Bottom) pGAL4/HIF 71–826 was cotransfected into COS7 cells together with a reporter plasmid expressing the luciferase gene driven by the thymidine kinase minimal promoter under the control of five copies of GAL4-binding sites, and 1.5 μg of either full-length SRC-1 or a deletion mutant of SRC-1, SRC-1ΔPAS, lacking the PAS domain. Cells were exposed to 21 or 1% $O_2$ for 36 h before harvest and reporter gene assays. Luciferase values are presented as relative luciferase activity as described in the legend to FIG. 1. The results of two independent experiments performed in duplicate +S.E. are shown. (D) In vitro interaction between SRC-1 and HIF-1α. COS7 cells were transfected with 10 μg of the expression plasmid pGST-HIF-1α (GST-HIF) or empty GST expression vector (GST). Cells were exposed to either 100 μM $CoCl_2$ or vehicle ($H_2O$) for 24 h. Cell extracts were prepared and incubated with [$^{35}$S]methionine-labeled in vitro translated SRC-1 protein. The complexes were immobilized on glutathione-agarose beads for 2 h and eluted with the sample buffer by boiling. The eluted material was analyzed on 5% SDS-PAGE and visualized by fluorography. ⅕×Input represents one-fifth of the amount of [$^{35}$S]methionine-labeled SRC-1 used in the binding reactions. Positions of molecular mass markers are shown on the left.
Figure 9B:
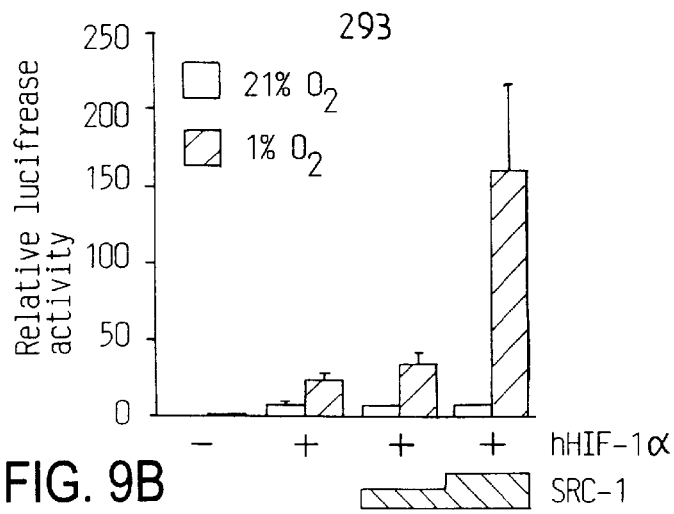

As outlined above, TIF2 belongs to a growing family of the p160 family of coactivators including SRC-1. Both TIF2 and SRC-1 appear to have similar activities as coactivators to enhance the transcriptional potential of many members of the ligand-activated nuclear hormone receptors (Voegel et al., supra). SRC-1 has been demonstrated to directly and constitutively interact with CBP (Yao et al. (1996) Proc. Natl. Acad. Sci. USA 93, 10626–10631). Moreover, in analogy to CBP, SRC-1 has been shown to possess intrinsic histone acetyltransferase activity (Spencer et al. (1997) Nature 389, 194–198). Against this background we also tested the ability of SRC-1 to modulate HIF-1α-dependent transcriptional activation of the minimal HRE-driven reporter gene. In transient transfection experiments using COS7 cells, HRE-dependent reporter gene activity was stimulated from 2- to 8-fold in a dose-dependent manner by SRC-1, as compared with hypoxia-stimulated activity in the absence of exogenous coactivators (FIG. 9A). Transient expression of SRC-1 also enhanced the transcriptional activity of HIF-1α under normoxic conditions, albeit to a lesser extent (around 3-fold; FIG. 9A). Thus, both SRC-1 and TIF2 have similar properties in enhancing the transcriptional potential of HIF-1α. To determine whether regulation of HIF-1α function by members of the p160 family of coactivators was cell type-specific, we next carried out similar transfection experiments in the human 293 embryonic kidney cell line. In these experiments we observed that both SRC-1 (FIG. 9B) and TIF2 (data not shown) can significantly enhance HIF-1α-dependent transcriptional activation in 293 cells.

Figure 9C:
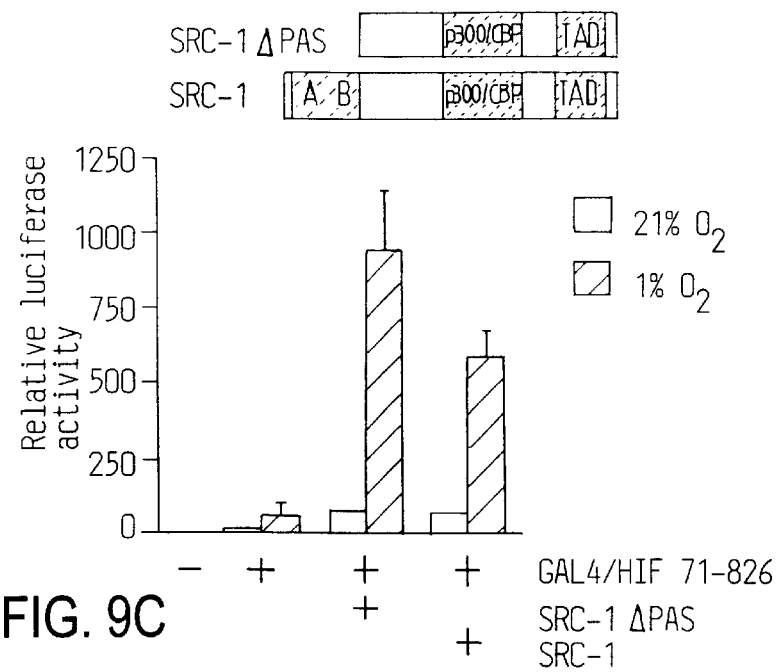

Interestingly, in analogy to HIF-1α, the p160 family of coactivators belongs to the larger family of bHLH/PAS factors (schematically represented in FIG. 9C). SRC-1 was originally cloned as an N-terminally truncated fragment (Oñate et al. (1995) Science 270, 1354–1357), here termed SRC-1ΔPAS (FIG. 9C), lacking the bHLH/PAS motifs. Both the bHLH and PAS domains represent potent protein/protein interaction interfaces, and are critical for dimerization between HIF-1α and Arnt (Gradin et al. (1996) Mol. Cell Biol. 16, 5221–5231; Wang et al. (1995) Proc. Natl. Acad. Sci. USA 92, 5510–5514). To investigate the role of the bHLH/PAS motif of SRC-1 in hypoxia-dependent transactivation by HIF-1α we examined the effect of overexpression of SRC-1ΔPAS or full-length SRC-1 on the transcriptional activity of a fusion protein, GAL4/HIF 71–826, containing the GAL4 DBD fused in frame to a fragment of hHIF-1α spanning amino acids 71–826. Hypoxia-dependent activation of this construct was monitored using a GAL4-responsive reporter gene. As shown in FIG. 9C, the chimeric protein mediated ~4-fold hypoxia-dependent activation of reporter gene activity. In agreement with the effect of SRC-1 on transcriptional activation mediated by the HIF-1α/Arnt complex, coexpression of full-length SRC-1 coactivator further enhanced the activity of GAL4/HIF 71–826 by about 12-fold under hypoxic conditions, resulting in ~45-fold stimulation of the reporter gene over the levels observed at normoxia (FIG. 9C). SRC-1showed no detectable effect on the transcriptional activity by the GAL4 DBD alone (data not shown). These results demonstrate that SRC-1 targets the HIF-1α protein. Next, we examined the effect of the SRC-1ΔPAS mutant on GAL4/HIF 71–826-mediated transactivation. This truncated coactivator fragment showed very similar if not more potent activity than full length SRC-1 in enhancing the hypoxia-dependent activation response (FIG. 9C). Thus, in excellent agreement with the wild-type activity of SRC-1ΔPAS in enhancing steroid hormone receptor-dependent transcriptional regulation (Oñate et al., supra), the bHLH and PAS motifs of SRC-1 were not important to support HIF-1α function.

Figure 9D:
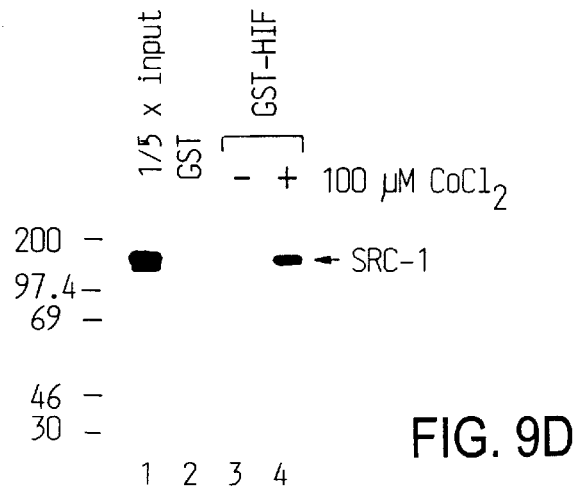

The present experiments indicated the functional importance of both CBP and SRC-1 to enhance the transcriptional potential by HIF-1α in hypoxic cells. CBP has previously been demonstrated to physically interact with HIF-1α (Arany et al. (1995) Nature 374, 81–84). To investigate whether SRC-1 was able to interact with HIF-1α, we performed glutathione-S-transferase (GST) precipitation assays using cell extracts prepared from COS7 cells transiently expressing GST-tagged HIF-1α in the presence and absence of 100 μM $CoCl_2$, a chemical known to mimic hypoxic induction of target gene expression and to activate HIF-1α (Wenger & Gassmann (1997) Biol. Chem. 378, 609–616). This material was subsequently incubated with in vitro translated, [$^{35}$S]labeled SRC-1. As shown in FIG. 9D, in the presence of $CoCl_2$, [$^{35}$S]labeled SRC-1 was specifically retained by the GST-HIF-1α fusion protein immobilized on glutathione-Sepharose beads (lane 4), whereas we observed no significant binding to GST-HIF-1α extracted from non-treated cells (lane 3), or to GST alone (lane 2). Thus, SRC-1 interacted with HIF-1α in a hypoxia-dependent manner in vitro.

10. Role of LXXLL Motifs in HIF-1α-SRC-1 Interaction

Figure 10:
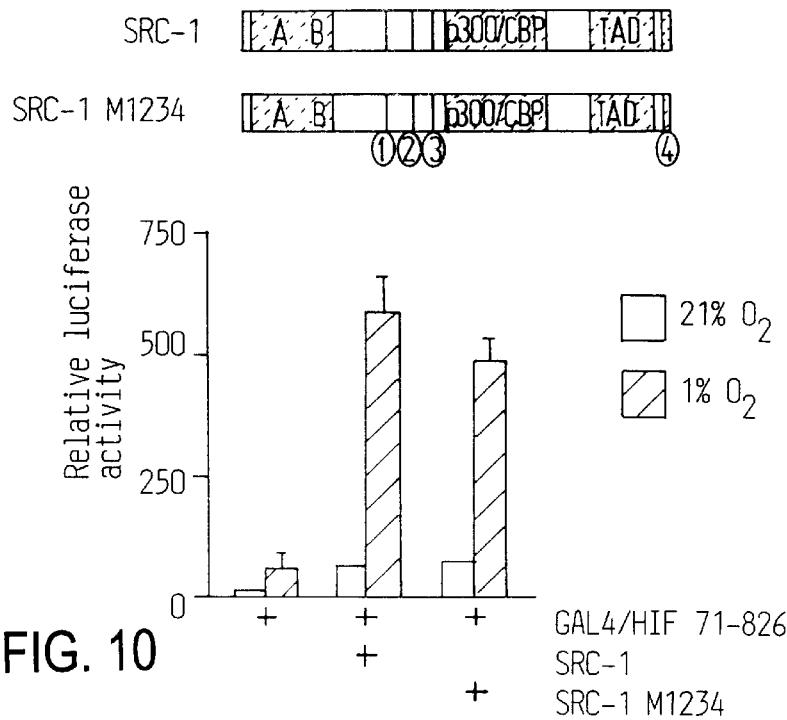
FIG. 10 LXXLL motifs of SRC-1 are not required for HIF-1α-mediated transactivation function and interaction with HIF-1α in vivo. Schematic representation of full-length SRC-1 and mutant SRC-1 M1234. Black bars represent the approximate locations of the LXXLL motifs in the linear SRC-1 sequence; circles with numbers indicate sites of mutation of LXXLL motifs in which conserved leucine residues are replaced by alanines. (Bottom) pGAL4/HIF 71–826 was cotransfected into COS7 cells together with a GAL4-responsive reporter plasmid, and 1.5 μg of either full-length SRC-1 or mutated SRC-1, SRC-1 M1234. Cells were exposed to 21 or 1% $O_2$ for 36 h before harvest and reporter gene assays. Luciferase values are presented as relative luciferase activity as described in the legend to FIG. 1. The results of two independent experiments performed in duplicate ±S.E. are shown.

SRC-1 contains four copies of the short sequence motif, LXXLL. Three of these motifs were identified in the central interaction domain of the protein, and the fourth motif was found in the eight most C-terminal amino acids of human SRC-1 (Heery et al. (1997) Nature 387, 733–736). The LXXLL motifs have been shown to be necessary to mediate the binding of SRC-1 to ligand occupied nuclear receptors. In order to investigate the role of the LXXLL motifs of SRC-1 in hypoxia-dependent transactivation by HIF-1α we compared the abilities of wild-type SRC-1 and SRC-1 M1234, a mutant protein in which the conserved leucine couplets were substituted to alanine at residues 636/7, 693/4, 752/3 and 1438/9, respectively, in transient transfection experiments. As shown in FIG. 10, the mutant protein in which all four functional binding motifs are disabled enhanced the activity of GAL4/HIF 71–826 to the same extent as the wild-type SRC-1 under hypoxic conditions. Moreover, transient expression of either wild-type SRC-1 or SRC-1 M1234 together with GFP-HIF-1α protein in COS7 cells had no effect on the subcellular distribution of fluorescence activity at normoxia. Under hypoxic conditions, SRC-1 induced relocalization of GFP-HIF-1α from a uniform nuclear distribution to discrete dot-like structures within nucleus. This effect was also produced by the mutant SRC-1 M1234 protein, indicating that both proteins interact with HIF-1α in a hypoxia-dependent manner in vivo. Taken together these results suggest that, in contrast to nuclear receptor signaling, the LXXLL motif is not required for HIF-1α-SRC-1 interaction.

11. Definition of the Functional Domains of HIF-1α which Interact with the Coactivators CBP and SRC-1

Figure 11A:
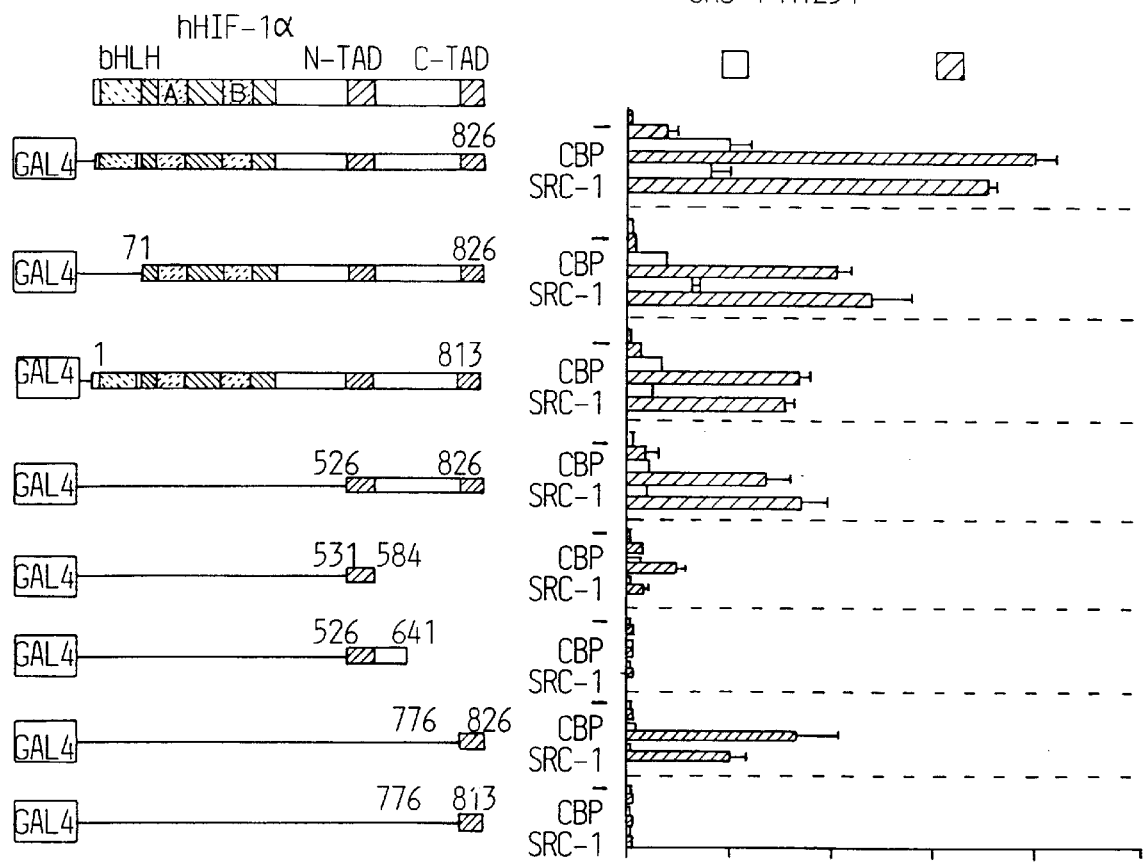
FIG. 11 Definition of HIF-1α structures which are regulated by the CBP and SRC-1 coactivators. (A) Different subregions of HIF-1α were fused to the GAL4 DBD and transfected into COS7 cells together with a GAL4-responsive reporter plasmid in the absence or presence of 1.5 μg of either CBP or SRC-1 expression plasmids. Cells were exposed to 21 or 1% $O_2$ for 36 h before harvest. (B) The C-terminal transactivation domain of Arnt mediates transcriptional activation by CBP and SRC-1. COS7 cells were cotransfected with the indicated GAL4/Arnt fusion proteins and 1.5 μg of CBP or SRC-1 together with a GAL4-responsive reporter plasmid. Six h after transfection cells were exposed to either 21 or 1% $O_2$ for 36 h before harvest and reporter gene assays. (C) HIF-1α prevents Arnt from functionally interacting with CBP and SRC-1. GAL4/Arnt 128–774 and a deletion mutant (GAL4/Arnt 128–603) were transfected into COS7 cells together with 0.2 μg hHIF-1α expression vector and 1.5 μg of CBP and SRC-1, as indicated. Luciferase activity was measured following 36 h of exposure to either 21 or 1% $O_2$. Normalized reporter gene activities are expressed relative to that of non-fusion GAL4 in normoxia. The results of three independent experiments performed in duplicate ±S.E. are shown.

In order to identify HIF-1α structures which could serve as interaction surfaces with the SRC-1 and CBP coactivator proteins, we constructed a series of GAL4 DBD fusion proteins containing HIF-1α fragments of varying length (as schematically represented in FIG. 11A). These constructs were transiently transfected into COS7 cells together with a GAL4 responsive reporter gene. Fusion of full length HIF-1α to the GAL4 DBD produced significant hypoxia-dependent induction of reporter gene activity in the absence of ectopically expressed coactivator proteins (FIG. 11A). Coexpression of either CBP or SRC-1 strongly (around 8- to 10-fold) enhanced the transcriptional potential of HIF-1α in hypoxic cells. These coactivators also increased to a lesser extent the transcriptional activity of GAL4HIF 1–826 under normoxic conditions. Neither CBP nor SRC-1 enhanced the transcriptional activity of the GAL4 DBD alone (data not shown).

GAL4/HIF 71–826, which lacks the bHLH domain of HIF-1α (The amino acid sequence of HIF-1α/71–826 is shown as SEQ ID NO: 11), induced relative luciferase activity about 3.5-fold over background levels (FIG. 11A). In the presence of coexpressed CBP or SRC-1, luciferase activity was induced under hypoxic conditions by GAL4/HIF 71–826 to 30- and 34-fold higher levels, respectively, in comparison with the activity observed at hypoxia in the absence of exogenous coactivators.

We next examined the effect of CBP and SRC-1 on the activity of GAL4 fusion proteins containing sequences lying C-terminally to the DNA binding and dimerization domains of HIF-1α. An hypoxia-inducible activation response was produced by GAL4/HIF 526–826 alone, in excellent agreement with the presence within this HIF-1α fragment of two distinct transactivation domains, delineated N-TAD and C-TAD, respectively, in FIG. 11A, which function in a hypoxia-dependent fashion when fused to the GAL4 DBD (Jiang et al. (1997) J. Biol. Chem. 272, 19253–19260; Pugh et al. (1997) J. Biol. Chem. 11205–11214). Upon transient expression of CBP or SRC-1 the transcriptional activity of GAL4/HIF 526–826 was greatly (about 7- to 9-fold) stimulated, demonstrating that these coactivators target the C-terminus of HIF-1α. Moreover, these results further establish that the enhancing effect of both CBP and SRC-1 on HIF-1α function is independent of the presence of the bHLH and PAS domains of HIF-1α.

To further investigate whether one individual or both transcriptional activation domains of HIF-1α were targeted by the coactivators, we next deleted residues 813–826, a region that is contained within the C-terminal transactivation domain of HIF-1α and has been identified as a point of interaction with CBP (Arany et al. (1996) Proc. Natl. Acad. Sci. USA 93, 12969–12973). Interestingly, GAL4/HIF 1–813 (The amino acid sequence of HIF-1α/1–813 is shown as SEQ ID NO: 12) maintained a hypoxia-inducible response that was significantly enhanced (14- to 13-fold) by overexpression of CBP and SRC-1 (FIG. 11A), indicating that the hypoxia-dependent function of the N-terminal transactivation domain of HIF-1α may also be regulated by the coactivators.

Against this background we were interested in examining the regulatory properties of the individual transactivation domains of HIF-1α. As shown in FIG. 11A, GAL4/HIF 531–584 (The amino acid sequence of HIF-1α/531–584 is shown as SEQ ID NO: 13), a chimeric protein spanning the N-terminal transactivation domain of HIF-1α, showed hypoxia-dependent induction of reporter gene activity, albeit with a lower potency than the constructs spanning both transactivation domains. In the presence of CBP, however, an 11-fold stimulation of reporter gene activity was observed in hypoxic cells, whereas, overexpression of SRC-1 only slightly (1.5-fold) enhanced the activity of GAL4/HIF 531–584 under identical conditions.

We next examined the transactivation capacity of GAL4/HIF 526–641 which harbors both the N-terminal transactivation domain and a structure which has been proposed to function as an inhibitory sequence (Jiang et al., supra). In comparison with GAL4/HIF 531–584, the transcriptional activity of this chimeric protein was greatly reduced and showed complete abrogation of the effect of CBP and SRC-1 on its transactivation function (FIG. 11A), indicating either that an inhibitory region is contained between residues 584 and 641 that may serve to modulate HIF-1α function under certain as yet unidentified conditions, or, alternatively, that the fusion of the N-terminal transactivation domain to this sequence produces a malfolded domain when expressed out of the context of the full length protein.

In comparison, a fusion protein containing the carboxy-terminal transactivation domain of HIF-1α, GAL4/HIF 776–826 (The amino acid sequence of HIF-1α/776–826 is shown as SEQ ID NO: 14), produced a very modest (about 2-fold) hypoxia-dependent induction response. However, its transcriptional activity was dramatically enhanced in the presence of either CBP (29-fold increase) or SRC-1 (17-fold increase). Upon deletion of the 13 most carboxy-terminal amino acids both basal activity and inducible properties of GAL4/HIF 776–813 (The amino acid sequence of HIF-1α/ 776–813 is shown as SEQ ID NO: 15) were completely abrogated independently of the absence or presence of coactivators (FIG. 11A).

Taken together, these results suggest that (i) CBP mediates the hypoxia-inducible transcriptional activation by HIF-1α by targeting both of the transactivation domains of HIF-1α, whereas SRC-1 seems to exert its action mainly through the C-terminal transactivation domain of the receptor; and (ii) the 13 most C-terminal amino acids of HIF-1α are crucial for stimulation of the activity of the C-terminal transactivation domain by CBP or SRC-1. However, in the context of the full-length protein, this C-terminal portion plays only a minor part in determining hypoxia-dependent functional activity in the presence of either CBP or SRC-1.

Figure 11B:
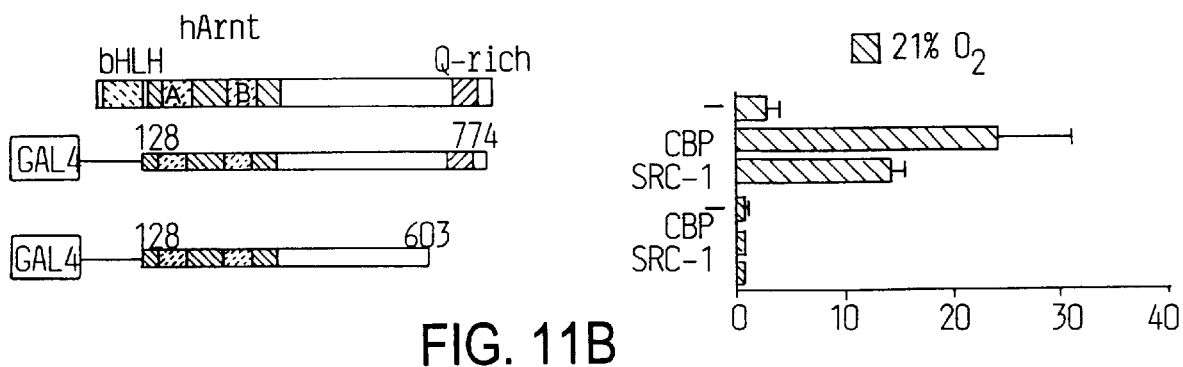
Figure 11C:
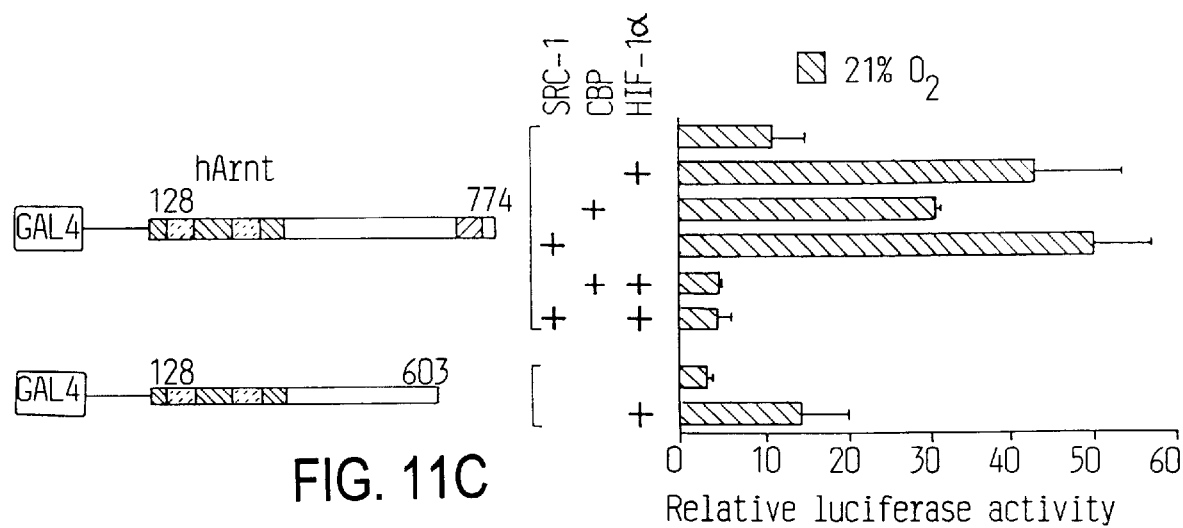

Since Arnt, the functional partner factor of HIF-1α, has recently been shown to interact with CBP/p300 (Kobayashi et al. (1997) J. Biochem. 122, 703–710) we also examined whether SRC-1 might functionally interact with Arnt. In normoxic cells Arnt functions as a constitutively active transcription factor on E box-driven promoters. We transiently expressed in COS7 cells Arnt fused to the GAL4 DBD together with either CBP or SRC-1. In these experiments we observed that constitutive activation of the reporter gene by GAL4/Arnt 128–774 was potently further enhanced by coexpression of CBP or SRC-1 (FIG. 11B). Deletion of the C-terminal transactivation domain of Arnt (schematically represented in FIG. 11B) completely abolished the effect of these coactivators on transcription by GAL4/Arnt 128–603 (FIG. 11B). These observations suggest that the subunits of the HIF-1 heterodimer, HIF-1α and Arnt, interact independently with CBP and SRC-1. Interestingly, whereas Arnt interacted constitutively with CBP and SRC-1, the functional communication of the HIF-1α-Arnt heterodimeric complex with either CBP or SRC-1 was hypoxia-dependent. Thus, dimerization with HIF-1α appears to impose hypoxia-dependent regulation on the ability of Arnt to functionally interact with these coactivator proteins. To further examine this question, we analyzed the effect of overexpression of HIF-1α on the activity of GAL4/Arnt fusion proteins at normoxia. Cotransfection of COS7 cells with HIF-1α and GAL4/Arnt 128–774 resulted in ~4-fold activation of the reporter gene when compared to cells transfected with the GAL4 fusion protein alone (FIG. 11C) probably due to the presence of small amounts of HIF-1α in the nucleus already at normoxia. However, constitutive activation of the reporter gene was completely abolished by coexpression of HIF-1α together with CBP or SRC-1 (FIG. 11C). This effect was indistinguishable from the one observed with GAL4/Arnt 128–603 in the presence of either of the coactivators (FIG. 11B). This deletion mutant, however, when cotransfected with HIF-1α resulted in further ~5-fold stimulation of reporter gene activity (FIG. 11C), in agreement with its ability to functionally interact with HIF-1α via the PAS domain. These results are consistent with the model that dimerization with HIF-1α impairs the ability of Arnt to functionally interacting with CBP or SRC-1. However, the mechanism of this putative negative regulatory effect of HIF-1α needs to be further investigated.

12. SRC-1 and CBP Act Synergistically to Enhance HIF-1α-dependent Transcription

Figure 12A:
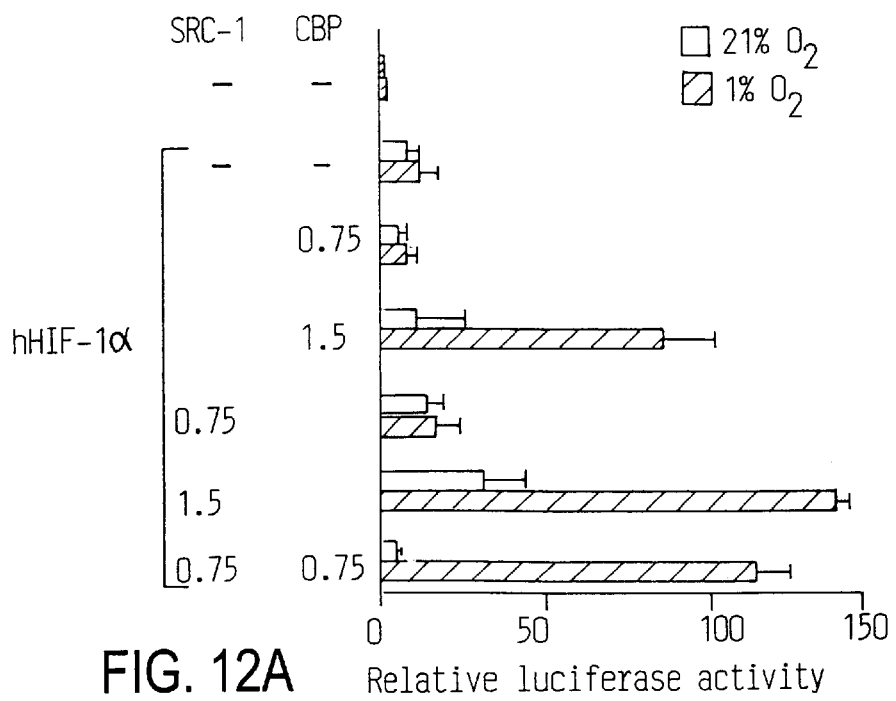
FIG. 12 CBP and SRC-1 cooperatively enhance HIF-1α-mediated transcriptional activation. (A) COS7 cells were transiently cotransfected with pCMV4/HIF-1α and 0.75–1.5 μg of SRC-1 and/or 0.75–1.5 μg of CBP expression plasmids together with a hypoxia-responsive reporter gene (pT81/HRE-Luc) and subsequently exposed to 21 or 1% $O_2$. Luciferase values are presented as relative luciferase activity as described in the legend to FIG. 1. The results of three independent experiments performed in duplicate ±S.E. are shown. (B) Cooperative activation by CBP and SRC-1 of GAL4/HIF-1α fusion proteins. COS7 cells were cotransfected with GAL4/HIF-1α fusion constructs together with a GAL4-responsive reporter plasmid in the absence or presence of CBP and/or SRC-1, as indicated (in μg). Cells were exposed to 21 or 1% $O_2$ before harvest. After normalization for transfection efficiency using alkaline phosphatase activity, reporter gene activities are expressed as relative to that of GAL4 in normoxia. The results of two independent experiments performed in duplicate ±S.E. are shown. (C) p300 protein stimulates the activity of the two minimal transactivation domains of HIF-1α in a hypoxia-dependent manner. (Right Panel) Schematic representation of full-length p300 (pCMVβ-p300-HA) and p300Δ (pCMVβ-p300Δ1254–1376) (Left Panel) The two minimal transactivation domains of HIF-1α were fused to GAL4 DBD and transfected into COS7 cells together with a GAL4-responsive reporter plasmid in the absence or presence of p300, p300Δ and/or SRC-1 expression vectors, as indicated. Cells were exposed to 21 or 1% $O_2$ before harvest. Normalized reporter gene activities are expressed as relative to that of GAL4 in normoxia. The results of a representative experiment performed in duplicate are shown.

The ability of either CBP or SRC-1 to enhance the transcriptional activity of HIF-1α prompted us to investigate the effect of coexpression of both coactivators on HIF-1α function. We initially investigated the effects of transient expression of SRC-1 and CBP individually and in combination with one another on hypoxia-dependent activation by HIF-1α of a minimal hypoxia response element-driven reporter gene. As observed in FIGS. 9A and 2B, the effect of SRC-1 on HIF-1α-dependent activation of the reporter gene was strictly dose-dependent in COS7 and 293 cells, respectively. For instance, at a low concentration of SRC-1 expression vector (0.75 μg), no significant effect on HIF-1α-dependent activation of the reporter gene was detected (FIG. 9A; 9B; 12A). In a similar fashion, an identically low concentration of CBP expression vector produced no enhancement of the transactivation function of HIF-1α (FIG. 12A). Under all these conditions, poor hypoxia-dependent inducibility of the reporter gene was observed. However, a potent, hypoxia-dependent activation response can be reconstituted upon transient coexpression of the SRC-1 and CBP at doses which yielded no significant effect individually (FIG. 12A), indicating strong synergy between these two coactivators in enhancing HIF-1α function.

To further substantiate this synergistic effect, we next examined the transactivation potential of a number of GAL4 DBD fusion proteins containing distinct subregions of HIF-1α. Low concentrations of SRC-1 and CBP produced modest stimulation of the transcriptional activity by GAL4/HIF 71–826 spanning HIF-1α lacking the N-terminal bHLH domain (FIG. 12B). In contrast, coexpression of SRC-1 and CBP generated strong enhancement of the GAL4/HIF 71–826-mediated activation response in hypoxic cells. This effect was more than additive relative to the effects detected in the presence of CBP or SRC-1 alone, and it was also observed using the GAL4/HIF 526–826 fusion protein which contains both the N-terminal and C-terminal transactivation domains of HIF-1α (FIG. 12B). Moreover, coexpression of low concentrations of SRC-1 and CBP potently stimulated hypoxia-inducible transcriptional activation by the individual transactivation domains of HIF-1α contained within GAL4/HIF 531–584 and GAL4/HIF 776–826, respectively. These results are in excellent agreement with the data demonstrating that the two transactivation domains of HIF-1α independently can functionally interact with either SRC-1 or CBP (FIG. 11A). These data also are consistent with the notion that CBP and SRC-1 constitutively interact with one another, and, in analogy to the mechanism of transcriptional activation by members of the steroid hormone receptor family, that recruitment of both coactivators may be necessary to trigger the full activity of HIF-1α in hypoxic cells. It remains to be established whether the recruitment of both of these classes of coactivators to HIF-1α occurs simultaneously or in a temporally regulated fashion. Furthermore it is presently unclear whether CBP, SRC-1 or both coactivators provide the physical contact points with the transactivation domains of HIF-1α upon hypoxic activation. Interestingly, the functional interaction between HIF-1α and the two coactivator proteins was synergistic when both transactivation domains of HIF-1α were contained within the analyzed GAL4-HIF-1α fusion proteins. In contrast, GAL4 fusion proteins spanning the isolated transactivation domains showed an additive mode of regulation in the presence of both SRC-1 and CBP, strongly suggesting that synergistic regulation by these two coactivators may require the presence and integrity of both transactivation domains of HIF-1α.

CBP and p300 are closely related proteins that exhibit strong sequence similarity and similar functions with respect to their roles as coactivators (Arany et al. (1994) Cell 77, 799–800). In analogy to CBP, p300 enhanced in the presence of SRC-1 hypoxia-dependent transcriptional activation of reporter genes by GAL4 fusion proteins containing either one of the two individual transactivation domains of HIF-1α (FIG. 12C). As observed in experiments using CBP (FIG. 12B), the CBP/p300 and SRC-1 classes of coactivators produced together rather modest (3- to 4-fold) hypoxic activation of the N-terminal transactivation domain located between residues 531 and 584 of HIF-1α (FIG. 12C), whereas, in the presence of SRC-1, CBP or p300 more potently (around 11-fold) stimulated hypoxic activation by the C-terminal transactivation domain of HIF-1α (FIG. 12C).

Although the mechanism of action of the CBP/p300 class of coactivators remains largely unclear, recent observations have suggested that these proteins contribute to transcriptional regulation not only by acting as simple adaptors between DNA binding factors and transcription initiation factors but also by harboring intrinsic histone acetyltransferase activity, linking their effect to regulation of chromatin structure and/or function (Korzus et al. (1998) Science 279, 703–707). To investigate the potential role of the acetyltransferase activity of p300 in supporting HIF-1α-dependent transcription, we transfected COS7 cells with a p300 deletion mutant, p300ΔHAT, lacking the histone acetyltransferase (HAT) domain which is centrally located in the protein (schematically represented in the right panel of FIG. 12C). In the absence of SRC-1, transient expression of p300ΔHAT resulted in only very moderate (2-fold) stimulation of the hypoxia-dependent activation response produced by GAL4/HIF 531–584 containing the N-terminal transactivation domain of HIF-1α, whereas it did not produce any significant effect on the hypoxia-induced transcriptional activity of GAL4/HIF 776–826 spanning the minimal C-terminal transactivation domain (FIG. 12C). In the presence of SRC-1, p300ΔHAT enhanced reporter gene activation, most notably when coexpressed in hypoxic cells together with GAL4/HIF 776–826 containing the C-terminal transactivation domain of HIF-1α. However, p300ΔHAT was about 2-fold less potent than wild-type p300 in producing this response (FIG. 12C), indicating that the acetyltransferase catalytic activity of p300 may contribute to trigger the full activity of the HIF-1α-mediated transcriptional activation response. However, given the observed synergy between CBP/p300 and SRC-1 in enhancing activation potency by HIF-1α, and the fact that SRC-1 also harbors intrinsic histone acetyltransferase activity (Spencer et al. (1997) Nature 389, 194–198), the effect of the deletion of the acetyltransferase domain of p300 may be masked by corresponding activities of CBP-associated proteins, possibly that of SRC-1 itself.

13. Ref-1 Potentiates HIF-1α Function in the Presence of CBP and SRC-1

Figure 13A:
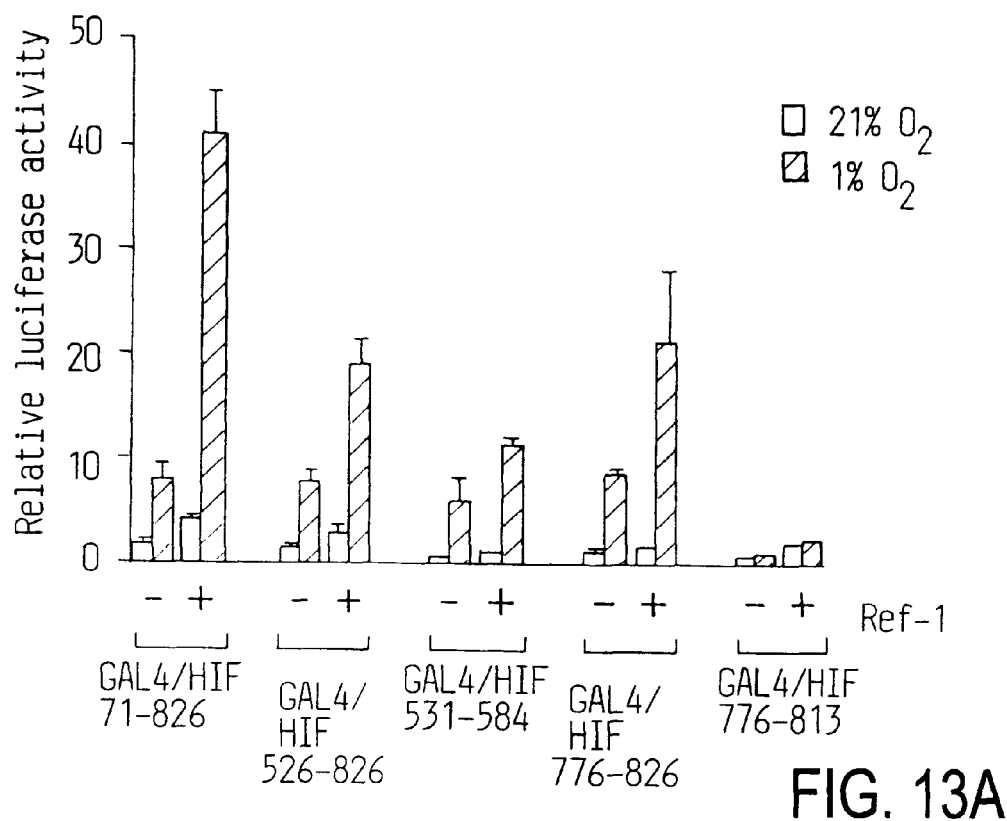
FIG. 13 Ref-1 enhances HIF-1α function. (A) COS7 cells were cotransfected with different GAL4/HIF-1α fusion constructs together with a GAL4-responsive reporter plasmid in the absence or presence of 1.5 μg of Ref-1 (pCMV5/Ref-1), as indicated. Cells were exposed to 21 or 1% $O_2$ before harvest. After normalization for transfection efficiency using alkaline phosphatase activity, reporter gene activities are expressed as relative to that of GAL4 in normoxia. The results of two independent experiments performed in duplicate ±S.E. are shown. (B) Ref-1 potentiates CBP and SRC-1 activation of HIF-1α. The same GAL4/HIF-1α fusion proteins as shown in (A) were cotransfected into COS7 cells together with a GAL4-responsive reporter plasmid in the absence or presence of different combinations of Ref-1 (0.75 μg), CBP (0.75 μg), and/or SRC-1 (0.75 μg), as indicated. The bottom panel shows an enlargement of the area marked with dots.
Figure 14:
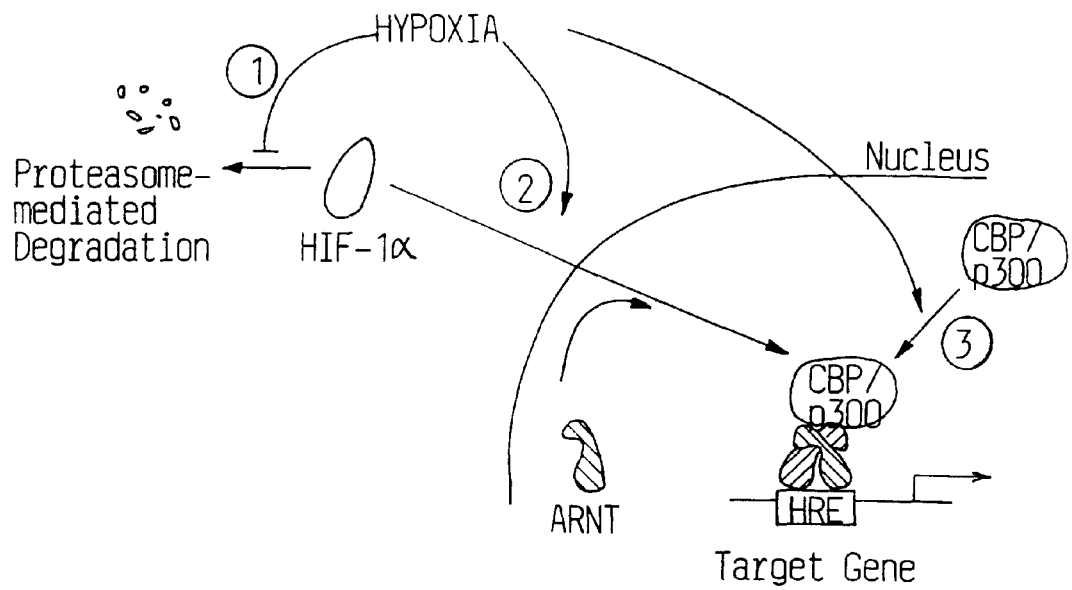
FIG. 14 Model of multiple levels of regulation of HIF-1α activity. Hypoxia leads to inhibition of proteasome-mediated degradation and consequently to stabilization of the protein (1), and stimulates the nuclear import of HIF-1α by unmasking its nuclear localization signal (2). Subsequently, the Arnt partner factor is recruited HIF-1α in the nucleus and the resulting HIF-1α/Arnt heterodimer recognizes hypoxia responsive elements (HREs) of target genes and (3) functionally interacts with transcriptional coactivators (examplified by CBP/p300) to activate target promoters. The order of events within the nucleus (Arnt dimerization, DNA binding, and recruitment of CBP) is not yet known.

The nuclear redox regulator Ref-1 is known to stabilize the DNA binding activity of AP-1 by reduction of a conserved cysteine residue of Fos and Jun. Ref-1 is a bifunctional enzyme: it harbors both redox and endonuclease DNA repair activities (Xanthoudakis et al. (1992) EMBO J. 11, 3323–3335) and has been implicated in up-regulation of HIF-1α-dependent induction of gene expression under hypoxic conditions (Huang et al. (1996) J. Biol. Chem. 271, 32253–32259). Against this background we wanted to further investigate the effect of Ref-1 on HIF-1α-dependent transcriptional activation, and to examine its effect on the functional interaction of HIF-1α with the coactivators CBP and SRC-1. To investigate whether HIF-1α is a target of regulation by Ref-1 we initially used the different GAL4 DBD is fusion proteins containing distinct subfragments of HIF-1α. As shown in FIG. 13A, transient overexpression of Ref-1 markedly potentiated hypoxic induction of reporter gene expression by the fusion proteins GAL4/HIF 71–826 and GAL4/HIF 526–826 spanning both transactivation domain of HIF-1α. The transcriptional activation function of GAL4/HIF 531–584 containing the N-terminal transactivation domain of HIF-1α was only very moderately but significantly stimulated by Ref-1 in hypoxic cells, whereas Ref-1 produced more potent regulation of hypoxia-inducible transactivation by GAL4/HIF 776–826 containing the C-terminal transactivation domain (FIG. 13A).

Figure 13B:
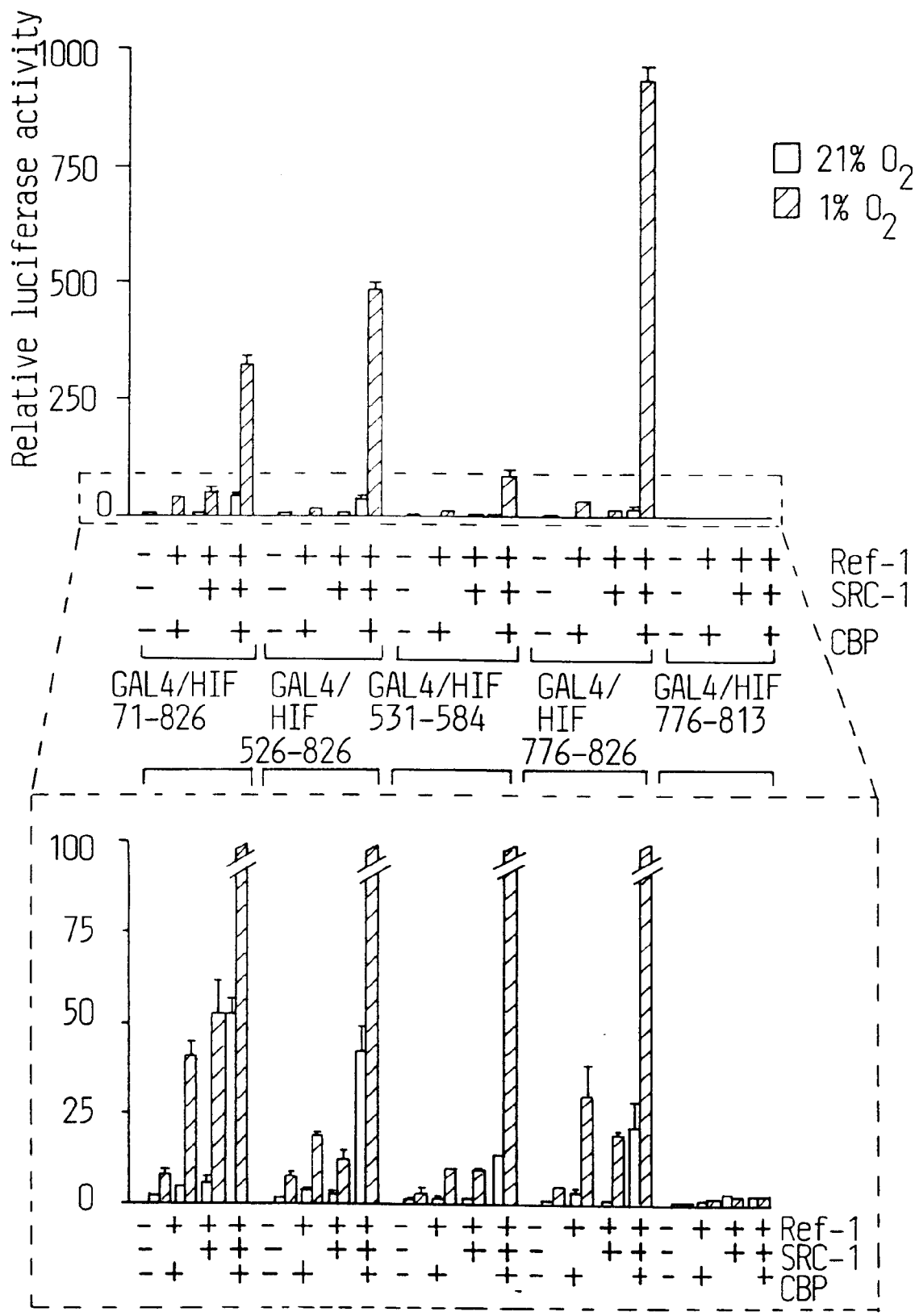

Given the striking potentiation of HIF-1α function by the coactivators CBP and SRC-1 we next examined the effect of Ref-1 on transcriptional activation by the GAL4-HIF-1α fusion proteins in combination with CBP, SRC-1, or both proteins. Following transient expression of Ref-1 together with either CBP or SRC-1 hypoxia-inducible transcriptional activation by the tested GAL4-HIF-1α fusion proteins was not significantly altered in comparison to the results obtained in the presence of the fusion proteins and Ref-1 alone (FIG. 13B). Remarkably, however, the hypoxia-inducible transcriptional potencies of all the fusion proteins containing either both or the individual HIF-1α transactivation domains were dramatically (10- to 53-fold) enhanced by coexpression of Ref-1 in the presence of CBP and SRC-1 (FIG. 13B). Under these conditions, the fusion proteins spanning the N- or C-terminal transactivation domains produced 12- or 53-fold hypoxia-dependent activation responses, respectively, whereas the fusion protein containing the C-terminal transactivation domain lacking the CBP interaction interface, GAL4/HIF 776–813, showed no regulation by Ref-1 and the coactivators. Thus, these data indicate that these two coactivators may have been limiting under these conditions for the Ref-1-mediated effect on HIF-1α-dependent transcription. Moreover, these results clearly demonstrate that both the N-terminal and C-terminal transactivation domains HIF-1α are targets of regulation by Ref-1, implying that Ref-1 together with the CBP and SRC-1 classes of transcriptional coactivators plays a key role in regulation of HIF-1α function. Moreover, this is the first example of a transactivation domain representing a target of regulation by Ref-1, and, conversely, these data represent the first example of a noncovalent protein modifier of the HIF-1α transactivation domains identified in mammalian cells.

The precise mechanism by which Ref-1 activates HIF-1α is not known. Interestingly, a GFP-tagged Ref-1 fusion protein was exclusively localized in the nucleus both under normoxic and hypoxic conditions indicating that nuclear translocation of HIF-1α is required for functional interaction with Ref-1. This redox regulator protein has been shown to form complexes with Jun in vitro (Xanthoudakis et al. (1994) Proc. Natl. Acad. Sci. USA 91, 23–27). To further investigate whether Ref-1 could interact with HIF-1α, we tried to trap the interaction by using a crosslinking reagent such as diamide, which oxidizes cysteine sulfhydryls to disulfides. A series of experiments was performed with GST-tagged purified Ref-1. [$^{35}$S]methionine-labeled in vitro translated GAL4/HIF 1–826 was incubated with GST/Ref-1 in the presence or absence of diamide. GAL4/HIF 1–826 was found to weakly bind GST/Ref-1 and the crosslinking agent stabilized this interaction between Ref-1 and GAL4/HIF. No binding of [$^{35}$S]methionine-labeled GAL4/HIF was observed when it was incubated either with the anti-GST affinity gel alone in the absence of GST/Ref-1 or when it was incubated with purified GST, indicating that there was no significant background binding.

Next, we tried a series of pull-down experiments with [$^{35}$S]methionine-labeled in vitro translated GAL4/HIF 776–826 and GAL4/HIF 531–584. GAL4/HIF 531–584 bound GST/Ref-1, and no effect of diamide was observed, consistent with the absence of cysteine residues in the N-terminal transactivation domain of HIF-1α. An interaction between GAL4/HIF 726–826 and GST/Ref-1 was also detected, and this interaction was enhanced in the presence of diamide. In excellent agreement with this observation the C-TAD contains two cysteine residues. Low levels of background binding of the labeled proteins to GST was observed in the presence or absence of diamide. Immunoblot analysis verified that the input concentrations of GST/Ref-1 or GST alone were similar.

The experiments above established that Ref-1 potentiates the effect of both the CBP and SRC-1 coactivators on hypoxia-inducible promoter activation by HIF-1α. Moreover, Ref-1 functionally and physically interacted with the distinct N- and C-terminal transactivation domains of HIF-1α. However, only the C-terminal and not the N-terminal transactivation domain of HIF-1α contains cysteine residues through which Ref-1 regulation occurs (Xanthoudakis et al. (1992) EMBO J. 11, 3323–3335). These data indicate that an auxiliary factor, possibly a coactivator, may mediate interaction with at least the N-terminal transactivation domain of HIF-1α.

MATERIALS AND METHODS (a) Reagents pCMX-SAH/Y145F expression vector encoding a modified and highly chromophoric form of GFP under the control of cytomegalovirus (CMV) immediate early promoter was a generous gift from Dr. Kazuhiko Umesono (Kyoto University, Japan). This humanized GFP (SAH/Y145F) contains a S65A mutation which confers a wavelength shift and temperature resistance to the protein as well as a Y145P substitution increasing the intracellular stability of GFP. pRc/RSV-mCBP-HA construct expressing full-length mouse CBP was a gift from Dr. Richard H. Goodman (Vollum Institute, Oregon). The vector expressing a GFP-fusion of full-length HIF-1α was generated by cutting the HIF-1α coding region from pGEX-4T3-HIF-1α as a BamHI/NotI fragment (NotI site filled-in with Klenow polymerase) and ligating this in-frame into BamHI/NheI opened pCMX-SAH/Y145F where the NheI site had been blunt-ended with Klenow. Deletion mutant HIF-1α/1–652 was assembled by inserting a BamHI/SpeI fragment of HIF-1α into BamHI/NheI-digested pCMX-SAH/Y145F. GFP fusions encoding HIF-1α subfragments (corresponding to amino acids 331–641, 526–641, and 526–826) were generated by amplifying the equivalent DNA sequences by PCR using Pfu DNA polymerase (Stratagene) together with primer pairs carrying BamHI or NheI ends. The resulting products were inserted into BamHI/NheI opened pCMX-SAH/Y145F. GFP fusions carrying amino terminal sequences HIF-1α (1–74, 1–245, 1–330) were cut out from corresponding bacterial GST fusion expression vectors and inserted in frame to BamHI/NheI site (NheI blunt-ended) of pCMX-SAH/Y145F. GFP-HIF-1α fusion proteins ending at amino acid 813 were generated by cleaving the C-terminal 13 amino acids by PstI digestion. Corresponding GAL4 DNA-binding domain fusion proteins were assembled by cleaving the HIF-1α inserts as BamHI/NheI fragments and religating them into pCMX expression vector.

Site-directed mutagenesis of the C-terminal NLS was performed by overlap PCR (Ausubel et al., 1994) where the desired mutation (codon 719 AAG->ACA was introduced into a PCR product and then inserted as an EcoRI-PstI subfragment into pGFP-HIF-1α/526–826. A GFP fusion of full-length HIF-1α carrying K719T mutation was thereafter assembled by inserting the amino terminal BamHI-SpeI fragment of HIF-1α into pGFP-HIF-1α/526–826 K719T. PCR-based mutagenesis with specific oligonucleotides was employed to generate mutations to the N-terminal NLS motif. Fidelity of PCR reactions and identity of constructs was confirmed by sequencing the inserts.

(b) Cell Culture and Transfections

COS7 cells (from ATCC) were routinely maintained in Dulbecco's minimal essential medium (DMEM) supplemented with 10% fetal calf serum plus penicillin (50 IU/ml) and streptomycin (50 μg/ml). For analysis of nuclear translocation of HIF-1α in living cells, we transiently expressed GFP-tagged HIF-1α and its various mutant plasmids in COS7 cells. The cells were cultured on the silane-coated cover slips in 6-cm diameter plastic dishes, and the medium was changed to OPTI-MEM medium lacking phenol red (Life Technologies, Inc.) before transfection. A plasmid cocktail containing 6 μg of the expression plasmids for GFP-tagged HIF-1α and its various mutants was mixed with 12 μl of TransIT-LT1 reagent (Panvera Corp., Madison, Wis.) and added to the culture. After 6 h of incubation, the medium was replaced with DMEM with 10% FCS. Cells were induced 24 h later with 1% $O_2$, 100 μM 2,2'-dipyridyl or 100 μM $CoCl_2$ or treated with vehicle only.

Transcriptional activity of GFP and GAL4 fusion constructs was analyzed in a cotransfection assay where effector plasmids (0.2 μg/30-mm dish) together with a reporter gene (1.5 μg/30-mm dish) were introduced into COS7 or HeLa cells. The reporter plasmid encoded firefly luciferase gene under the control of thymidine kinase minimal promoter and either five or three copies of GAL4 or HIF-responsive elements, respectively.

(c) Immunocytochemical Analysis

COS7 cells grown on fibronectin-coated cover-slips were transiently transfected with the expression plasmid for full-length HIF-1α (pCMV-HIF-1α) or HIF-1α fused to the GAL4 DNA binding domain (pCMX-GAL4-HIF-1α). After various treatments, the cells were fixed with 4% paraformaldehyde in PBS at room temperature for 30 min. Immunostaining of the cells was carried out using anti-HIF-1α antiserum (Kallio et al. (1997) Proc. Natl. Acad. Sci. USA 94, 5667–5672) or anti-GAL4-DBD antiserum (Upstate Biotechnology) and the appropriate biotinylated-second antibodies and streptoavidin-conjugated fluorescein isothiocyanate or Texas Red (Amersham). The cover-slips were mounted on glass slides and subjected to microscopic analysis.

(d) Visualization of Intracellular Trafficking of GFP-tagged Proteins in Living Cells Transiently expressed GFP was expressed at detectable levels between 24 and 72 h after transfection. Routinely, cells were used for further experiments 48 h after transfection. After various treatments, cells were examined using a Zeiss Axiovert 135 microscope enclosed by an incubator and equipped with a heating-stage, an FITC-filter set, and epifluorescence with illumination from a Gixenon burner (Carl Zeiss Jena GmbH, Jena, Germany). Photographs were taken using Kodak Echtachrome 400, and semi-quantitative assessment of the subcellular localization of the GFP-tagged proteins was performed according to the methods described by Ylikomi et al. ((1992) EMBO J. 11, 3681–3694). In brief, subcellular localization of GFP-tagged proteins was performed by a blinded observer, counting approximately 200 cells in which GFP fluorescence was detected. The GFP fluorescence-positive cells were classified into four different categories: N<C for cytoplasmic dominant fluorescence; N=C, cells having equal distribution of fluorescence in the cytoplasmic and nuclear compartments; N>C for nuclear-dominant fluorescence; and N for exclusive nuclear fluorescence.

(e) Immunoblotting and Detection

For the detection of the HIF-1α fusion protein expression, whole cell extracts were prepared essentially as described (Kallio et al. (1997) Proc. Natl. Acad. Sci. USA 94, 5667–5672). Briefly, cells were harvested in TEN buffer (40 mM Tris-HCl, pH 7.9; 10 mM EDTA; 150 mM NaCl). The cell pellet was frozen in liquid nitrogen and thawed by resuspending in 80 μl of cell extraction buffer (10 mM Hepes, pH 7.9; 400 mM NaCl; 0.1 mM EDTA; 5% (v/v) glycerol; 1 mM dithiotreitol; 1 mM phenylmethylsulfonyl fluoride), followed by centrifugation for 30 min at maximal velocity. Fifty μg of the total cell proteins were blotted after SDS polyacrylamide gel electrophoresis onto nitrocellulose filter and blocked overnight with 5% nonfat milk in PBS. Anti-HIF-1α antiserum was used as a primary antibody as 1:500 dilution in PBS containing 1% nonfat milk for 2 hours. After washes, 1:750 dilution of anti-rabbit IgG-horseradish peroxidase conjugate (Amersham) in PBS/1% nonfat milk was used as a secondary antibody. After extensive washing with PBS the complexes were visualized using enhanced chemiluminescence (Amersham) according to the manufacturer's instructions.

TABLE I

Subcellular distribution of GFP-HIF-1α chimeras. Cells were transfected as duplicates with indicated fusion constructs and 24 h after transfection induced with 100 μM 2,2'-dipyridyl or with vehicle only for 6 h before microscopic observation and cell counting. Cells were classified into four categories: N, cells containing exclusively nuclear fluorescence; N > C, cells in which the nuclear fluorescence exceeds the cytoplasmic fluorescence; N = C, cells having equal distribution of fluorescence; and N < C, cells having cytoplasmic fluorescence exceeding that in the nucleus. A total of 200 to 300 cells were analyzed for the distribution of fluorescence and the percentage of cells belonging to each category is indicated in the table.

|  | Normoxia | | | | Hypoxia (Dipyridyl) | | | |
| --- | --- | --- | --- | --- | --- | --- | --- | --- |
|  | N | N > C | N = C | N < C | N | N > C | N = C | N < C |
| GFP | 0 | 0 | 100 | 0 | 0 | 0 | 100 | 0 |
| GFP-HIF-1α | 8 | 27 | 65 | 0 | 90 | 7 | 3 | 0 |
| GFP-HIF-1α/1–74 | 69 | 20 | 11 | 0 | 56 | 35 | 9 | 0 |
| GFP-HIF-1α/1–245 | 36 | 38 | 26 | 0 | 31 | 43 | 26 | 0 |
| GFP-HIF-1α/1–330 | 0 | 9 | 91 | 0 | 0 | 5 | 95 | 0 |
| GFP-HIF-1α/Δ178–390 | 57 | 23 | 20 | 0 | 42 | 29 | 29 | 0 |
| GFP-HIF-1α/331–641 | 0 | 0 | 100 | 0 | 0 | 0 | 100 | 0 |
| GFP-HIF-1α/526–641 | 0 | 0 | 100 | 0 | 0 | 0 | 100 | 0 |
| GFP-HIF-1α/1–652 | 0 | 0 | 0 | 100 | 0 | 0 | 0 | 100 |
| GFP-HIF-1α/526–826 | 100 | 0 | 0 | 0 | 100 | 0 | 0 | 0 |
| GFP-HIF-1α/526–813 | 90 | 10 | 0 | 0 | 83 | 11 | 3 | 0 |

TABLE II

Subcellular distribution of GFP-HIF-1α chimeras carrying point mutations in the NLS motifs. Cells were transfected as duplicates with indicated fusion constructs and 24 h after transfection induced with 100 μM 2,2'-dipyridyl or with vehicle only for 6 h before microscopic observation and cell counting. Cells were classified into four categories as outlined in Table I. A total of 200 to 300 cells were analyzed for the distribution of fluorescence and the percentage of cells belonging to each category is indicated in the table.

|  | Normoxia | | | | Hypoxia (Dipyridyl) | | | |
| --- | --- | --- | --- | --- | --- | --- | --- | --- |
|  | N | N > C | N = C | N < C | N | N > C | N = C | N < C |
| GFP-HIF-1αK719T | 0 | 0 | 4 | 96 | 0 | 0 | 19 | 81 |
| GFP-HIF-1αR18A | 37 | 15 | 48 | 0 | 82 | 6 | 12 | 0 |
| GFP-HIF-1αR17G/R18G | 50 | 24 | 26 | 0 | 84 | 8 | 18 | 0 |
| GFP-HIF-1α/Δ178–390K719T | 0 | 0 | 18 | 82 | 0 | 0 | 15 | 85 |
| GFP-HIF-1α/526–826K719T | 26 | 24 | 50 | 0 | 15 | 14 | 71 | 0 |

What is claimed is:

1. A method for identifying compounds which modulate the function of a functional domain of human HIF-1α having the sequence SEQ ID NO:1, said method comprising:
   (i) contacting a candidate compound with a modified human HIF-1α, said modified human HIF-1α lacking at least one functional domain of native human HIF-1α, or having at least one functional domain of native human HIF-1α which is inactive, said functional domain or domains being selected from the group consisting of
      (a) the PAS-B domain located in sequence SEQ ID NO:1 between amino acids 178 and 390,
      (b) the C-terminal nuclear localization sequence located in sequence SEQ ID NO:1 from amino acids 718 to 721,
      (c) the transactivator domain located in sequence SEQ ID NO:1 between amino acids 531 to 584, and
      (d) the transactivator domain located in sequence SEQ ID NO:1 between amino acids 813 and 826, and
   (ii) determining the effect of the candidate compound on the modified human HIF-1α;
wherein the method is carried out in the presence of a transcriptional coactivator selected from the group consisting of SRC-1, TIF2 and mixtures thereof.

2. The method according to claim 1, comprising:
   (i) contacting a candidate compound with a cell expressing said modified human HIF-1α, said modified human HIF-1α being conjugated to a molecular probe, and
   (ii) detecting the localization of the molecular probe within the cell.

3. The method according to claim 2, wherein the molecular probe is a fluorescent probe, and wherein a change in the relative fluorescence of the nucleus to the cytoplasm is indicative for a compound which modulates the function of the functional domain.

4. The method according to claim 3, wherein the molecular probe is selected from the group consisting of *Aequeora victoria* Green Fluorescent Protein and variants thereof.

5. The method according to claim 1, wherein the modified human HIF-1α is regulating the activity of a reporter gene; a change in the activity of the reporter gene being indicative of a compound which modulates the function of the functional domain.

6. The method according to claim 2, wherein the modified human HIF-1α is fused to the DNA binding domain of GAL4, and wherein the cells contain a GAL4 response element operatively liked to a reporter gene.

7. The method according to claim 6, wherein the modified human HIF-1α is fused to the *Aequeora victoria* Green Fluorescent Protein, and wherein the cells contain an erythropoietin hypoxia response element operatively linked to a reporter gene.

8. The method according to claim 6, wherein the reporter gene is firefly luciferase gene.

9. The method according to claim 1, carried out in the presence of the redox regulator protein Ref-1.

10. The method according to claim 1, wherein the functional domain is the PAS-B domain.

11. The method according to claim 1, wherein the modified human HIF-1α is selected from the group consisting of
    HIF-1α/1–74, SEQ ID NO: 2;
    HIF-1α/1–245, SEQ ID NO: 3;
    HIF-1α/Δ178–390, SEQ ID NO: 6;
    HIF-1α/331–641, SEQ ID NO: 7;
    HIF-1α/526–641, SEQ ID NO: 8;
    HIF-1α/526–813, SEQ ID NO: 9; and
    HIF-1α/526–826, SEQ ID NO: 10.

12. The method according to claim 1, wherein the functional domain is the C-terminal nuclear localization sequence domain.

13. The method according to claim 12, wherein the modified human HIF-1α is selected from the group consisting of
    HIF-1α/1–74, SEQ ID NO: 2;
    HIF-1α/1–245, SEQ ID NO: 3;

HIF-1α/1–330, SEQ ID NO: 4;
HIF-1α/1–652, SEQ ID NO: 5;
HIF-1α/331–641, SEQ ID NO: 7; and
HIF-1α/526–641, SEQ ID NO: 8.

14. The method according to claim 1, wherein the functional domain is the transactivator domain located in SEQ ID NO:1 between amino acids 531 to 584.

15. The method according to claim 14, wherein the modified human HIF-1α is selected from the group consisting of
HIF-1α/1–74, SEQ ID NO: 2;
HIF-1α/1–245, SEQ ID NO: 3;
HIF-1α/1–330, SEQ ID NO: 4;
HIF-1α/776–826, SEQ ID NO: 14; and
HIF-1α/776–813, SEQ ID NO: 15.

16. The method according to claim 1, wherein the functional domain is the transactivator domain located in sequence SEQ ID NO:1 between amino acids 813 and 826.

17. The method according to claim 16, wherein the modified human HIF-1α is selected from the group consisting of
HIF-1α/1–74, SEQ ID NO: 2;
HIF-1α/1–245, SEQ ID NO: 3;
HIF-1α/1–330, SEQ ID NO: 4;
HIF-1α/1–652, SEQ ID NO: 5;
HIF-1α/331–641, SEQ ID NO: 7;
HIF-1α/526–641, SEQ ID NO: 8;
HIF-1α/526–813, SEQ ID NO: 9;
HIF-1α/1–813, SEQ ID NO: 12;
HIF-1α/531–584, SEQ ID NO: 13; and
HIF-1α/776–813, SEQ ID NO: 15.

18. The method according to claim 7, wherein the reporter gene is firefly luciferase gene.

19. The method according to claim 3, wherein the molecular probe is *Aequeora victoria* Green Fluorescent Protein.

20. A method for identifying compounds which modulate the function of a functional domain of human HIF-1α comprising:
   (i) contacting a candidate compound with a variant of human HIF-1α, and
   (ii) determining the effect of the candidate compound on the variant;
wherein the variant has an amino acid sequence selected from the group consisting of:
   SEQ ID NO: 2,
   SEQ ID NO: 3,
   SEQ ID NO: 4,
   SEQ ID NO: 5,
   SEQ ID NO: 6,
   SEQ ID NO: 7,
   SEQ ID NO: 8,
   SEQ ID NO: 9,
   SEQ ID NO: 10,
   SEQ ID NO: 11,
   SEQ ID NO: 12,
   SEQ ID NO: 13,
   SEQ ID NO: 14 and
   SEQ ID NO: 15
wherein the method is carried out in the presence of a transcriptional coactivator selected from the group consisting of SRC-1, TIF2 and mixtures thereof.

21. The method according to claim 20, comprising
   (i) conjugating the variant of human HIF-1α with a molecular probe,
   (ii) contacting a candidate compound with a cell expressing the variant of human HIF-1α conjugated to the molecular probe, and
   (iii) detecting the localization of the molecular probe within the cell.

22. A method according to claim 20, comprising the steps of:
   (i) conjugating the variant to a molecular probe to obtain an expression vector;
   (ii) co-transfecting a cell with the expression vector and a transcriptional coactivator selected from the group consisting of SRC-1, TIF2 and mixtures thereof;
   (iii) contacting the cell with a candidate compound;
   (iv) incubating the cell under conditions which induce nuclear translocation of human HIF-1α having the sequence SEQ ID NO:1; and
   (v) detecting the localization of the molecular probe within the cell.

23. The method according to claim 22, wherein the cell is incubated in hypoxic conditions.

24. The method according to claim 22, wherein the cell is incubated in the presence of a hypoxia-mimicking chemical.

25. A method according to claim 20, comprising the steps of:
   (i) providing the variant;
   (ii) providing a cell comprising a hypoxia response element operatively linked to a reporter gene;
   (ii) co-transfecting the cell with the variant and a transcriptional coactivator selected from the group consisting of SRC-1, TIF2 and mixtures thereof,
   (iii) contacting the cell with a candidate compound;
   (iv) incubating the cell under conditions which induce nuclear translocation of human HIF-1α having the sequence SEQ ID NO:1; and
   (v) determining the reporter gene activity.

26. The method according to claim 25, wherein the cells contain an erythropoietin hypoxia response element operatively linked to a reporter gene.

27. A method for identifying compounds which modulate the function of a functional domain of human HIF-1α having the sequence SEQ ID NO:1, said method comprising:
   (i) providing a protein having the sequence SEQ ID NO:1 with the proviso that the protein is lacking at least one of the following portions of SEQ ID NO: 1:
      (a) the portion consisting of amino acids 178 to 390,
      (b) the portion consisting of amino acids 531 to 584,
      (c) the portion consisting of amino acids 718 to 721,
      (d) the portion consisting of amino acids 813 to 826;
   (ii) conjugating a protein to a molecular probe to obtain an expression vector;
   (ii) co-transfecting a cell with the expression vector and a transcriptional coactivator selected from the group consisting of SRC-1, TIF2 and mixtures thereof;
   (iii) exposing the cell to a candidate compound;
   (iv) incubating the cell under conditions which induce nuclear translocation of human HIF-1α having the sequence SEQ ID NO:1; and
   (v) detecting the localization of the molecular probe within the cell.

28. The method according to claim 27, wherein the protein is lacking the portion of SEQ ID NO:1 comprising amino acids 813 and 826.

29. A method for identifying compounds which modulate the function of a functional domain of human HIF-1α having the sequence SEQ ID NO:1, said method comprising:
(i) contacting a candidate compound with a modified human HIF-1α, said modified human HIF-1α lacking at least one functional domain of native human HIF-1α, or having at least one functional domain of native human HIF-1α which is inactive, said functional domain or domains being selected from the group consisting of
    (a) a C-terminal nuclear localization sequence located in sequence SEQ ID NO:1 from amino acids 718 to 721, and
    (b) a transactivator domain located in sequence SEQ ID NO:1 between amino acids 531 to 584, and
(ii) determining the effect of the candidate compound on the modified human HIF-1α.

30. A method for identifying compounds which modulate the function of a functional domain of human HIF-1α having the sequence SEQ ID NO:1, said method comprising:
(i) contacting a candidate compound with a modified human HIF-1α, said modified human HIF-1α lacking at least one functional domain of native human HIF-1α, or having at least one functional domain of native human HIF-1α which is inactive, said functional domain or domains being selected from the group consisting of
    (a) a PAS-B domain located in sequence SEQ ID NO:1 between amino acids 178 and 390,
    (b) a C-terminal nuclear localization sequence located in sequence SEQ ID NO:1 from amino acids 718 to 721, and
    (c) a transactivator domain located in sequence SEQ ID NO:1 between amino acids 813 and 826, and
(ii) determining the effect of the candidate compound on the modified human HIF-1α;
wherein the method is carried out in the presence of a transcriptional coactivator selected from the group consisting of SRC-1, TIF2 and mixtures thereof.

31. A method for identifying compounds which modulate the function of human HIF-1α, wherein the human HIF-1α comprises:
    (a) a PAS-B domain located between amino acids 178 and 390,
    (b) a C-terminal nuclear localization sequence located from amino acids 718 to 721,
    (c) a transactivator domain located between amino acids 531 to 584, and
    (d) a transactivator domain located between amino acids 813 and 826,
wherein the method comprises:
    (i) contacting a candidate compound with a modified human HIF-1α, said modified human HIF-1α lacking at least one functional domain of native human HIF-1α, or having at least one functional domain of native human HIF-1α which is inactive, said functional domain or domains being selected from the group consisting of:
        (a) the C-terminal nuclear localization sequence located from amino acids 718 to 721 of native human HIF-1α, and
        (b) the transactivator domain located between amino acids 531 to 584 of native human HIF-1α, and
    (ii) determining the effect of the candidate compound on the modified human HIF-1α.

32. A method according to claim 31, wherein the modified human HIF-1α is selected from the group consisting of:
SEQ ID NO: 2,
SEQ ID NO: 3,
SEQ ID NO: 4,
SEQ ID NO: 5,
SEQ ID NO: 6,
SEQ ID NO: 7, and
SEQ ID NO: 8.

33. A method according to claim 31, wherein the modified human HIF-1α is selected from the group consisting of:
SEQ ID NO: 2,
SEQ ID NO: 3,
SEQ ID NO: 4,
SEQ ID NO: 14, and
SEQ ID NO: 15.

34. A method according to claim 31 wherein the human HIF-1α is a basic-helix-loop-helix-PAS protein.

35. A method for identifying compounds which modulate the function of a functional domain of human HIF-1α, wherein the human HIF-1α is a basic-helix-loop-helix-PAS protein comprising a PAS-B domain, a C-terminal nuclear localization sequence, a first transactivator domain and a second transactivator domain; the method comprising:
    (i) contacting a candidate compound with a modified human HIF-1α, and
    (ii) determining the effect of the candidate compound on the modified human HIF-1α;
wherein the modified HIF-1α differs from native HIF-1α in that at least one domain selected from the PAS-B domain, the C-terminal nuclear localization sequence, the first transactivator domain and the second transactivator domain is lacking or inactive; and further wherein the method is carried out in the presence of a transcriptional coactivator selected from the group consisting of SRC-1, TIF2 and mixtures thereof.

36. A method according to claim 1, wherein the modified human HIF-1α comprises at least 38 amino acids.

37. A method according to claim 30, wherein the modified human HIF-1α comprises at least 38 amino acids.

38. A method according to claim 35, wherein the modified human HIF-1α comprises at least 38 amino acids.

39. A method according to claim 1, wherein the modified human HIF-1α comprises from 38 to 813 amino acids.

40. A method according to claim 30, wherein the modified human HIF-1α comprises from 38 to 813 amino acids.

41. A method according to claim 35, wherein the modified human HIF-1α comprises from 38 to 813 amino acids.

42. A method according to claim 1, wherein the modified human HIF-1α comprises from 38 to 826 amino acids, and wherein at least one functional domain of native human HIF-1α selected from the group consisting of
    (a) the PAS-B domain located in sequence SEQ ID NO:1 between amino acids 178 and 390,
    (b) the C-terminal nuclear localization sequence located in sequence SEQ ID NO:1 from amino acids 718 to 721,
    (c) the transactivator domain located in sequence SEQ ID NO:1 between amino acids 531 to 584, and
    (d) the transactivator domain located in sequence SEQ ID NO:1 between amino acids 813 and 826 is inactive.

43. A method according to claim 30, wherein the modified human HIF-1α comprises from 38 to 826 amino acids, and wherein at least one functional domain of native human HIF-1α selected from the group consisting of
  (a) the PAS-B domain located in sequence SEQ ID NO:1 between amino acids 178 and 390,
  (b) the C-terminal nuclear localization sequence located in sequence SEQ ID NO:1 from amino acids 718 to 721, and
  (c) the transactivator domain located in sequence SEQ ID NO:1 between amino acids 813 and 826 is inactive.

44. A method according to claim 35, wherein the modified human HIF-1α comprises from 38 to 826 amino acids, wherein at least one functional domain of native human HIF-1α selected from the group consisting of the PAS-B domain, the C-terminal nuclear localization, the first transactivator domain and the second transactivator domain is inactive.

45. A method according to claim 1, wherein the modified human HIF-1α exhibits an activity selected from the group consisting of:
  hypoxia-inducible nuclear translocation,
  hypoxia-inducible nuclear accumulation,
  nuclear export upon withdrawal of a hypoxic signal,
  hypoxia-dependent recruitment of CBP coactivator,
  interaction with transcriptional coactivator TIF2 in vivo,
  interaction with transcriptional coactivator SRC-1 in vivo,
  hypoxia-dependent physical interaction with Ref-1,
  dimerization with Arnt and mixtures thereof.

46. A method according to claim 30, wherein the modified human HIF-1α exhibits an activity selected from the group consisting of:
  hypoxia-inducible nuclear translocation,
  hypoxia-inducible nuclear accumulation,
  nuclear export upon withdrawal of a hypoxic signal,
  hypoxia-dependent recruitment of CBP coactivator,
  interaction with transcriptional coactivator TIF2 in vivo,
  interaction with transcriptional coactivator SRC-1 in vivo,
  hypoxia-dependent physical interaction with Ref-1,
  dimerization with Arnt and mixtures thereof.

47. A method for identifying compounds which modulate the function of a functional domain of human HIF-1α having the sequence SEQ ID NO:1, said method comprising:
  (i) contacting a candidate compound with a cell expressing a modified human HIF-1α, said modified human HIF-1α being conjugated to a molecular probe and lacking at least one functional domain of native human HIF-1α, or having at least one functional domain of native human HIF-1α which is inactive, said functional domain or domains being selected from the group consisting of
    (a) the PAS-B domain located in sequence SEQ ID NO:1 between amino acids 178 and 390,
    (b) the C-terminal nuclear localization sequence located in sequence SEQ ID NO:1 from amino acids 718 to 721,
    (c) the transactivator domain located in sequence SEQ ID NO:1 between amino acids 531 to 584, and
    (d) the transactivator domain located in sequence SEQ ID NO:1 between amino acids 813 and 826, and
  (ii) detecting the localization of the molecular probe within the cell, a change in the localization of the molecular probe being indicative of a compound capable of modulating the function of the functional domain.

48. A method for identifying compounds which modulate the function of a C-terminal nuclear localization sequence located in sequence SEQ ID NO:1 from amino acids 718 to 721, said method comprising:
  (i) contacting a candidate compound with a modified human HIF-1α, said modified human HIF-1α lacking the C-terminal nuclear localization sequence located in sequence SEQ ID NO:1 from amino acids 718 to 721, or having the C-terminal nuclear localization sequence located in sequence SEQ ID NO:1 from amino acids 718 to 721 inactive, and
  (ii) determining the effect of the candidate compound on the modified human HIF-1α.

49. The method according to claim 47, carried out in the presence of the redox regulator protein Ref-1.

50. A method according to claim 41, wherein the modified human HIF-1α exhibits an activity selected from the group consisting of:
  hypoxia-inducible nuclear translocation,
  hypoxia-inducible nuclear accumulation,
  nuclear export upon withdrawal of a hypoxic signal,
  hypoxia-dependent recruitment of CBP coactivator,
  interaction with transcriptional coactivator TIF2 in vivo,
  interaction with transcriptional coactivator SRC-1 in vivo,
  hypoxia-dependent physical interaction with Ref-1,
  dimerization with Arnt and mixtures thereof.

* * * * *